US009023897B2

(12) United States Patent
Gaudriault

(10) Patent No.: US 9,023,897 B2
(45) Date of Patent: May 5, 2015

(54) BIODEGRADABLE DRUG DELIVERY COMPOSITIONS

(75) Inventor: Georges Gaudriault, Montpellier (FR)

(73) Assignee: MedinCell, Montpellier (FR)

( * ) Notice: Subject to any disclaimer, the term of this patent is extended or adjusted under 35 U.S.C. 154(b) by 463 days.

(21) Appl. No.: 13/340,265

(22) Filed: Dec. 29, 2011

(65) Prior Publication Data

US 2012/0172454 A1 Jul. 5, 2012

Related U.S. Application Data

(60) Provisional application No. 61/428,007, filed on Dec. 29, 2010.

(51) Int. Cl.

| | |
|---|---|
| ***A61K 47/00*** | (2006.01) |
| ***A61K 9/00*** | (2006.01) |
| ***A01N 25/10*** | (2006.01) |
| ***A61K 47/34*** | (2006.01) |
| ***A61K 38/26*** | (2006.01) |
| ***A61K 31/167*** | (2006.01) |
| ***A61K 31/485*** | (2006.01) |
| ***A61K 31/519*** | (2006.01) |
| ***A61K 31/7048*** | (2006.01) |

(52) U.S. Cl.

CPC .............. *A61K 9/0019* (2013.01); *A01N 25/10* (2013.01); *A61K 47/34* (2013.01); *A61K 38/26* (2013.01); *A61K 31/167* (2013.01); *A61K 31/485* (2013.01); *A61K 31/519* (2013.01); *A61K 31/7048* (2013.01)

(58) Field of Classification Search

CPC ...................................................... A61K 47/34

See application file for complete search history.

(56) References Cited

U.S. PATENT DOCUMENTS

| | | | | |
|---|---|---|---|---|
| 4,526,938 | A | 7/1985 | Churchill et al. | |
| 4,938,763 | A | 7/1990 | Dunn et al. | |
| 5,077,049 | A | 12/1991 | Dunn et al. | |
| 5,221,534 | A | 6/1993 | Deslauriers et al. | |
| 5,278,201 | A | 1/1994 | Dunn et al. | |
| 5,278,202 | A | 1/1994 | Dunn et al. | |
| 5,340,849 | A | 8/1994 | Dunn et al. | |
| 5,548,035 | A | 8/1996 | Kim et al. | |
| 5,632,727 | A | 5/1997 | Tipton et al. | |
| 5,733,950 | A | 3/1998 | Dunn et al. | |
| 5,739,176 | A | 4/1998 | Dunn et al. | |
| 5,744,153 | A | 4/1998 | Yewey et al. | |
| 5,780,044 | A | 7/1998 | Yewey et al. | |
| 5,990,194 | A | 11/1999 | Dunn et al. | |
| 6,143,314 | A | 11/2000 | Chandrashekar et al. | |
| 6,206,920 | B1 | 3/2001 | Eliaz et al. | |
| 6,261,583 | B1 | 7/2001 | Dunn et al. | |
| 6,294,204 | B1 | 9/2001 | Rossling et al. | |
| 6,350,812 | B1 | 2/2002 | Vert et al. | |
| RE37,950 | E | 12/2002 | Dunn et al. | |
| 6,565,874 | B1 | 5/2003 | Dunn et al. | |
| 6,592,899 | B2 | 7/2003 | Fowers et al. | |
| 6,630,155 | B1 | 10/2003 | Chandrashekar et al. | |
| 6,773,714 | B2 | 8/2004 | Dunn et al. | |
| 6,916,788 | B2 | 7/2005 | Seo et al. | |
| 7,153,520 | B2 | 12/2006 | Seo et al. | |
| 7,160,551 | B2 | 1/2007 | McHugh et al. | |
| 7,649,023 | B2 * | 1/2010 | Shih et al. | 514/772.1 |
| 2005/0112170 | A1 | 5/2005 | Hossainy et al. | |
| 2007/0104759 | A1 | 5/2007 | Dunn et al. | |
| 2009/0004243 | A1 | 1/2009 | Pacetti et al. | |

FOREIGN PATENT DOCUMENTS

| | | |
|---|---|---|
| EP | 0 436 667 B1 | 4/1997 |
| EP | 1 244 471 | 6/2001 |
| EP | 1 125 577 A2 | 8/2001 |
| EP | 0 773 034 B1 | 12/2002 |
| EP | 1 126 822 B1 | 2/2004 |
| EP | 1 322 286 B1 | 5/2005 |
| EP | 1 586 309 A1 | 10/2005 |
| EP | 1 100 460 B1 | 4/2008 |
| EP | 1 339 389 B1 | 8/2008 |
| FR | 2 741 628 | 11/1995 |
| JP | 2010-215562 | 9/2010 |
| WO | WO 88/02625 | 4/1988 |
| WO | WO 95/03357 | 2/1995 |
| WO | WO 96/21427 | 7/1996 |
| WO | WO 01/45742 A1 | 6/2001 |
| WO | WO 2009/060473 A2 | 5/2009 |

OTHER PUBLICATIONS

Cerrai et al., "Block copolymers of L-lactide and poly(ethylene glycol) for biomedical applications", Journal of Materials Science: Materials in Medicine, vol. 5 (1994) pp. 308-313.

International Search Report issued in International Application No. PCT/IB2011/003323 on Aug. 9, 2012.

Li, "Bioresorbable Hydrogels Prepared Through Stereocomplexation between Poly (L-lactide) and Poly (D-lactide) Blocks Attracted to Poly(ethylene glycol)", Macromolecular Bioscience, vol. 3, No. 11 (2003) pp. 657-661.

English Machine Translation for CN-101507706-B dated Jul. 20, 2011.

* cited by examiner

*Primary Examiner* — Shobha Kantamneni

(74) *Attorney, Agent, or Firm* — Birch, Stewart, Kolasch & Birch, LLP

(57) ABSTRACT

A biodegradable drug delivery compositions comprising a triblock copolymer containing a polyester and a polyethylene glycol and a diblock copolymer containing a polyester and an end-capped polyethylene glycol, as well as a pharmaceutically active principle is disclosed.

18 Claims, 34 Drawing Sheets

BIODEGRADABLE DRUG DELIVERY COMPOSITIONS

This nonprovisional application claims the benefit of U.S. Provisional Application No. 61/428,007 filed on Dec. 29, 2010, which is hereby expressly incorporated by reference into the present application.

FIELD OF THE INVENTION

The present invention relates to biodegradable drug delivery compositions comprising a triblock copolymer containing a polyester and a polyethylene glycol and a diblock copolymer containing a polyester and an end-capped polyethylene glycol, as well as a pharmaceutically active principle. The ratio of triblock copolymer to diblock copolymer in this formulation is 1:3 to 1:8 or 1:1 to 1:19 or 3:2 to 1:19. Methods for producing these biodegradable drug compositions using organic solvents are also disclosed.

BACKGROUND OF THE PRESENT INVENTION

Drug delivery systems such as diblock and triblock copolymers have been used to deliver a variety of drugs and are generally formulated to deliver specific drugs whether they are hydrophobic drugs or hydrophilic drugs. Depending on the drug solubility these drug formulations differ in polymer concentrations, types of polymers utilized, molecular weights of the polymers and solvents used in the formulations.

Also the type of environment in which the drug is delivered is an important consideration in formulating a drug delivery system. Thus, there exist drug delivery compositions that are prepared using temperature sensitive polymers, phase sensitive polymers, pH sensitive polymers and photosensitive polymers. See, for example, K. Al-Tahami and J. Singh "Smart Polymer Based Delivery Systems for Peptide and Proteins," Recent Patents on Drug Delivery & Formulation, 1: pages: 65-71 Bentham Science Publishers, LTD. 2007.

U.S. Pat. No. 6,592,899 describes a PLA/PLGA oligomer combined with a block copolymer for enhancing the solubility of a hydrophobic drug into a hydrophilic environment. More specifically this polymer composition has a polyester oligomer having a molecular weight of between 400 and 10,000 daltons and a biodegradable AB-type, ABA-type or BAB type block copolymer. The hydrophobic A part is a polyester, while the hydrophilic B part is a polyethylene glycol having a molecular weight of between 2,400 and 4,999 daltons. This polymeric composition is soluble in an aqueous environment.

U.S. Pat. No. 6,541,033 describes a sustained release pharmaceutical composition based on thermosensitive, biodegradable hydrogels, consisting of a block copolymer of PLA or PLGA and PEG, for the sustained delivery of biologically active agents, such as leptin. The sustained release is for a period of a week or more and preferably up to one month.

Hydrogels containing triblock copolymers are described in U.S. Pat. No. 6,350,812. These hydrogels retain water weight at least equal to the water weight of the copolymer and are soft hydrogels.

None of the patents nor the literature cited above describes drug delivery compositions that are injectable, in situ forming and are biodegradable and turn into solid implants when injected into the body. The biodegradable drug compositions of the present invention comprise triblock copolymers and diblock copolymers formulated in such a manner that the diblock copolymer serves as a reservoir while the triblock copolymer acts as a frame in the formulations and increases the lifespan of the diblock copolymer.

Furthermore, the biodegradable drug delivery compositions of the present invention can be long acting formulations, which reduce the initial burst release of the drug and modulate the release rate of the drug over time. This phenomenon is illustrated in the flattening of the drug release curves.

SUMMARY OF THE INVENTION

The present invention provides a biodegradable drug delivery composition comprising (a) a biodegradable triblock copolymer having the formula:

$$A_v\text{-}B_w\text{-}A_x$$

wherein A is a polyester and B is polyethylene glycol and v, w and x are the number of repeat units ranging from 4 to 1090 and v=x or v≠x; (b) a biodegradable diblock copolymer having the formula:

$$C_y\text{-}A_z$$

wherein A is a polyester and C is an end-capped polyethylene glycol and y and z are the number of repeat units ranging from 3 to 237 or 7 to 371, wherein the ratio of the biodegradable triblock copolymer of (a) and the biodegradable CA diblock copolymer of (b) is 1:1 to 1:19 or 3:2 to 1:19 in said biodegradable drug composition; and (c) at least one pharmaceutically active principle.

The present invention provides a biodegradable drug delivery composition comprising (a) a biodegradable triblock copolymer having the formula:

$$A_v\text{-}B_w\text{-}A_x$$

wherein A is a polyester and B is polyethylene glycol and v, w and x are the number of repeat units ranging from 6 to 1090 and v=x or v≠x; (b) a biodegradable diblock copolymer having the formula:

$$C_y\text{-}A_z$$

wherein A is a polyester and C is an end-capped polyethylene glycol and y and z are the number of repeat units ranging from 7 to 371, wherein the ratio of the biodegradable triblock copolymer of (a) and the biodegradable CA diblock copolymer of (b) is 1:3 to 1:8 in said biodegradable drug composition; and (c) at least one pharmaceutically active principle.

The present invention provides a biodegradable drug delivery composition comprising (a) a biodegradable triblock copolymer having the formula:

$$A_v\text{-}B_w\text{-}A_x$$

wherein A is a polyester and B is polyethylene glycol and v, w and x are the number of repeat units ranging from 4 to 1090, v and x being ester repeat units and w being ethylene oxide repeat units and v=x or v≠x; (b) a biodegradable diblock copolymer having the formula:

$$C_y\text{-}A_z$$

wherein A is a polyester and C is an end-capped polyethylene glycol and y and z are the number of repeat units ranging from 3 to 237 or 7 to 371, y being the number of ethylene oxide repeat units and z the number of ester repeat units, wherein the ratio of the biodegradable triblock copolymer of (a) and the biodegradable CA diblock copolymer of (b) is 1:1 to 1:19 or 3:2 to 1:19 in said biodegradable drug composition; and (c) at least one pharmaceutically active principle.

The present invention provides a biodegradable drug delivery composition comprising (a) a biodegradable triblock copolymer having the formula:

$$A_v\text{-}B_w\text{-}A_x$$

wherein A is a polyester and B is polyethylene glycol and v, w and x are the number of repeat units ranging from 6 to 1090, v and x being ester repeat units and w being ethylene oxide repeat units and v=x or v≠x; (b) a biodegradable diblock copolymer having the formula:

$C_y$-$A_z$ wherein A is a polyester and C is an end-capped polyethylene glycol and y and z are the number of repeat units ranging from 7 to 371, y being the number of ethylene oxide repeat units and z the number of ester repeat units, wherein the ratio of the biodegradable triblock copolymer of (a) and the biodegradable CA diblock copolymer of (b) is 1:3 to 1:8 in said biodegradable drug composition; and (c) at least one pharmaceutically active principle.

A biodegradable drug delivery composition comprising: (a) a biodegradable triblock copolymer having the formula:

$PLA_v$-$PEG_w$-$PLA_x$ wherein v, w and x are the number of repeat units ranging from 4 to 1090 and v=x or v≠x; (b) a biodegradable diblock copolymer having the formula:

$PEG_y$-$PLA_z$ wherein y and z are the number of repeat units ranging from 3 to 237 or 3 to 371, wherein the ratio of the biodegradable triblock copolymer of (a) and the biodegradable diblock copolymer of (b) is 1:6 in said biodegradable drug composition and wherein the PEG in the diblock is end-capped; and (c) at least one pharmaceutically active principle.

A biodegradable drug delivery composition comprising: (a) a biodegradable triblock copolymer having the formula:

$PLA_v$-$PEG_w$-$PLA_x$ wherein v, w and x are the number of repeat units ranging from 6 to 1090 and v=x or v≠x; (b) a biodegradable diblock copolymer having the formula:

$PEG_y$-$PLA_z$ wherein y and z are the number of repeat units ranging from 7 to 371, wherein the ratio of the biodegradable triblock copolymer of (a) and the biodegradable diblock copolymer of (b) is 1:6 in said biodegradable drug composition and wherein the PEG in the diblock is end-capped; and (c) at least one pharmaceutically active principle.

In yet another aspect a biodegradable drug delivery composition is provided, which comprises: (a) a biodegradable triblock copolymer present in an amount of 2.0% to 45% (w %/w %) of the total composition having the formula:

$PLA_v$-$PEG_w$-$PLA_x$ wherein v, w and x are the number of repeat units ranging from 4 to 1090 or 6 to 1090 and v=x or v≠x; (b) a biodegradable diblock copolymer present in an amount of 8.0% to 50% (w %/w %) of the total composition having the formula:

$PEG_y$-$PLA_z$ wherein y and z are the number of repeat units ranging from 3 to 237, wherein the ratio f the biodegradable triblock copolymer of (a) and the biodegradable diblock copolymer of (b) is 1:4 or 3:2 to 1:19 or 1:1 to 1:19 in said biodegradable drug composition and wherein the PEG in the diblock is end capped and (c) at least one pharmaceutically active principle is present in an amount of 1% to 20% (w %/w %) of the total composition or the at least one pharmaceutically active principle is present in an amount of 1 to 200 mg/ml.

In yet another aspect a biodegradable drug delivery composition is provided, which comprises: (a) a biodegradable triblock copolymer present in an amount of 3.0% to 45% (w %/w %) of the total composition having the formula:

$PLA_v$-$PEG_w$-$PLA_x$ wherein v, w and x are the number of repeat units ranging from 6 to 1090 and v=x or v≠x; (b) a biodegradable diblock copolymer present in an amount of 8.0% to 50% (w %/w %) of the total composition having the formula:

$PEG_y$-$PLA_z$ wherein y and z are the number of repeat units ranging from 7 to 371, wherein the ratio of the biodegradable triblock copolymer of (a) and the biodegradable diblock copolymer of (b) is 1:4 in said biodegradable drug composition and wherein the PEG in the diblock is end capped and (c) at least one pharmaceutically active principle is present in an amount of 1% to 20% (w %/w %) of the total composition or the at least one pharmaceutically active principle is present in an amount of 1 to 200 mg/ml.

In another aspect a biodegradable drug delivery composition comprising: (a) a biodegradable triblock copolymer having the formula:

$PLA_v$-$PEG_w$-$PLA_x$ wherein v, w and x are the number of repeat units ranging from 4 to 1090 and v=x or v≠x; (b) a biodegradable diblock copolymer having the formula:

$mPEG_y$-$PLA_z$ wherein y and z are the number of repeat units ranging from 3 to 237, wherein the ratio of the biodegradable triblock copolymer of (a) and the biodegradable diblock copolymer of (b) is 1:1 to 1:19 or 3:2 to 1:19 in said biodegradable drug composition; and (c) at least one pharmaceutically active principle.

In another aspect a biodegradable drug delivery composition comprising: (a) a biodegradable triblock copolymer having the formula:

$PLA_v$-$PEG_w$-$PLA_x$ wherein v, w and x are the number of repeat units ranging from 6 to 1090 and v=x or v≠x; (b) a biodegradable diblock copolymer having the formula:

$mPEG_y$-$PLA_z$ wherein y and z are the number of repeat units ranging from 7 to 371, wherein the ratio of the biodegradable triblock copolymer of (a) and the biodegradable diblock copolymer of (b) is 1:6 in said biodegradable drug composition; and (c) at least one pharmaceutically active principle.

In another aspect a biodegradable drug delivery composition comprising: (a) a biodegradable triblock copolymer having the formula:

$PLA_v$-$PEG_w$-$PLA_x$ wherein v, w and x are the number of repeat units ranging from 4 to 1090 and v=x or v≠x; (b) a biodegradable diblock copolymer having the formula:

$mPEG_y$-$PLA_z$ wherein y and z are the number of repeat units ranging from 7 to 371 or 3 to 237, wherein the ratio of the biodegradable triblock copolymer of (a) and the biodegradable diblock copolymer of (b) is 1:4 in said biodegradable drug composition; and (c) at least one pharmaceutically active principle.

In another aspect a biodegradable drug delivery composition comprising: (a) a biodegradable triblock copolymer having the formula:

$PLA_v$-$PEG_w$-$PLA_z$ wherein v, w and x are the number of repeat units ranging from 6 to 1090 and v=x or v≠x; (b) a biodegradable diblock copolymer having the formula:

$$mPEG_y\text{-}PLA_z$$

wherein y and z are the number of repeat units ranging from 7 to 371, wherein the ratio of the biodegradable triblock copolymer of (a) and the biodegradable diblock copolymer of (b) is 1:4 in said biodegradable drug composition; and (c) at least one pharmaceutically active principle.

The biodegradable drug delivery compositions of the invention can have a lactic acid to ethylene oxide molar ratio in the composition of between 0.5 to 3.5 or 0.5 to 22.3 for the triblock copolymer and between 2 to 6 or 0.8 to 13 for the diblock copolymer.

In another aspect the biodegradable drug delivery compositions of the invention can have a lactic acid to ethylene oxide molar ratio in the composition of between 0.5 to 22.3 for the triblock copolymer and between 0.8 to 13 for the diblock copolymer.

In yet another aspect the biodegradable drug delivery compositions of the invention can have a lactic acid to ethylene oxide molar ratio in the composition of between 0.5 to 2.5 for the triblock copolymer and between 3 to 5 for the diblock copolymer.

In one aspect the biodegradable drug delivery composition is an injectable liquid that when it is inserted into the body of an animal or plant becomes a hardened implant.

In yet another aspect the biodegradable delivery drug composition can be used as a spatial formulation such that it can be applied onto or inside the body of an animal or plant. For example, it can be dispensed during surgery to treat a wound or inside a plant to treat a virus.

In another aspect the biodegradable drug composition is prepared as small solid particles, which are placed directly on the injured site of the body of an animal or plant.

In another aspect the biodegradable drug composition is in the form of a rod implant.

A method for preparing the biodegradable drug delivery composition of the invention, said method comprising: (i) dissolving in an organic solvent (a) a biodegradable ABA type block copolymer having the formula:

$$A_v\text{-}B_w\text{-}A_x$$

wherein A is a polyester and B is polyethylene glycol and v, w and x are the number of repeat units ranging from 6 to 1090 wherein v=x or v≠x; and (b) a biodegradable diblock copolymer having the formula:

$$C_y\text{-}A_z$$

wherein A is a polyester and C is an end-capped polyethylene glycol and y and z are the number of repeat units ranging from 7 to 371 in a ratio of 1:3 to 1:8 (a):(b) to form a polymer mixture; and (ii) adding at least one pharmaceutically active principle to said polymer mixture, is yet another aspect of the invention.

A method for preparing the biodegradable drug delivery composition of the invention, said method comprising: (i) dissolving in an organic solvent (a) a biodegradable ABA type block copolymer having the formula:

$$A_v\text{-}B_w\text{-}A_x$$

wherein A is a polyester and B is polyethylene glycol and v, w and x are the number of repeat units ranging from 4 to 1090, v and x being ester repeat units and w being ethylene oxide repeat units wherein v=x or v≠x; and (b) a biodegradable diblock copolymer having the formula:

$$C_y\text{-}A_z$$

wherein A is a polyester and C is an end-capped polyethylene glycol and y and z are the number of repeat units ranging from 3 to 237, y being the number of ethylene oxide repeat units and z the number of ester repeat units in a ratio of 1:1 to 1:19 or 3:2 to 1:19 (a):(b) to form a polymer mixture; and (ii) adding at least one pharmaceutically active principle to said polymer mixture, is yet another aspect of the invention.

Yet another aspect the present invention provides a method for preparing the biodegradable drug delivery composition of the present invention said method comprising: (i) dissolving in an organic solvent (a) a biodegradable ABA type block copolymer having the formula:

$$A_v\text{-}B_w\text{-}A_x$$

wherein A is a polyester and B is polyethylene glycol and v, w and x are the number of repeat units ranging from 6 to 1090 wherein v=x or v≠x; and (b) a biodegradable diblock copolymer having the formula:

$$C_y\text{-}A_z$$

wherein A is a polyester and C is an end-capped polyethylene glycol and y and z are the number of repeat units ranging from 7 to 371 in a ratio of 1:4 in (a):(b) to form a polymer mixture; (ii) adding at least one pharmaceutically active principle to said polymer mixture; and (iii) evaporating said solvent.

Yet another aspect the present invention provides a method for preparing the biodegradable drug delivery composition of the present invention said method comprising: (i) dissolving in an organic solvent (a) a biodegradable ABA type block copolymer having the formula:

$$A_v\text{-}B_w\text{-}A_x$$

wherein A is a polyester and B is polyethylene glycol and v, w and x are the number of repeat units ranging from 4 to 1090 wherein v=x or v≠x; and (b) a biodegradable diblock copolymer having the formula:

$$C_y\text{-}A_z$$

wherein A is a polyester and C is an end-capped polyethylene glycol and y and z are the number of repeat units ranging from 3 to 237 in a ratio of 1:1 to 1:19 or 3:2 to 1:19 (a):(b) to form a polymer mixture; (ii) adding at least one pharmaceutically active principle to said polymer mixture; and (iii) evaporating said solvent.

Yet another aspect the present invention provides a method for preparing the biodegradable drug delivery composition of the present invention said method comprising: (i) dissolving in an organic solvent (a) a biodegradable ABA type block copolymer having the formula:

$$A_v\text{-}B_w\text{-}A_x$$

wherein A is a polyester and B is polyethylene glycol and v, w and x are the number of repeat units ranging from 6 to 1090, v and x being ester repeat units and w being ethylene oxide repeat units wherein v=x or v≠x; and (b) a biodegradable diblock copolymer having the formula:

$$C_y\text{-}A_z$$

wherein A is a polyester and C is an end-capped polyethylene glycol and y and z are the number of repeat units ranging from 7 to 371, y being the number of ethylene oxide repeat units and z the number of ester repeat units, in a ratio of 1:4 (a):b)

to form a polymer mixture; (ii) adding at least one pharmaceutically active principle to said polymer mixture; and (iii) evaporating said solvent.

Yet another aspect the present invention provides a method for preparing the biodegradable drug delivery composition of the present invention said method comprising: (i) dissolving in an organic solvent (a) a biodegradable ABA type block copolymer having the formula:

$$A_v\text{-}B_w\text{-}A_x$$

wherein A is a polyester and B is polyethylene glycol and v, w and x are the number of repeat units ranging from 4 to 1090, v and x being ester repeat units and w being ethylene oxide repeat units wherein v=x or v≠x; and (b) a biodegradable diblock copolymer having the formula:

$$C_y\text{-}A_z$$

wherein A is a polyester and C is an end-capped polyethylene glycol and y and z are the number of repeat units ranging from 3 to 237, y being the number of ethylene oxide repeat units and z the number of ester repeat units, in a ratio of 1:4 (a):(b) to form a polymer mixture; (ii) adding at least one pharmaceutically active principle to said polymer mixture; and (iii) evaporating said solvent.

In the above methods the organic solvent can be present in an amount of 40% to 74% (w %/w %) of the total composition. Mixtures of solvents can also be used.

Other aspects and embodiments are set forth below, or will readily arise from the following description of the preferred embodiments.

DESCRIPTION OF THE PREFERRED EMBODIMENTS

Figure 1:
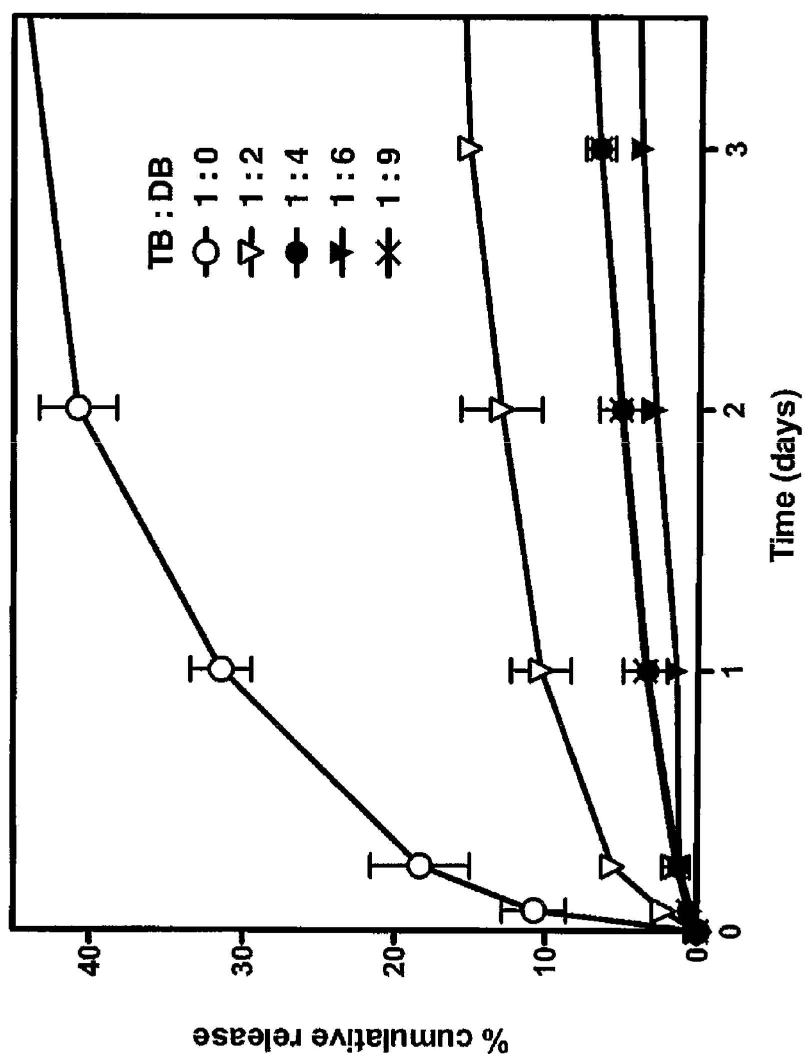
FIG. 1 is a graph showing the in vitro release rate of the drug from formulations based on 40% P6R1(TB):dP2R4 (DB) in ratios of 1:0 (-○-), 1:2 (-Δ-), 1:4 (-●-), 1:6 (-▼-) and 1:9 (-*-) over time in days. This graph shows that formulations based on TB:DB are sustaining the release for more than 30 days.
Figure 2:
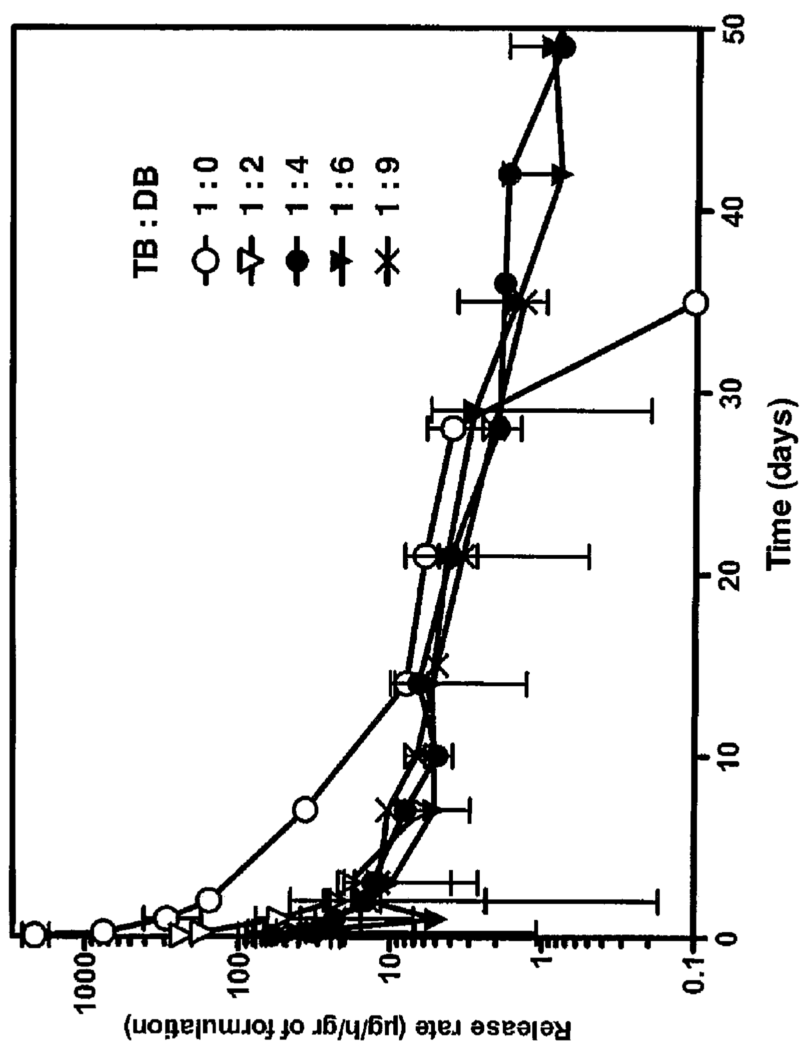
FIG. 2 is a graph showing the in vitro cumulative percent release curve from candidate formulations of FIG. 1 over time (days). This graph illustrates that the initial burst is reduced and the drug release curve is flattened in the combination of triblock copolymer and diblock copolymer compositions compared to the triblock copolymer composition alone. It should be noted that the 1:9 curve is overlapping the 1:4 curve.

As used herein the term "biodegradable" means that the triblock and diblock copolymers will after a period of time erode or degrade in vivo to form smaller non-toxic components.

The term "parental administration" encompasses intramuscular, intraperitoneal, intra-abdominal, subcutaneous, intravenous and intraarterial. It also encompasses intradermal, intracavernous, intravitreal, intracerebral, intrathecal, epidurall and intraosseous administration.

The term "animals" encompasses all members of the Kingdom Animalia.

As used herein the term "plant" encompasses all members of the Plant Kingdom.

"Active principle" means a drug or medicine for treating various medical illnesses. Thus active principles, drugs and medicines are used interchangeably. The term drug or active principle as used herein includes without limitation physiologically or pharmacologically active substances that act locally or systemically in the body of an animal or plant. At least one active principle is present in the biodegradable drug composition of the invention.

As used herein "disease" means any disorder in a human, animal or plant caused by infection, diet, or by faulty functioning of a process.

The term "implant" means that the drug delivery compositions are injectable, are in situ forming and are biodegradable and turn into solid implants when injected into the body. Thus, that the formulations that are synthesized are liquids such that they can be easily injected through a syringe without excessive force.

The term "spatial formulations" encompass any formulations that can be applied on or into the animal or plant body and do not necessarily have to be administered through a syringe.

As used herein "repeat units" are the fundamental recurring units of a polymer.

By "end-capped polyethylene glycol" (cPEG) refers to PEG's in which one terminal hydroxyl group is reacted and includes alkoxy-capped PEG's, urethane-capped PEG's ester-capped PEG's and like compounds. The capping group is a chemical group which does not contain a chemical function susceptible to react with cyclic esters like lactide, glycolactide, caprolactone and the like or other esters and mixtures thereof. The reaction of an end-capped PEG polymer with lactide generates a diblock cPEG-PLA copolymer.

As used herein polyethylene glycol, as abbreviated PEG throughout the application, is sometimes referred to as poly(ethylene oxide) or poly(oxyethylene) and the terms are used interchangeably in the present invention.

The abbreviation of "PLA" refers to poly(lactic acid).

The abbreviation of "PLGA" refers to poly(lactic-co-glycolic acid).

The abbreviation "T" or "TB" refers to a triblock copolymer(s), while the abbreviation "D" or "DB" refers to a diblock copolymer(s).

The term "diblock" as used herein refers, for example, to an end-capped PEG-polyester copolymer. "mPEG" refers to methoxy polyethylene glycol.

The term "triblock" refers, for example, to a polyester-PEG-polyester copolymer.

The LA/EO ratio refers to the molar ratio of lactic acid units to ethylene oxide units that is present in the biodegradable drug delivery composition. It is determined experimentally by NMR. The LA/EO molar ratio of the combined triblock copolymer can range from 0.5 to 3.5. In another aspect the LA/EO molar ratio in the triblock can range from 0.5 to 2.5 in the biodegradable drug delivery composition described herein. In yet another aspect the LA/EO ratio in the triblock can range from 0.5 to 22.3.

The LA/EO ratio in the diblock can range from 2 to 6. In another aspect the LA/EO ratio in the diblock can range from 3 to 5 in the biodegradable drug delivery composition. In another aspect the LA/EO ratio in the diblock can range from 0.8 to 13.

The degree of polymerization or DP is the number of repeat units in an average polymer chain at time t in a polymerization reaction. For example, the degree of polymerization for PEG is about 45 to 170 or it can be 4 to 273 or 3 to 45, while for PLA it can range from about 84 to 327 or it can be 24 to 682 or 7 to 327.

The present invention thus relates to a biodegradable drug composition comprising a triblock copolymer and a diblock copolymer. The biodegradable triblock copolymer has the formula: $A_v$-$B_w$-$A_x$, wherein A is a polyester and B is polyethylene glycol and v, w and x are the number of repeat units ranging, for example, from 4 to 1090 or from 6 to 1090 and v=x or v≠x. w is the degree of polymerization (number of repeat units) for PEG. The degree of polymerization for DP-PEG is calculated by dividing the PEG molecular weight by the EO unit molecular weight (44 Da). v+x equals the degree of polymerization (number of repeat units) for PLA. DP-PLA is calculated by multiplying DP-PEG by the LA/EO ratio.

However the number of repeat units of v, w and x in the triblock composition may vary due to the targeted time of release of the active principle and the type of active principle itself. Therefore the number of repeat units in the triblock of v, w and x can range from 8 to 1090, from 10 to 850, from 20 to 700, from 30 to 650 and v=x or v≠x. For instance, w can be 273, while x+y can be 682 and v=x or v≠x or w can be 136 and x+y can be 273 and v=x or v≠x or w can be 45.5 and x+y can be 546 or w can be 273 and x+y can be 136.

The size of the PEG in the triblock can range from 194 Da to 12,000 Da.

The polyester in the triblock can be polylactic acid (PLA), polycaprolactone (PCL), polyglycolic acid (PGA) or polyhydroxyalkanoate (PHA). In one embodiment the polyester that is used is polylactic acid.

The triblock copolymer is then combined with a biodegradable diblock copolymer having the formula: $C_y$-$A_z$, wherein A is a polyester and C is an end-capped polyethylene glycol and y and z are the number of repeat units ranging from 7 to 371 or from 3 to 327. This combination has a ratio of triblock copolymer to diblock copolymer ranging from 1:3 to 1:8 or 1:1 to 1:19 or 3:2 to 1:19.

Examples of end-capped polyethylene glycols include alkoxy capped PEG's such as methoxyPEG or ethoxyPEG, urethane-capped PEG's, ester-capped PEG's, amine-capped PEG's and amide-capped PEG's. This list of end-capped PEG's is not exhaustive and a person skilled in the art would recognize additional end-capped PEG's, which are not listed.

However the number of repeat units (degree of polymerization (DP)) of y and z in the diblock composition may also vary. Thus, y can, for example, range from 7 to 43 or 3 to 45 and z can range from 32 to 123 or 7 to 327. For example, y can be 25 and z can be 123, y can be 34.5 and z can be 123 or y can be 45 and z can be 32. The degree of polymerization for DP-PEG is calculated by dividing the PEG molecular weight of the capped PEG by the EO unit molecular weight (44 Da). The DP-PLA is calculated by multiplying DP-PEG by the LA/EO ratio, The polyester in the diblock can be polylactic acid (PLA), polycaprolactone (PCL), polyglycolic acid (PGA), poly(lactic-co-glycolic acid) (PLGA) or polyhydroxyalkanoate (PHA). In one embodiment the polyester that is used is polylactic acid. In another embodiment the polyester is poly(lactic-co-glycolic acid).

In another aspect the present invention provides a biodegradable drug delivery composition comprising (a) a biodegradable triblock copolymer having the formula:

$$A_v\text{-}B_w\text{-}A_x$$

wherein A is a polyester and B is polyethylene glycol and v, w and x the number of are repeat units ranging from 4 to 1090 or from 6 to 1090, v and x being ester repeat units and w being ethylene oxide repeat units and v=x or v≠x; (b) a biodegradable diblock copolymer having the formula:

$$C_y\text{-}A_z$$

wherein A is a polyester and C is an end-capped polyethylene glycol and y and z are the number of repeat units ranging from 7 to 371 or 3 to 237, y being the number of ethylene oxide repeat units and z the number of ester repeat units, wherein the ratio of the biodegradable triblock copolymer of (a) and the biodegradable CA diblock copolymer of (b) is 1:3 to 1:8 or 1:1 to 1:19 or 3:2 to 1:19 in said biodegradable drug composition; and (c) at least one pharmaceutically active principle.

In another aspect the present invention provides a biodegradable drug delivery composition comprising a biodegradable triblock copolymer having the formula: $PLA_v$-$PEG_w$-$PLA_x$, wherein v, w and x are the number of repeat units ranging from 4 to 1090 or 6 to 1090 and v=x or v≠x; a biodegradable diblock copolymer having the formula: $mPEG_y$-$PLA_z$, wherein y and z are the number of repeat units ranging from 7 to 371 or 3 to 327, wherein the ratio of the biodegradable triblock copolymer and the biodegradable diblock copolymer is 1:6 in said biodegradable drug composition; and at least one pharmaceutically active principle.

In another aspect a biodegradable drug delivery composition comprising: (a) a biodegradable triblock copolymer having the formula:

$$PLA_v\text{-}PEG_w\text{-}PLA_x$$

wherein v, w and x are the number of repeat units ranging from 4 to 1090 or 6 to 1090 and v=x or v≠x; (b) a biodegradable diblock copolymer having the formula:

$$mPEG_y\text{-}PLA_z$$

wherein y and z are the number of repeat units ranging from 7 to 371 or 3 to 237, wherein the ratio of the biodegradable triblock copolymer of (a) and the biodegradable diblock copolymer of (b) is 1:4 in said biodegradable drug composition; and (c) at least one pharmaceutically active principle.

The ratio of the biodegradable triblock copolymer of (a) and the biodegradable CA diblock copolymer of (b) is 1:3 to 1:8 or 1:1 to 1:19 or 3:2 to 1:19 in said biodegradable drug composition. In one embodiment the ratio of the biodegradable triblock copolymer of and the biodegradable CA diblock copolymer is selected from the group of 1:3, 1:4, 1:5, 1:6, 1:7 and 1:8 or 1:1, 1:2, 1:3, 1:4, 1:5, 1:6, 1:7, 1:8, 1:9, 1:10, 1:11, 1:12, 1:13, 1:14, 1:15, 1:16, 1:17, 1:18 and 1:19. It can also be 3:2. In another aspect the ratio of the triblock to the diblock is 1:6.

The length of the polyester chain is defined by its polyester to ethylene oxide molar ratio, which is between 0.5 to 3.5 or 0.5 to 2.5 or 0.5 to 22.3 for the triblock copolymer and 3 to 5 or 2 to 6 or 0.8 to 13 for the diblock copolymer. Thus, for example, if polylactic acid is used the chain length is defined by the lactic acid/ethylene oxide molar ratio. Similarly if polyglycolic acid is used, the chain length is defined by the polyglycolic acid/ethylene oxide molar ratio or the polycaprolactone/ethylene oxide molar ratio or the olyhydroxyalkanoate/ethylene oxide molar ratio. If poly(lactic-co-glycolic) acid is used the chain length is defined by the ratio of LA+G/EO.

The mass of the end-capped polyethylene glycol can range from 164 Da to 2,000 Da or from 100 Da to 2 kDa. It can range in the lower 100 to 300 Da range or in the 1 kDa to 2 kDa range.

The size of the polyethylene glycol chain ranges from 200 Da to 12 kDa in the biodegradable drug delivery composition or it can range from 400 Da to 12 kDa or 194 Da to 12 kDA.

The polymers are present in an amount of 20% to 50% (w %/w %) of the total weight of the composition. In another aspect the total weight of the polymers present in the biodegradable drug composition is 30% to 50% (w %/w %) of the total weight of the composition. In yet another aspect the polymers are present in the biodegradable drug composition at 40% to 50% (w %/w %) of the total weight of the composition.

Thus, the triblock copolymer is present in an amount of 3.0% to 45% (w %/w %) of the total weight of the composition. In another aspect the triblock copolymer is present in an amount of 6% to 10% (w %/w %) of the total weight of the composition. In yet another aspect the triblock copolymer is present in an amount of 20% to 40% (w %/w %) of the total weight of the composition.

Likewise the diblock copolymer can be present in the biodegradable drug composition in an amount of 8% to 50% (w %/w %) of the total weight of the composition. In another aspect the diblock copolymer is present in an amount of 10% to 20% (w %/w %) of the total weight of the composition. In yet another aspect the diblock copolymer is present in an amount of 20% to 40% (w %/w %) of the total weight of the composition.

The at least one pharmaceutically active principle is entrapped in the triblock:diblock biodegradable drug delivery composition. Representative drugs and biologically active agents to be used in the invention include, without limitation, peptide drugs, protein drugs, desensitizing agents, antigens, vaccines, vaccine antigens, anti-infectives, antibiotics, antimicrobials, antiallergenics, anti-diabetics, steroidal anti-inflammatory agents, decongestants, miotics, anticholinergics, sympathomimetics, sedatives, hypnotics, psychic energizers, tranquilizers, androgenic steroids, estrogens, progestational agents, humoral agents, prostaglandins, analgesics, corticosteroids, antispasmodics, antimalarials, antihistamines, cardioactive agents, non-steroidal anti-inflammatory agents, antiparkinsonian agents, antihypertensive agents, beta-adrenergic blocking agents, nutritional agents, gonadotrophin releasing hormone agonists, insecticides, anti-helminthic agents and the benzophenanthridine alkaloids.

Thus combinations of drugs can also be used in the biodegradable drug delivery composition of this invention. For instance, if one needs to treat Lupus erythematosis, non-steroidal anti-inflammatory agents and corticosteroids can be administered together in the present invention.

Veterinary medicaments such as medicines for the treatment of worms or vaccines for animals are also part of the present invention.

Viral medicaments for plants such as those viruses from Potyviridae, Geminiviridae, the Tospovirus genus of Bunyaviridiae and Banana streak virus are also encompassed by the present invention. Also medicaments for tobacco mosaic virus, turnip crinkle, barley yellow dwarf, ring spot watermelon and cucumber mosaic virus can be used in the biodegradable drug delivery composition of the invention.

To those skilled in the art, other drugs or biologically active agents that can be released in an aqueous environment can be utilized in the described delivery system. Also, various forms of the drugs or biologically active agents may be used. These include without limitation forms such as uncharged molecules, molecular complexes, salts, ethers, esters, amides, etc., which are biologically activated when injected into the animal or plant or used as a spatial formulation such that it can be applied on or inside the body of an animal or plant or as a rod implant.

The pharmaceutically effective amount of an active principle may vary depending on the active principle, the extent of the animal's or plants medical condition and the time required to deliver the active principle. There is no critical upper limit on the amount of active principle incorporated into the polymer solution except for that of an acceptable solution or dispersion viscosity for injection through a syringe needle and that it can effectively treat the medical condition without subjecting the animal or plant to an overdose. The lower limit of the active principle incorporated into the delivery system is dependent simply upon the activity of the active principle and the length of time needed for treatment.

For instance some active principles may be present in the biodegradable drug delivery composition from 10 to 200 mg/ml. In another aspect the drugs should be present in the amount of 10 to 40 μg/ml. For a small molecule, for instance, the active principle can be loaded as high as 100 to 200 mg per ml.

Generally the pharmaceutically active principle is present in an amount of 1% to 20% (w %/w %) of the total weight of the composition. In another aspect the active principle is present in 1% to 4% (w %/w %) of the total weight of the composition. In another aspect the active principle is present in 2% to 4% (w %/w %) of the total weight of the composition. In yet another aspect the active principle, which is a small molecule, is present in an amount of 10% to 20% (w %/w %) of the total weight of the composition.

In the biodegradable drug delivery composition of the present invention, the pharmaceutically effective amount can be released gradually over an extended period of time. This slow release can be continuous or discontinuous, linear or non-linear and can vary due to the composition of the triblock copolymer and diblock copolymer. Thus, the higher the lactic acid content of the triblock and diblock copolymers in comparison with the polyethylene glycol content, as well as the amount of triblock and diblock copolymers present in the biodegradable drug composition the longer the release of the active principle or drug. In other words, the higher the LA/EO molar ratio and the greater weight percentage of the triblock and diblock copolymers, the longer it will take for the active principle to be released from the drug composition.

The active principle can be released for a duration of between 7 days to 1 year or longer depending upon the type of treatment needed and the biodegradable drug delivery composition used. In one aspect the biodegradable drug delivery composition can deliver the active principle for at least 7 days. In another aspect the biodegradable drug delivery composition can deliver the active principle for at least 30 days. In one aspect the biodegradable drug delivery composition can deliver the active principle for at least 90 days. In yet another aspect the biodegradable drug delivery composition can deliver an active principle for 1 year or longer.

The biodegradable drug delivery composition can be an injectable liquid at room temperature and be injected through a syringe without excessive force. But these biodegradable drug delivery compositions are also in situ forming and biodegradable and turn into solid implants when injected into the animal or plant. Alternatively the biodegradable drug composition is produced as a solid, prepared as small particles and used as a powder which is sprinkled on the injured site. In another aspect the drug delivery composition is a rod implant, which can be implanted under the skin or in another compartment in the body. In another aspect the drug delivery composition can be prepared and applied as a film. In yet another aspect the biodegradable delivery drug composition can be used as a spatial formulation such that it can be applied onto or inside the body of an animal or plant. It can be applied anywhere on the body, including in the eye.

The biodegradable drug delivery composition can further comprise a pharmaceutically acceptable carrier, adjuvant or vehicle. An acceptable carrier can be saline, buffered saline and the like. It can be added to the biodegradable drug delivery composition after its formulation with the drug and diblock copolymer and triblock copolymer.

The adjuvant can be formulated simultaneously when mixing the drug. In this regard the adjuvants that can be used are alum, aluminum phosphate, calcium phosphate, MPL™, CpG motifs, modified toxins, saponins, endogenous stimulatory adjuvants such as cytokines, Freunds complete and incomplete adjuvants, ISCOM type adjuvants, muramyl peptides and the like.

The vehicle can be any diluent, additional solvent, filler or binder that may alter the delivery of the active principle when needed in the biodegradable drug delivery composition. Examples include small amounts of triglycerides such as triacetin or tripropionin. The amount that can be used in the present biodegradable drug deliver compositions of the present invention can vary from 12% to 20% (w %/w %). In one aspect a triacetin can be added in the formulation at 17.0% (w %/w %). In another aspect tripropionin (abbreviated herein as Tripro) can be added at 16% (w %/w %).

A method for preparing the biodegradable drug delivery composition of the invention is also encompassed by the invention. This method comprises: (i) dissolving in an organic solvent (a) a biodegradable ABA type block copolymer having the formula: $A_v$-$B_w$-$A_x$, wherein A is a polyester and B is polyethylene glycol and v, w and x are the number of repeat units ranging from 4 to 1090 or 6 to 1090; and (b) a biodegradable diblock copolymer having the formula: $C_y$-$A_z$, wherein A is a polyester and C is an end-capped polyethylene glycol and y and z are the number of repeat units ranging from 7 to 371 or 3 to 237 in a ratio of 1:3 to 1:8 or 1:1 to 1:19 or 3.2 to 1:19 triblock to diblock to form a polymer mixture; and adding at least one pharmaceutically active principle to said polymer mixture.

A method for preparing the biodegradable drug delivery composition of the invention, said method comprising: (i) dissolving in an organic solvent (a) a biodegradable ABA type block copolymer having the formula:

$$A_v\text{-}B_w\text{-}A_x$$

wherein A is a polyester and B is polyethylene glycol and v, w and x are the number of repeat units ranging from 4 to 1090 or 6 to 1090, v and x being ester repeat units and w being ethylene oxide repeat units wherein v=x or v≠x; and (b) a biodegradable diblock copolymer having the formula:

$$C_y\text{-}A_z$$

wherein A is a polyester and C is an end-capped polyethylene glycol and y and z are the number of repeat units ranging from 7 to 371 or 3 to 237, y being the number of ethylene oxide repeat units and z the number of ester repeat units, in a ratio of 1:3 to 1:8 or 1:1 to 1:19 or 3:2 to 1:19 (a):(b) to form a polymer mixture; and (ii) adding at least one pharmaceutically active principle to said polymer mixture, is yet another aspect of the invention.

Yet another aspect the present invention provides a method for preparing the biodegradable drug delivery composition of the present invention said method comprising: (i) dissolving in an organic solvent (a) a biodegradable ABA type block copolymer having the formula:

$$A_v\text{-}B_w\text{-}A_x$$

wherein A is a polyester and B is polyethylene glycol and v, w and x are the number of repeat units ranging from 4 to 1090 or 6 to 1090 wherein v=x or v≠x; and (b) a biodegradable diblock copolymer having the formula:

$$C_y\text{-}A_z$$

wherein A is a polyester and C is an end-capped polyethylene glycol and y and z are the number of repeat units ranging from 7 to 371 or 3 to 137 in a ratio of 1:4 (a):b) to form a polymer mixture; (ii) adding at least one pharmaceutically active principle to said polymer mixture; and (iii) evaporating said solvent.

Yet another aspect the present invention provides a method for preparing the biodegradable drug delivery composition of the present invention said method comprising: (i) dissolving in an organic solvent (a) a biodegradable ABA type block copolymer having the formula:

$$A_v\text{-}B_w\text{-}A_x$$

wherein A is a polyester and B is polyethylene glycol and v, w and x are the number of repeat units ranging from 6 to 1090, v and x being ester repeat units and w being ethylene oxide repeat units wherein v=x or v≠x; and (b) a biodegradable diblock copolymer having the formula:

$$C_y\text{-}A_z$$

wherein A is a polyester and C is an end-capped polyethylene glycol and y and z are the number of repeat units ranging from 7 to 371 or 3 to 237, y being the number of ethylene oxide repeat units and z the number of ester repeat units, in a ratio of 1:4 (a):b) to form a polymer mixture; (ii) adding at least one pharmaceutically active principle to said polymer mixture; and (iii) evaporating said solvent.

Another embodiment provides a method for preparing the biodegradable drug delivery composition of the invention, said method comprising: (i) dissolving in an organic solvent (a) a biodegradable ABA type block copolymer having the formula: $A_v$-$B_w$-$A_x$, wherein A is a polyester and B is polyethylene glycol and v, w and x are the number of repeat units ranging from 4 to 1090 or 6 to 1090; and (b) a biodegradable diblock copolymer having the formula: $C_y$-$A_z$, wherein A is a polyester and C is an end-capped polyethylene glycol and y and z are the number of repeat units ranging from 7 to 371 or 3 to 237 in a ratio of 1:6 triblock to diblock to form a polymer mixture; adding at least one pharmaceutically active principle to said polymer mixture; and evaporating said solvent. In this aspect no solvent is present in the biodegradable drug delivery composition.

The organic solvent that can be used in the method described herein is selected from the group of: benzyl alcohol, benzyl benzoate, diethylene glycol dimethyl ether (Diglyme), diethylene glycol monoethyl ether (DEGMEE), dimethyl isosorbide (DMI), dimethyl sulfoxide (DMSO), ethyl acetate, ethyl benzoate, ethyl lactate, ethylene glycol monoethyl ether acetate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin (tripro), or triethylene glycol dimethyl ether (triglyme) and mixtures thereof.

The organic solvent is present in an amount of 40% to 74% (w %/w %) of the total composition. In another aspect the organic solvent used in the preparation of the biodegradable drug delivery composition is present in an amount of 50% to 60% (w %/w %) of the total composition. In yet another aspect the solvent used in the preparation of the biodegradable drug delivery composition is present in an amount of 60% to 70% (w %/w %) of the total composition.

Some mPEG-OH are contaminated with a small amount of OH-PEG-OH. By following the methods of the present invention and using the contaminated mPEG-OH the final product would be mPEG-PLA contaminated with a small amount of PLA-PEG-PLA, which is encompassed by the present invention.

Another aspect of the present invention is the use of diblock and triblock copolymers for the manufacture of a biodegradable drug composition. In this respect the biodegradable triblock copolymer has the formula: $A_v$-$B_w$-$A_x$, wherein A is a polyester and B is polyethylene glycol and v, w and x are the number of repeat units ranging from 4 to 1090 or 6 to 1090 and v=x or v≠x. The polyester can be polylactic acid (PLA), polycaprolactone (PCL), polyglycolic acid (PGA) or polyhydroxyalkanoate (PHA). In one embodiment the polyester that is used is poly(lactic) acid.

The triblock copolymer is then combined with a biodegradable diblock copolymer having the formula: $C_{y\text{-}Az}$ wherein A is a polyester and C is an end-capped polyethylene glycol and y and z are the number of repeat units ranging from 7 to 371 or 3 to 237. The polyester can be polylactic acid (PLA), polycaprolactone (PCL), polyethylene adipate (PEA) polyglycolic acid (PGA), poly(lactic-co-glycolic acid (PLGA) or polyhydroxyalkanoate (PHA). In one embodiment the polyester that is used is poly(lactic) acid.

The ratio of the biodegradable triblock copolymer of (a) and the biodegradable CA diblock copolymer of (b) is 1:3 to 1:8 in said biodegradable drug composition. In one embodiment the ratio of the biodegradable triblock copolymer of and the biodegradable CA diblock copolymer is selected from the group of 1:3, 1:4, 1;5, 1:6, 1:7 and 1:8. or 1:1, 1:2, 1:3, 1:4, 1:5, 1:6, 1:7, 1:8, 1:9, 1:10, 1:11, 1:12, 1:13, 1:14, 1:15, 1:16, 1:17, 1:18 and 1:19. In another aspect the ratio of the triblock to the diblock is 1:6. It can also be 3:2.

The length of the polyester chain is defined by its polyester to ethylene oxide molar ratio, which is between 0.5 to 3.5 or 0.5 to 2.5 or 0.5 to 22.3 for the triblock and 3 to 5 or 2 to 6 or 0.8 to 13 for the diblock.

The mass of the end-capped polyethylene glycol can range from 100 Da to 2 kDa or 164 Da to 2 kDa. It can range in the 100 to 300 Da range or in the 1 kDa to 2 kDa range.

The size of the polyethylene glycol chain ranges from 200 Da to 12 kDa in the biodegradable drug delivery composition or it can range from 400 Da to 12 kDa or 194 Da to 12 kDa.

A number of embodiments and/or aspects of the invention have been described. Nevertheless it will be understood that various modifications may be made without departing from the spirit and scope of the invention.

EXAMPLES

Example 1

Polymer Synthesis

Copolymers were synthesized according to the method described in the U.S. Pat. No. 6,350,812, incorporated herein by reference, with minor modifications. Typically, the necessary amount of PEG (gives the triblock coploymer) or methoxy-PEG (gives the diblock copolymer) was heated at 65° C. and dried under vacuum for 2 hours in a reactor vessel. DL-lactide (corresponding to the targeted LA/EO molar ratio) and zinc lactate (1/1000 of amount of lactide) were added. The reaction mixture was first dehydrated by three short vacuum/N2 cycles. The reaction mixture was heated at 140° C. and rapidly degassed under vacuum. The reaction was conducted for four days at 140° C. under constant nitrogen flow (0.2 bar). The reaction was cooled to room temperature and its content was dissolved in acetone and then subjected to precipitation with ethanol. The product obtained was subsequently dried under reduced pressure. The final product was characterized by $^1$H NMR for its lactate content. The triblock PLA-PEG-PLA polymers described herein were labeled PxRy where x represent the size of the PEG chain in kDa and y is the LA/EO molar ratio. The diblock mPEG-PLA polymers described herein were labeled dPxRy where x represent the size of the PEG chain in kDa and y is the LA/EO molar ratio.

Example 2

Formulation Preparation Specific for the Peptide M53

The formulations described herein were based on organic solution of polymers containing as the drug, the peptide M53, a GLP-1 analogue. Typically, 0.4 grams of polymers, corresponding to a mix of a diblock copolymer and a triblock copolymer in defined mass ratio, were dissolved in 0.57 grams of a biocompatible solvent at room temperature overnight under constant magnetic stirring. The solvent was either a single solvent or a combination of solvents. The next day, 20 mg of drug was added to the polymer solution and stirred until complete dissolution. When the drug was not soluble in the solvent, a suspension of the drug in a polymer solution was obtained. Alternatively, the drug was dissolved or suspended in the biocompatible solvent and the polymer(s) added subsequently. The formulations were loaded in a syringe before use.

Example 3

The Formulations that were Prepared

Following Examples 1 and 2 Various Formulations were Prepared, which are Set Forth in Table 1 for the Peptide M53

TABLE 1

| | | M53 | Triblock copolymer (TB) | | PEG | | | | Diblock copolymer (DB) | |
|---|---|---|---|---|---|---|---|---|---|---|
| N° | Ratio DB/TB | % (w/w) | % (w/w) | Code | size (kDa) | Ratio (LA/EO) | DP-PEG | DP-PLA | % (w/w) | Code |
| 10 | 4.0 | 4.0 | 10.0% | P12R0.5 | 12 | 0.5 | 273 | 136 | 40.0% | dP2R3 |
| 12 | 4.0 | 4.0 | 10.0% | P12R3 | 12 | 2.5 | 273 | 682 | 40.0% | dP2R3 |
| 21 | 4.0 | 4.0 | 10.0% | P12R0.5 | 12 | 0.5 | 273 | 136 | 40.0% | dP2R3 |
| 23 | 4.0 | 4.0 | 10.0% | P12R3 | 12 | 2.5 | 273 | 682 | 40.0% | dP2R3 |
| 34 | 4.0 | 4.0 | 10.0% | P12R0.5 | 12 | 0.5 | 273 | 136 | 40.0% | dP2R3 |
| 45 | 4.0 | 4.0 | 10.0% | P12R3 | 12 | 2.5 | 273 | 682 | 40.0% | dP2R3 |
| 66 | 4.0 | 4.0 | 10.0% | P12R0.5 | 12 | 0.5 | 273 | 136 | 40.0% | dP2R3 |
| 68 | 4.0 | 4.0 | 10.0% | P12R3 | 12 | 2.5 | 273 | 682 | 40.0% | dP2R3 |
| 76 | 4.0 | 4.0 | 10.0% | P12R0.5 | 12 | 0.5 | 273 | 136 | 40.0% | dP2R3 |
| 78 | 4.0 | 4.0 | 10.0% | P12R3 | 12 | 2.5 | 273 | 682 | 40.0% | dP2R3 |
| 80 | 4.0 | 4.0 | 10.0% | P12R0.5 | 12 | 0.5 | 273 | 136 | 40.0% | dP2R3 |
| 82 | 4.0 | 4.0 | 10.0% | P12R3 | 12 | 2.5 | 273 | 682 | 40.0% | dP2R3 |
| 105 | 4.0 | 4.0 | 8.0% | P6R0.9 | 6 | 0.9 | 136 | 123 | 32.0% | dP2R4 |
| 116 | 4.0 | 4.0 | 8.0% | P6R0.9 | 6 | 0.9 | 136 | 123 | 32.0% | dP2R4 |
| 123 | 4.0 | 4.0 | 8.0% | P3R1 | 3 | 1.0 | 68 | 68 | 32.0% | dP2R4 |
| 124 | 4.0 | 4.0 | 8.0% | P6R0.9 | 6 | 0.9 | 136 | 123 | 32.0% | dP2R4 |
| 153 | 4.0 | 4.0 | 7.0% | P12R0.5 | 12 | 0.5 | 273 | 136 | 28.0% | dP2R4 |
| 159 | 4.0 | 4.0 | 7.0% | P12R0.5 | 12 | 0.5 | 273 | 136 | 28.0% | dP2R4 |
| 169 | 5.7 | 2.0 | 6.0% | P6R0.9 | 6 | 0.9 | 136 | 123 | 34.0% | dP2R4 |
| 177 | 5.7 | 2.0 | 7.5% | P6R0.9 | 6 | 0.9 | 136 | 123 | 42.5% | dP2R4 |
| 198 | 9.0 | 4.0 | 4.0% | P6R0.9 | 6 | 0.9 | 136 | 123 | 36.0% | dP2R4 |
| 200 | 9.0 | 2.0 | 5.0% | P6R0.9 | 6 | 0.9 | 136 | 123 | 45.0% | dP2R3 |
| 203 | 4.0 | 2.0 | 10.0% | P6R0.9 | 6 | 0.9 | 136 | 123 | 40.0% | dP2R7 |
| 207 | 5.7 | 4.0 | 6.0% | P6R0.9 | 6 | 0.9 | 136 | 123 | 34.0% | dP2R4 |
| 209 | 4.0 | 2.0 | 9.0% | P6R0.9 | 6 | 0.9 | 136 | 123 | 36.0% | dP2R7 |
| 210 | 4.0 | 2.0 | 8.0% | P6R0.9 | 6 | 0.9 | 136 | 123 | 32.0% | dP2R7 |
| 221 | 9.0 | 4.0 | 5.0% | P6R0.9 | 6 | 0.9 | 136 | 123 | 45.0% | dP2R4 |
| 224 | 5.7 | 2.0 | 6.0% | P6R0.9 | 6 | 0.9 | 136 | 123 | 34.0% | dP2R4 |
| 225 | 9.0 | 2.0 | 5.0% | P6R0.9 | 6 | 0.9 | 136 | 123 | 45.0% | dP2R4 |
| 230 | 5.7 | 2.0 | 7.5% | P6R0.9 | 6 | 0.9 | 136 | 123 | 42.5% | dP1R5 |
| 234 | 5.7 | 2.0 | 6.0% | P6R0.9 | 6 | 0.9 | 136 | 123 | 34.0% | dP1R5 |
| 241 | 5.9 | 2.0 | 6.5% | P6R0.9 | 6 | 0.9 | 136 | 123 | 38.5% | dP1R5 |
| 245 | 5.9 | 2.0 | 6.5% | P2R2 | 2 | 2 | 45 | 91 | 38.5% | dP1R5 |
| 246 | 5.7 | 2.0 | 7.5% | P2R2 | 2 | 2 | 45 | 91 | 42.5% | dP1R5 |
| 247 | 9.0 | 2.0 | 5.0% | P2R2 | 2 | 2 | 45 | 91 | 45.0% | dP1R5 |
| 250 | 9.0 | 4.0 | 5.0% | P6R0.9 | 6 | 0.9 | 136 | 123 | 45.0% | dP2R4 |

| | | Diblock copolymer (DB) PEG | | | | Solvent 1 | | Solvent 2 | |
|---|---|---|---|---|---|---|---|---|---|
| N° | Ratio DB/TB | size (kDa) | Ratio (LA/EO) | DP-PEG | DP-PLA | Name | % (w/w) | Name | % (w/w) |
| 10 | 4.0 | 2 | 3.2 | 45 | 143 | DEGMEE | 46.0% | | |
| 12 | 4.0 | 2 | 3.2 | 45 | 143 | DEGMEE | 46.0% | | |
| 21 | 4.0 | 2 | 3.2 | 45 | 143 | Diglyme | 46.0% | | |
| 23 | 4.0 | 2 | 3.2 | 45 | 143 | Diglyme | 46.0% | | |
| 34 | 4.0 | 2 | 3.2 | 45 | 143 | DMI | 46.0% | | |
| 45 | 4.0 | 2 | 3.2 | 45 | 143 | DMI | 46.0% | | |
| 66 | 4.0 | 2 | 3.2 | 45 | 143 | Diglyme | 46.0% | | |
| 68 | 4.0 | 2 | 3.2 | 45 | 143 | Diglyme | 46.0% | | |
| 76 | 4.0 | 2 | 3.2 | 45 | 143 | DMSO | 46.0% | | |
| 78 | 4.0 | 2 | 3.2 | 45 | 143 | DMSO | 46.0% | | |
| 80 | 4.0 | 2 | 3.2 | 45 | 143 | EtLactate | 46.0% | | |
| 82 | 4.0 | 2 | 3.2 | 45 | 143 | EtLactate | 46.0% | | |
| 105 | 4.0 | 2 | 4.4 | 45 | 200 | Diglyme | 56.0% | | |
| 116 | 4.0 | 2 | 4.4 | 45 | 200 | Diglyme | 56.0% | | |
| 123 | 4.0 | 2 | 4.3 | 45 | 195 | DMSO | 56.0% | | |
| 124 | 4.0 | 2 | 4.3 | 45 | 195 | DMSO | 56.0% | | |
| 153 | 4.0 | 2 | 4.3 | 45 | 195 | DMSO | 61.0% | | |
| 159 | 4.0 | 2 | 4.3 | 45 | 195 | DMSO | 44.0% | Tracetin | 17.0% |

TABLE 1-continued

| | | | | | | | | | |
|---|---|---|---|---|---|---|---|---|---|
| 169 | 5.7 | 2 | 4.3 | 45 | 195 | DMSO | 58.0% | | |
| 177 | 5.7 | 2 | 4.3 | 45 | 195 | DMSO | 48.0% | | |
| 198 | 9.0 | 2 | 4.3 | 45 | 195 | Diglyme | 37.0% | Tripro | 19.0% |
| 200 | 9.0 | 2 | 3 | 45 | 136 | DMSO | 48.0% | | |
| 203 | 4.0 | 2 | 7.2 | 45 | 327 | DMSO | 48.0% | | |
| 207 | 5.7 | 2 | 4.3 | 45 | 195 | Diglyme | 40.0% | Tripro | 16.0% |
| 209 | 4.0 | 2 | 7.2 | 45 | 327 | DMSO | 53.0% | | |
| 210 | 4.0 | 2 | 7.2 | 45 | 327 | DMSO | 58.0% | | |
| 221 | 9.0 | 2 | 4.3 | 45 | 195 | Diglyme | 33.0% | Tripro | 13.0% |
| 224 | 5.7 | 2 | 4.3 | 45 | 195 | Diglyme | 41.4% | Tripro | 16.6% |
| 225 | 9.0 | 2 | 4.3 | 45 | 195 | Diglyme | 34.0% | Tripro | 13.6% |
| 230 | 5.7 | 1 | 5.4 | 23 | 123 | DMSO | 48.0% | | |
| 234 | 5.7 | 1 | 5.4 | 23 | 123 | Diglyme | 41.4% | Tripro | 16.6% |
| 241 | 5.9 | 1 | 5.4 | 23 | 123 | DMSO | 53.0% | | |
| 245 | 5.9 | 1 | 5.4 | 23 | 123 | DMSO | 53% | | |
| 246 | 5.7 | 1 | 5.4 | 23 | 123 | DMSO | 48.0% | | |
| 247 | 9.0 | 1 | 5.4 | 23 | 123 | DMSO | 48.0% | | |
| 250 | 9.0 | 2 | 4.3 | 45 | 195 | Diglyme | 33.2% | Tripro | 12.8% |

Example 4

Acetaminophen's Formulations Preparation

The formulations described herein were based on organic solution of polymers prepared as in Example 1, containing as the drug, acetaminophen. Typically, 0.4 grams of polymers, corresponding to a mix of a diblock copolymer and a triblock copolymer in defined mass ratio, were dissolved in 0.55 grams of dimethyl sulfoxide at room temperature overnight under constant magnetic stirring. The next day, 50 mg of acetaminophen was added to the polymer solution and stirred until complete dissolution. The formulations were loaded in a syringe before use. The composition of the various formulations is shown in Table 2 below, where the solvent used is DMSO.

FIGS. 7 to 26 illustrate the results of these formulations which show all possible combinations of 15 triblock copolymers with 20 diblocks copolymers.

TABLE 2

| | | Triblock copolymer (TB) | | | | | | Diblock copolymer (DB) | | | | | | Solvent | |
|---|---|---|---|---|---|---|---|---|---|---|---|---|---|---|---|
| Exp nº | Ratio DB/TB | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 1 | 4.0 | 8% | P0.2R14 | 0.2 | 14.5 | 4 | 58 | 32% | dP0.2R6 | 0.2 | 5.8 | 3 | 17 | DMSO | 55% |
| 2 | 4.0 | 8% | P0.2R14 | 0.2 | 14.5 | 4 | 58 | 32% | dP0.4R6 | 0.4 | 5.8 | 7 | 42 | DMSO | 55% |
| 3 | 4.0 | 8% | P0.2R14 | 0.2 | 14.5 | 4 | 58 | 32% | dP0.6R5 | 0.6 | 4.6 | 12 | 54 | DMSO | 55% |
| 4 | 4.0 | 8% | P0.2R14 | 0.2 | 14.5 | 4 | 58 | 32% | dP1R4 | 1.0 | 4.0 | 22 | 89 | DMSO | 55% |
| 5 | 4.0 | 8% | P0.2R14 | 0.2 | 14.5 | 4 | 58 | 32% | dP2R3 | 2.0 | 2.8 | 45 | 125 | DMSO | 55% |
| 6 | 4.0 | 8% | P0.6R3 | 0.6 | 3.0 | 13 | 40 | 32% | dP0.2R6 | 0.2 | 5.8 | 3 | 17 | DMSO | 55% |
| 7 | 4.0 | 8% | P0.6R3 | 0.6 | 3.0 | 13 | 40 | 32% | dP0.4R6 | 0.4 | 5.8 | 7 | 42 | DMSO | 55% |
| 8 | 4.0 | 8% | P0.6R3 | 0.6 | 3.0 | 13 | 40 | 32% | dP0.6R5 | 0.6 | 4.6 | 12 | 54 | DMSO | 55% |
| 9 | 4.0 | 8% | P0.6R3 | 0.6 | 3.0 | 13 | 40 | 32% | dP1R4 | 1.0 | 4.0 | 22 | 89 | DMSO | 55% |
| 10 | 4.0 | 8% | P0.6R3 | 0.6 | 3.0 | 13 | 40 | 32% | dP2R3 | 2.0 | 2.8 | 45 | 125 | DMSO | 55% |
| 11 | 4.0 | 8% | P1R3 | 1.0 | 3.1 | 22 | 68 | 32% | dP0.2R6 | 0.2 | 5.8 | 3 | 17 | DMSO | 55% |
| 12 | 4.0 | 8% | P1R3 | 1.0 | 3.1 | 22 | 68 | 32% | dP0.4R6 | 0.4 | 5.8 | 7 | 42 | DMSO | 55% |
| 13 | 4.0 | 8% | P1R3 | 1.0 | 3.1 | 22 | 68 | 32% | dP0.6R5 | 0.6 | 4.6 | 12 | 54 | DMSO | 55% |
| 14 | 4.0 | 8% | P1R3 | 1.0 | 3.1 | 22 | 68 | 32% | dP1R4 | 1.0 | 4.0 | 22 | 89 | DMSO | 55% |
| 15 | 4.0 | 8% | P1R3 | 1.0 | 3.1 | 22 | 68 | 32% | dP2R3 | 2.0 | 2.8 | 45 | 125 | DMSO | 55% |
| 16 | 4.0 | 8% | P2R3 | 2.0 | 3.5 | 45 | 157 | 32% | dP0.2R6 | 0.2 | 5.8 | 3 | 17 | DMSO | 55% |
| 17 | 4.0 | 8% | P2R3 | 2.0 | 3.5 | 45 | 157 | 32% | dP0.4R6 | 0.4 | 5.8 | 7 | 42 | DMSO | 55% |
| 18 | 4.0 | 8% | P2R3 | 2.0 | 3.5 | 45 | 157 | 32% | dP0.6R5 | 0.6 | 4.6 | 12 | 54 | DMSO | 55% |
| 19 | 4.0 | 8% | P2R3 | 2.0 | 3.5 | 45 | 157 | 32% | dP1R4 | 1.0 | 4.0 | 22 | 89 | DMSO | 55% |
| 20 | 4.0 | 8% | P2R3 | 2.0 | 3.5 | 45 | 157 | 32% | dP2R3 | 2.0 | 2.8 | 45 | 125 | DMSO | 55% |
| 21 | 4.0 | 8% | P3R2 | 3.0 | 2.3 | 68 | 154 | 32% | dP0.2R6 | 0.2 | 5.8 | 3 | 17 | DMSO | 55% |
| 22 | 4.0 | 8% | P3R2 | 3.0 | 2.3 | 68 | 154 | 32% | dP0.4R6 | 0.4 | 5.8 | 7 | 42 | DMSO | 55% |
| 23 | 4.0 | 8% | P3R2 | 3.0 | 2.3 | 68 | 154 | 32% | dP0.6R5 | 0.6 | 4.6 | 12 | 54 | DMSO | 55% |
| 24 | 4.0 | 8% | P3R2 | 3.0 | 2.3 | 68 | 154 | 32% | dP1R4 | 1.0 | 4.0 | 22 | 89 | DMSO | 55% |
| 25 | 4.0 | 8% | P3R2 | 3.0 | 2.3 | 68 | 154 | 32% | dP2R3 | 2.0 | 2.8 | 45 | 125 | DMSO | 55% |
| 26 | 4.0 | 8% | P6R2 | 6.0 | 1.6 | 136 | 218 | 32% | dP0.2R6 | 0.2 | 5.8 | 3 | 17 | DMSO | 55% |
| 27 | 4.0 | 8% | P6R2 | 6.0 | 1.6 | 136 | 218 | 32% | dP0.4R6 | 0.4 | 5.8 | 7 | 42 | DMSO | 55% |
| 28 | 4.0 | 8% | P6R2 | 6.0 | 1.6 | 136 | 218 | 32% | dP0.6R5 | 0.6 | 4.6 | 12 | 54 | DMSO | 55% |
| 29 | 4.0 | 8% | P6R2 | 6.0 | 1.6 | 136 | 218 | 32% | dP1R4 | 1.0 | 4.0 | 22 | 89 | DMSO | 55% |
| 30 | 4.0 | 8% | P6R2 | 6.0 | 1.6 | 136 | 218 | 32% | dP2R3 | 2.0 | 2.8 | 45 | 125 | DMSO | 55% |
| 31 | 4.0 | 8% | P0.2R6 | 0.2 | 5.9 | 4 | 24 | 32% | dP0.2R2 | 0.2 | 2.2 | 3 | 7 | DMSO | 55% |
| 32 | 4.0 | 8% | P0.2R6 | 0.2 | 5.9 | 4 | 24 | 32% | dP0.2R13 | 0.2 | 13.0 | 3 | 39 | DMSO | 55% |
| 33 | 4.0 | 8% | P0.2R6 | 0.2 | 5.9 | 4 | 24 | 32% | dP0.4R2 | 0.4 | 2.0 | 7 | 14 | DMSO | 55% |
| 34 | 4.0 | 8% | P0.2R6 | 0.2 | 5.9 | 4 | 24 | 32% | dP0.4R8 | 0.4 | 8.4 | 7 | 61 | DMSO | 55% |
| 35 | 4.0 | 8% | P0.2R6 | 0.2 | 5.9 | 4 | 24 | 32% | dP0.6R3 | 0.6 | 3.0 | 12 | 35 | DMSO | 55% |
| 36 | 4.0 | 8% | P0.2R6 | 0.2 | 5.9 | 4 | 24 | 32% | dP0.6R5 | 0.6 | 5.1 | 12 | 60 | DMSO | 55% |
| 37 | 4.0 | 8% | P0.2R6 | 0.2 | 5.9 | 4 | 24 | 32% | dP1R3 | 1.0 | 3.0 | 22 | 66 | DMSO | 55% |
| 38 | 4.0 | 8% | P0.2R6 | 0.2 | 5.9 | 4 | 24 | 32% | dP1R5 | 1.0 | 5.4 | 22 | 119 | DMSO | 55% |

TABLE 2-continued

| Exp | Ratio | Triblock copolymer (TB) | | | | | | Diblock copolymer (DB) | | | | | | Solvent | |
|---|---|---|---|---|---|---|---|---|---|---|---|---|---|---|---|
| n° | DB/TB | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 39 | 4.0 | 8% | P0.2R6 | 0.2 | 5.9 | 4 | 24 | 32% | dP2R1 | 2.0 | 1.3 | 45 | 58 | DMSO | 55% |
| 40 | 4.0 | 8% | P0.2R6 | 0.2 | 5.9 | 4 | 24 | 32% | dP2R5 | 2.0 | 5.3 | 45 | 237 | DMSO | 55% |
| 41 | 4.0 | 8% | P0.2R22 | 0.2 | 22.3 | 4 | 89 | 32% | dP0.2R2 | 0.2 | 2.2 | 3 | 7 | DMSO | 55% |
| 42 | 4.0 | 8% | P0.2R22 | 0.2 | 22.3 | 4 | 89 | 32% | dP0.2R13 | 0.2 | 13.0 | 3 | 39 | DMSO | 55% |
| 43 | 4.0 | 8% | P0.2R22 | 0.2 | 22.3 | 4 | 89 | 32% | dP0.4R2 | 0.4 | 2.0 | 7 | 14 | DMSO | 55% |
| 44 | 4.0 | 8% | P0.2R22 | 0.2 | 22.3 | 4 | 89 | 32% | dP0.4R8 | 0.4 | 8.4 | 7 | 61 | DMSO | 55% |
| 45 | 4.0 | 8% | P0.2R22 | 0.2 | 22.3 | 4 | 89 | 32% | dP0.6R3 | 0.6 | 3.0 | 12 | 35 | DMSO | 55% |
| 46 | 4.0 | 8% | P0.2R22 | 0.2 | 22.3 | 4 | 89 | 32% | dP0.6R5 | 0.6 | 5.1 | 12 | 60 | DMSO | 55% |
| 47 | 4.0 | 8% | P0.2R22 | 0.2 | 22.3 | 4 | 89 | 32% | dP1R3 | 1.0 | 3.0 | 22 | 66 | DMSO | 55% |
| 48 | 4.0 | 8% | P0.2R22 | 0.2 | 22.3 | 4 | 89 | 32% | dP1R5 | 1.0 | 5.4 | 22 | 119 | DMSO | 55% |
| 49 | 4.0 | 8% | P0.2R22 | 0.2 | 22.3 | 4 | 89 | 32% | dP2R1 | 2.0 | 1.3 | 45 | 58 | DMSO | 55% |
| 50 | 4.0 | 8% | P0.2R22 | 0.2 | 22.3 | 4 | 89 | 32% | dP2R5 | 2.0 | 5.3 | 45 | 237 | DMSO | 55% |
| 51 | 4.0 | 8% | P0.4R5 | 0.4 | 4.7 | 9 | 41 | 32% | dP0.2R2 | 0.2 | 2.2 | 3 | 7 | DMSO | 55% |
| 52 | 4.0 | 8% | P0.4R5 | 0.4 | 4.7 | 9 | 41 | 32% | dP0.2R13 | 0.2 | 13.0 | 3 | 39 | DMSO | 55% |
| 53 | 4.0 | 8% | P0.4R5 | 0.4 | 4.7 | 9 | 41 | 32% | dP0.4R2 | 0.4 | 2.0 | 7 | 14 | DMSO | 55% |
| 54 | 4.0 | 8% | P0.4R5 | 0.4 | 4.7 | 9 | 41 | 32% | dP0.4R8 | 0.4 | 8.4 | 7 | 61 | DMSO | 55% |
| 55 | 4.0 | 8% | P0.4R5 | 0.4 | 4.7 | 9 | 41 | 32% | dP0.6R3 | 0.6 | 3.0 | 12 | 35 | DMSO | 55% |
| 56 | 4.0 | 8% | P0.4R5 | 0.4 | 4.7 | 9 | 41 | 32% | dP0.6R5 | 0.6 | 5.1 | 12 | 60 | DMSO | 55% |
| 57 | 4.0 | 8% | P0.4R5 | 0.4 | 4.7 | 9 | 41 | 32% | dP1R3 | 1.0 | 3.0 | 22 | 66 | DMSO | 55% |
| 58 | 4.0 | 8% | P0.4R5 | 0.4 | 4.7 | 9 | 41 | 32% | dP1R5 | 1.0 | 5.4 | 22 | 119 | DMSO | 55% |
| 59 | 4.0 | 8% | P0.4R5 | 0.4 | 4.7 | 9 | 41 | 32% | dP2R1 | 2.0 | 1.3 | 45 | 58 | DMSO | 55% |
| 60 | 4.0 | 8% | P0.4R5 | 0.4 | 4.7 | 9 | 41 | 32% | dP2R5 | 2.0 | 5.3 | 45 | 237 | DMSO | 55% |
| 61 | 4.0 | 8% | P0.4R8 | 0.4 | 7.7 | 9 | 67 | 32% | dP0.2R2 | 0.2 | 2.2 | 3 | 7 | DMSO | 55% |
| 62 | 4.0 | 8% | P0.4R8 | 0.4 | 7.7 | 9 | 67 | 32% | dP0.2R13 | 0.2 | 13.0 | 3 | 39 | DMSO | 55% |
| 63 | 4.0 | 8% | P0.4R8 | 0.4 | 7.7 | 9 | 67 | 32% | dP0.4R2 | 0.4 | 2.0 | 7 | 14 | DMSO | 55% |
| 64 | 4.0 | 8% | P0.4R8 | 0.4 | 7.7 | 9 | 67 | 32% | dP0.4R8 | 0.4 | 8.4 | 7 | 61 | DMSO | 55% |
| 65 | 4.0 | 8% | P0.4R8 | 0.4 | 7.7 | 9 | 67 | 32% | dP0.6R3 | 0.6 | 3.0 | 12 | 35 | DMSO | 55% |
| 66 | 4.0 | 8% | P0.4R8 | 0.4 | 7.7 | 9 | 67 | 32% | dP0.6R5 | 0.6 | 5.1 | 12 | 60 | DMSO | 55% |
| 67 | 4.0 | 8% | P0.4R8 | 0.4 | 7.7 | 9 | 67 | 32% | dP1R3 | 1.0 | 3.0 | 22 | 66 | DMSO | 55% |
| 68 | 4.0 | 8% | P0.4R8 | 0.4 | 7.7 | 9 | 67 | 32% | dP1R5 | 1.0 | 5.4 | 22 | 119 | DMSO | 55% |
| 69 | 4.0 | 8% | P0.4R8 | 0.4 | 7.7 | 9 | 67 | 32% | dP2R1 | 2.0 | 1.3 | 45 | 58 | DMSO | 55% |
| 70 | 4.0 | 8% | P0.4R8 | 0.4 | 7.7 | 9 | 67 | 32% | dP2R5 | 2.0 | 5.3 | 45 | 237 | DMSO | 55% |
| 71 | 4.0 | 8% | P0.6R2 | 0.6 | 1.9 | 13 | 26 | 32% | dP0.2R2 | 0.2 | 2.2 | 3 | 7 | DMSO | 55% |
| 72 | 4.0 | 8% | P0.6R2 | 0.6 | 1.9 | 13 | 26 | 32% | dP0.2R13 | 0.2 | 13.0 | 3 | 39 | DMSO | 55% |
| 73 | 4.0 | 8% | P0.6R2 | 0.6 | 1.9 | 13 | 26 | 32% | dP0.4R2 | 0.4 | 2.0 | 7 | 14 | DMSO | 55% |
| 74 | 4.0 | 8% | P0.6R2 | 0.6 | 1.9 | 13 | 26 | 32% | dP0.4R8 | 0.4 | 8.4 | 7 | 61 | DMSO | 55% |
| 75 | 4.0 | 8% | P0.6R2 | 0.6 | 1.9 | 13 | 26 | 32% | dP0.6R3 | 0.6 | 3.0 | 12 | 35 | DMSO | 55% |
| 76 | 4.0 | 8% | P0.6R2 | 0.6 | 1.9 | 13 | 26 | 32% | dP0.6R5 | 0.6 | 5.1 | 12 | 60 | DMSO | 55% |
| 77 | 4.0 | 8% | P0.6R2 | 0.6 | 1.9 | 13 | 26 | 32% | dP1R3 | 1.0 | 3.0 | 22 | 66 | DMSO | 55% |
| 78 | 4.0 | 8% | P0.6R2 | 0.6 | 1.9 | 13 | 26 | 32% | dP1R5 | 1.0 | 5.4 | 22 | 119 | DMSO | 55% |
| 79 | 4.0 | 8% | P0.6R2 | 0.6 | 1.9 | 13 | 26 | 32% | dP2R1 | 2.0 | 1.3 | 45 | 58 | DMSO | 55% |
| 80 | 4.0 | 8% | P0.6R2 | 0.6 | 1.9 | 13 | 26 | 32% | dP2R5 | 2.0 | 5.3 | 45 | 237 | DMSO | 55% |
| 81 | 4.0 | 8% | P0.6R4 | 0.6 | 4.2 | 13 | 55 | 32% | dP0.2R2 | 0.2 | 2.2 | 3 | 7 | DMSO | 55% |
| 82 | 4.0 | 8% | P0.6R4 | 0.6 | 4.2 | 13 | 55 | 32% | dP0.2R13 | 0.2 | 13.0 | 3 | 39 | DMSO | 55% |
| 83 | 4.0 | 8% | P0.6R4 | 0.6 | 4.2 | 13 | 55 | 32% | dP0.4R2 | 0.4 | 2.0 | 7 | 14 | DMSO | 55% |
| 84 | 4.0 | 8% | P0.6R4 | 0.6 | 4.2 | 13 | 55 | 32% | dP0.4R8 | 0.4 | 8.4 | 7 | 61 | DMSO | 55% |
| 85 | 4.0 | 8% | P0.6R4 | 0.6 | 4.2 | 13 | 55 | 32% | dP0.6R3 | 0.6 | 3.0 | 12 | 35 | DMSO | 55% |
| 86 | 4.0 | 8% | P0.6R4 | 0.6 | 4.2 | 13 | 55 | 32% | dP0.6R5 | 0.6 | 5.1 | 12 | 60 | DMSO | 55% |
| 87 | 4.0 | 8% | P0.6R4 | 0.6 | 4.2 | 13 | 55 | 32% | dP1R3 | 1.0 | 3.0 | 22 | 66 | DMSO | 55% |
| 88 | 4.0 | 8% | P0.6R4 | 0.6 | 4.2 | 13 | 55 | 32% | dP1R5 | 1.0 | 5.4 | 22 | 119 | DMSO | 55% |
| 89 | 4.0 | 8% | P0.6R4 | 0.6 | 4.2 | 13 | 55 | 32% | dP2R1 | 2.0 | 1.3 | 45 | 58 | DMSO | 55% |
| 90 | 4.0 | 8% | P0.6R4 | 0.6 | 4.2 | 13 | 55 | 32% | dP2R5 | 2.0 | 5.3 | 45 | 237 | DMSO | 55% |
| 91 | 4.0 | 8% | P1R2 | 1.0 | 2.1 | 22 | 47 | 32% | dP0.2R2 | 0.2 | 2.2 | 3 | 7 | DMSO | 55% |
| 92 | 4.0 | 8% | P1R2 | 1.0 | 2.1 | 22 | 47 | 32% | dP0.2R13 | 0.2 | 13.0 | 3 | 39 | DMSO | 55% |
| 93 | 4.0 | 8% | P1R2 | 1.0 | 2.1 | 22 | 47 | 32% | dP0.4R2 | 0.4 | 2.0 | 7 | 14 | DMSO | 55% |
| 94 | 4.0 | 8% | P1R2 | 1.0 | 2.1 | 22 | 47 | 32% | dP0.4R8 | 0.4 | 8.4 | 7 | 61 | DMSO | 55% |
| 95 | 4.0 | 8% | P1R2 | 1.0 | 2.1 | 22 | 47 | 32% | dP0.6R3 | 0.6 | 3.0 | 12 | 35 | DMSO | 55% |
| 96 | 4.0 | 8% | P1R2 | 1.0 | 2.1 | 22 | 47 | 32% | dP0.6R5 | 0.6 | 5.1 | 12 | 60 | DMSO | 55% |
| 97 | 4.0 | 8% | P1R2 | 1.0 | 2.1 | 22 | 47 | 32% | dP1R3 | 1.0 | 3.0 | 22 | 66 | DMSO | 55% |
| 98 | 4.0 | 8% | P1R2 | 1.0 | 2.1 | 22 | 47 | 32% | dP1R5 | 1.0 | 5.4 | 22 | 119 | DMSO | 55% |
| 99 | 4.0 | 8% | P1R2 | 1.0 | 2.1 | 22 | 47 | 32% | dP2R1 | 2.0 | 1.3 | 45 | 58 | DMSO | 55% |
| 100 | 4.0 | 8% | P1R2 | 1.0 | 2.1 | 22 | 47 | 32% | dP2R5 | 2.0 | 5.3 | 45 | 237 | DMSO | 55% |
| 101 | 4.0 | 8% | P1R4 | 1.0 | 4.0 | 22 | 88 | 32% | dP0.2R2 | 0.2 | 2.2 | 3 | 7 | DMSO | 55% |
| 102 | 4.0 | 8% | P1R4 | 1.0 | 4.0 | 22 | 88 | 32% | dP0.2R13 | 0.2 | 13.0 | 3 | 39 | DMSO | 55% |
| 103 | 4.0 | 8% | P1R4 | 1.0 | 4.0 | 22 | 88 | 32% | dP0.4R2 | 0.4 | 2.0 | 7 | 14 | DMSO | 55% |
| 104 | 4.0 | 8% | P1R4 | 1.0 | 4.0 | 22 | 88 | 32% | dP0.4R8 | 0.4 | 8.4 | 7 | 61 | DMSO | 55% |
| 105 | 4.0 | 8% | P1R4 | 1.0 | 4.0 | 22 | 88 | 32% | dP0.6R3 | 0.6 | 3.0 | 12 | 35 | DMSO | 55% |
| 106 | 4.0 | 8% | P1R4 | 1.0 | 4.0 | 22 | 88 | 32% | dP0.6R5 | 0.6 | 5.1 | 12 | 60 | DMSO | 55% |
| 107 | 4.0 | 8% | P1R4 | 1.0 | 4.0 | 22 | 88 | 32% | dP1R3 | 1.0 | 3.0 | 22 | 66 | DMSO | 55% |
| 108 | 4.0 | 8% | P1R4 | 1.0 | 4.0 | 22 | 88 | 32% | dP1R5 | 1.0 | 5.4 | 22 | 119 | DMSO | 55% |
| 109 | 4.0 | 8% | P1R4 | 1.0 | 4.0 | 22 | 88 | 32% | dP2R1 | 2.0 | 1.3 | 45 | 58 | DMSO | 55% |
| 110 | 4.0 | 8% | P1R4 | 1.0 | 4.0 | 22 | 88 | 32% | dP2R5 | 2.0 | 5.3 | 45 | 237 | DMSO | 55% |
| 111 | 4.0 | 8% | P2R2 | 2.0 | 2.0 | 45 | 88 | 32% | dP0.2R2 | 0.2 | 2.2 | 3 | 7 | DMSO | 55% |
| 112 | 4.0 | 8% | P2R2 | 2.0 | 2.0 | 45 | 88 | 32% | dP0.2R13 | 0.2 | 13.0 | 3 | 39 | DMSO | 55% |

TABLE 2-continued

| | | Triblock copolymer (TB) | | | | | | Diblock copolymer (DB) | | | | | | Solvent | |
|---|---|---|---|---|---|---|---|---|---|---|---|---|---|---|---|
| Exp n° | Ratio DB/TB | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 113 | 4.0 | 8% | P2R2 | 2.0 | 2.0 | 45 | 88 | 32% | dP0.4R2 | 0.4 | 2.0 | 7 | 14 | DMSO | 55% |
| 114 | 4.0 | 8% | P2R2 | 2.0 | 2.0 | 45 | 88 | 32% | dP0.4R8 | 0.4 | 8.4 | 7 | 61 | DMSO | 55% |
| 115 | 4.0 | 8% | P2R2 | 2.0 | 2.0 | 45 | 88 | 32% | dP0.6R3 | 0.6 | 3.0 | 12 | 35 | DMSO | 55% |
| 116 | 4.0 | 8% | P2R2 | 2.0 | 2.0 | 45 | 88 | 32% | dP0.6R5 | 0.6 | 5.1 | 12 | 60 | DMSO | 55% |
| 117 | 4.0 | 8% | P2R2 | 2.0 | 2.0 | 45 | 88 | 32% | dP1R3 | 1.0 | 3.0 | 22 | 66 | DMSO | 55% |
| 118 | 4.0 | 8% | P2R2 | 2.0 | 2.0 | 45 | 88 | 32% | dP1R5 | 1.0 | 5.4 | 22 | 119 | DMSO | 55% |
| 119 | 4.0 | 8% | P2R2 | 2.0 | 2.0 | 45 | 88 | 32% | dP2R1 | 2.0 | 1.3 | 45 | 58 | DMSO | 55% |
| 120 | 4.0 | 8% | P2R2 | 2.0 | 2.0 | 45 | 88 | 32% | dP2R5 | 2.0 | 5.3 | 45 | 237 | DMSO | 55% |
| 121 | 4.0 | 8% | P2R5 | 2.0 | 4.8 | 45 | 216 | 32% | dP0.2R2 | 0.2 | 2.2 | 3 | 7 | DMSO | 55% |
| 122 | 4.0 | 8% | P2R5 | 2.0 | 4.8 | 45 | 216 | 32% | dP0.2R13 | 0.2 | 13.0 | 3 | 39 | DMSO | 55% |
| 123 | 4.0 | 8% | P2R5 | 2.0 | 4.8 | 45 | 216 | 32% | dP0.4R2 | 0.4 | 2.0 | 7 | 14 | DMSO | 55% |
| 124 | 4.0 | 8% | P2R5 | 2.0 | 4.8 | 45 | 216 | 32% | dP0.4R8 | 0.4 | 8.4 | 7 | 61 | DMSO | 55% |
| 125 | 4.0 | 8% | P2R5 | 2.0 | 4.8 | 45 | 216 | 32% | dP0.6R3 | 0.6 | 3.0 | 12 | 35 | DMSO | 55% |
| 126 | 4.0 | 8% | P2R5 | 2.0 | 4.8 | 45 | 216 | 32% | dP0.6R5 | 0.6 | 5.1 | 12 | 60 | DMSO | 55% |
| 127 | 4.0 | 8% | P2R5 | 2.0 | 4.8 | 45 | 216 | 32% | dP1R3 | 1.0 | 3.0 | 22 | 66 | DMSO | 55% |
| 128 | 4.0 | 8% | P2R5 | 2.0 | 4.8 | 45 | 216 | 32% | dP1R5 | 1.0 | 5.4 | 22 | 119 | DMSO | 55% |
| 129 | 4.0 | 8% | P2R5 | 2.0 | 4.8 | 45 | 216 | 32% | dP2R1 | 2.0 | 1.3 | 45 | 58 | DMSO | 55% |
| 130 | 4.0 | 8% | P2R5 | 2.0 | 4.8 | 45 | 216 | 32% | dP2R5 | 2.0 | 5.3 | 45 | 237 | DMSO | 55% |
| 131 | 4.0 | 8% | P3R1 | 3.0 | 1.0 | 68 | 66 | 32% | dP0.2R2 | 0.2 | 2.2 | 3 | 7 | DMSO | 55% |
| 132 | 4.0 | 8% | P3R1 | 3.0 | 1.0 | 68 | 66 | 32% | dP0.2R13 | 0.2 | 13.0 | 3 | 39 | DMSO | 55% |
| 133 | 4.0 | 8% | P3R1 | 3.0 | 1.0 | 68 | 66 | 32% | dP0.4R2 | 0.4 | 2.0 | 7 | 14 | DMSO | 55% |
| 134 | 4.0 | 8% | P3R1 | 3.0 | 1.0 | 68 | 66 | 32% | dP0.4R8 | 0.4 | 8.4 | 7 | 61 | DMSO | 55% |
| 135 | 4.0 | 8% | P3R1 | 3.0 | 1.0 | 68 | 66 | 32% | dP0.6R3 | 0.6 | 3.0 | 12 | 35 | DMSO | 55% |
| 136 | 4.0 | 8% | P3R1 | 3.0 | 1.0 | 68 | 66 | 32% | dP0.6R5 | 0.6 | 5.1 | 12 | 60 | DMSO | 55% |
| 137 | 4.0 | 8% | P3R1 | 3.0 | 1.0 | 68 | 66 | 32% | dP1R3 | 1.0 | 3.0 | 22 | 66 | DMSO | 55% |
| 138 | 4.0 | 8% | P3R1 | 3.0 | 1.0 | 68 | 66 | 32% | dP1R5 | 1.0 | 5.4 | 22 | 119 | DMSO | 55% |
| 139 | 4.0 | 8% | P3R1 | 3.0 | 1.0 | 68 | 66 | 32% | dP2R1 | 2.0 | 1.3 | 45 | 58 | DMSO | 55% |
| 140 | 4.0 | 8% | P3R1 | 3.0 | 1.0 | 68 | 66 | 32% | dP2R5 | 2.0 | 5.3 | 45 | 237 | DMSO | 55% |
| 141 | 4.0 | 8% | P3R3 | 3.0 | 3.2 | 68 | 218 | 32% | dP0.2R2 | 0.2 | 2.2 | 3 | 7 | DMSO | 55% |
| 142 | 4.0 | 8% | P3R3 | 3.0 | 3.2 | 68 | 218 | 32% | dP0.2R13 | 0.2 | 13.0 | 3 | 39 | DMSO | 55% |
| 143 | 4.0 | 8% | P3R3 | 3.0 | 3.2 | 68 | 218 | 32% | dP0.4R2 | 0.4 | 2.0 | 7 | 14 | DMSO | 55% |
| 144 | 4.0 | 8% | P3R3 | 3.0 | 3.2 | 68 | 218 | 32% | dP0.4R8 | 0.4 | 8.4 | 7 | 61 | DMSO | 55% |
| 145 | 4.0 | 8% | P3R3 | 3.0 | 3.2 | 68 | 218 | 32% | dP0.6R3 | 0.6 | 3.0 | 12 | 35 | DMSO | 55% |
| 146 | 4.0 | 8% | P3R3 | 3.0 | 3.2 | 68 | 218 | 32% | dP0.6R5 | 0.6 | 5.1 | 12 | 60 | DMSO | 55% |
| 147 | 4.0 | 8% | P3R3 | 3.0 | 3.2 | 68 | 218 | 32% | dP1R3 | 1.0 | 3.0 | 22 | 66 | DMSO | 55% |
| 148 | 4.0 | 8% | P3R3 | 3.0 | 3.2 | 68 | 218 | 32% | dP1R5 | 1.0 | 5.4 | 22 | 119 | DMSO | 55% |
| 149 | 4.0 | 8% | P3R3 | 3.0 | 3.2 | 68 | 218 | 32% | dP2R1 | 2.0 | 1.3 | 45 | 58 | DMSO | 55% |
| 150 | 4.0 | 8% | P3R3 | 3.0 | 3.2 | 68 | 218 | 32% | dP2R5 | 2.0 | 5.3 | 45 | 237 | DMSO | 55% |
| 151 | 4.0 | 8% | P6R0.9 | 6.0 | 0.9 | 136 | 125 | 32% | dP0.2R2 | 0.2 | 2.2 | 3 | 7 | DMSO | 55% |
| 152 | 4.0 | 8% | P6R0.9 | 6.0 | 0.9 | 136 | 125 | 32% | dP0.2R13 | 0.2 | 13.0 | 3 | 39 | DMSO | 55% |
| 153 | 4.0 | 8% | P6R0.9 | 6.0 | 0.9 | 136 | 125 | 32% | dP0.4R2 | 0.4 | 2.0 | 7 | 14 | DMSO | 55% |
| 154 | 4.0 | 8% | P6R0.9 | 6.0 | 0.9 | 136 | 125 | 32% | dP0.4R8 | 0.4 | 8.4 | 7 | 61 | DMSO | 55% |
| 155 | 4.0 | 8% | P6R0.9 | 6.0 | 0.9 | 136 | 125 | 32% | dP0.6R3 | 0.6 | 3.0 | 12 | 35 | DMSO | 55% |
| 156 | 4.0 | 8% | P6R0.9 | 6.0 | 0.9 | 136 | 125 | 32% | dP0.6R5 | 0.6 | 5.1 | 12 | 60 | DMSO | 55% |
| 157 | 4.0 | 8% | P6R0.9 | 6.0 | 0.9 | 136 | 125 | 32% | dP1R3 | 1.0 | 3.0 | 22 | 66 | DMSO | 55% |
| 158 | 4.0 | 8% | P6R0.9 | 6.0 | 0.9 | 136 | 125 | 32% | dP1R5 | 1.0 | 5.4 | 22 | 119 | DMSO | 55% |
| 159 | 4.0 | 8% | P6R0.9 | 6.0 | 0.9 | 136 | 125 | 32% | dP2R1 | 2.0 | 1.3 | 45 | 58 | DMSO | 55% |
| 160 | 4.0 | 8% | P6R0.9 | 6.0 | 0.9 | 136 | 125 | 32% | dP2R5 | 2.0 | 5.3 | 45 | 237 | DMSO | 55% |
| 161 | 4.0 | 8% | P6R2 | 6.0 | 2.0 | 136 | 272 | 32% | dP0.2R2 | 0.2 | 2.2 | 3 | 7 | DMSO | 55% |
| 162 | 4.0 | 8% | P6R2 | 6.0 | 2.0 | 136 | 272 | 32% | dP0.2R13 | 0.2 | 13.0 | 3 | 39 | DMSO | 55% |
| 163 | 4.0 | 8% | P6R2 | 6.0 | 2.0 | 136 | 272 | 32% | dP0.4R2 | 0.4 | 2.0 | 7 | 14 | DMSO | 55% |
| 164 | 4.0 | 8% | P6R2 | 6.0 | 2.0 | 136 | 272 | 32% | dP0.4R8 | 0.4 | 8.4 | 7 | 61 | DMSO | 55% |
| 165 | 4.0 | 8% | P6R2 | 6.0 | 2.0 | 136 | 272 | 32% | dP0.6R3 | 0.6 | 3.0 | 12 | 35 | DMSO | 55% |
| 166 | 4.0 | 8% | P6R2 | 6.0 | 2.0 | 136 | 272 | 32% | dP0.6R5 | 0.6 | 5.1 | 12 | 60 | DMSO | 55% |
| 167 | 4.0 | 8% | P6R2 | 6.0 | 2.0 | 136 | 272 | 32% | dP1R3 | 1.0 | 3.0 | 22 | 66 | DMSO | 55% |
| 168 | 4.0 | 8% | P6R2 | 6.0 | 2.0 | 136 | 272 | 32% | dP1R5 | 1.0 | 5.4 | 22 | 119 | DMSO | 55% |
| 169 | 4.0 | 8% | P6R2 | 6.0 | 2.0 | 136 | 272 | 32% | dP2R1 | 2.0 | 1.3 | 45 | 58 | DMSO | 55% |
| 170 | 4.0 | 8% | P6R2 | 6.0 | 2.0 | 136 | 272 | 32% | dP2R5 | 2.0 | 5.3 | 45 | 237 | DMSO | 55% |
| 171 | 4.0 | 8% | P0.2R6 | 0.2 | 5.9 | 4 | 24 | 32% | dP0.2R6 | 0.2 | 5.8 | 3 | 17 | DMSO | 55% |
| 172 | 4.0 | 8% | P0.2R6 | 0.2 | 5.9 | 4 | 24 | 32% | dP0.4R6 | 0.4 | 5.8 | 7 | 42 | DMSO | 55% |
| 173 | 4.0 | 8% | P0.2R6 | 0.2 | 5.9 | 4 | 24 | 32% | dP0.6R5 | 0.6 | 4.6 | 12 | 54 | DMSO | 55% |
| 174 | 4.0 | 8% | P0.2R6 | 0.2 | 5.9 | 4 | 24 | 32% | dP1R4 | 1.0 | 4.0 | 22 | 89 | DMSO | 55% |
| 175 | 4.0 | 8% | P0.2R6 | 0.2 | 5.9 | 4 | 24 | 32% | dP2R3 | 2.0 | 2.8 | 45 | 125 | DMSO | 55% |
| 176 | 4.0 | 8% | P0.2R22 | 0.2 | 22.3 | 4 | 89 | 32% | dP0.2R6 | 0.2 | 5.8 | 3 | 17 | DMSO | 55% |
| 177 | 4.0 | 8% | P0.2R22 | 0.2 | 22.3 | 4 | 89 | 32% | dP0.4R6 | 0.4 | 5.8 | 7 | 42 | DMSO | 55% |
| 178 | 4.0 | 8% | P0.2R22 | 0.2 | 22.3 | 4 | 89 | 32% | dP0.6R5 | 0.6 | 4.6 | 12 | 54 | DMSO | 55% |
| 179 | 4.0 | 8% | P0.2R22 | 0.2 | 22.3 | 4 | 89 | 32% | dP1R4 | 1.0 | 4.0 | 22 | 89 | DMSO | 55% |
| 180 | 4.0 | 8% | P0.2R22 | 0.2 | 22.3 | 4 | 89 | 32% | dP2R3 | 2.0 | 2.8 | 45 | 125 | DMSO | 55% |
| 181 | 4.0 | 8% | P0.4R5 | 0.4 | 4.7 | 9 | 41 | 32% | dP0.2R6 | 0.2 | 5.8 | 3 | 17 | DMSO | 55% |
| 182 | 4.0 | 8% | P0.4R5 | 0.4 | 4.7 | 9 | 41 | 32% | dP0.4R6 | 0.4 | 5.8 | 7 | 42 | DMSO | 55% |
| 183 | 4.0 | 8% | P0.4R5 | 0.4 | 4.7 | 9 | 41 | 32% | dP0.6R5 | 0.6 | 4.6 | 12 | 54 | DMSO | 55% |
| 184 | 4.0 | 8% | P0.4R5 | 0.4 | 4.7 | 9 | 41 | 32% | dP1R4 | 1.0 | 4.0 | 22 | 89 | DMSO | 55% |
| 185 | 4.0 | 8% | P0.4R5 | 0.4 | 4.7 | 9 | 41 | 32% | dP2R3 | 2.0 | 2.8 | 45 | 125 | DMSO | 55% |
| 186 | 4.0 | 8% | P0.4R8 | 0.4 | 7.7 | 9 | 67 | 32% | dP0.2R6 | 0.2 | 5.8 | 3 | 17 | DMSO | 55% |

TABLE 2-continued

| | | Triblock copolymer (TB) | | | | | | Diblock copolymer (DB) | | | | | | Solvent | |
|---|---|---|---|---|---|---|---|---|---|---|---|---|---|---|---|
| Exp n° | Ratio DB/TB | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 187 | 4.0 | 8% | P0.4R8 | 0.4 | 7.7 | 9 | 67 | 32% | dP0.4R6 | 0.4 | 5.8 | 7 | 42 | DMSO | 55% |
| 188 | 4.0 | 8% | P0.4R8 | 0.4 | 7.7 | 9 | 67 | 32% | dP0.6R5 | 0.6 | 4.6 | 12 | 54 | DMSO | 55% |
| 189 | 4.0 | 8% | P0.4R8 | 0.4 | 7.7 | 9 | 67 | 32% | dP1R4 | 1.0 | 4.0 | 22 | 89 | DMSO | 55% |
| 190 | 4.0 | 8% | P0.4R8 | 0.4 | 7.7 | 9 | 67 | 32% | dP2R3 | 2.0 | 2.8 | 45 | 125 | DMSO | 55% |
| 191 | 4.0 | 8% | P0.6R2 | 0.6 | 1.9 | 13 | 26 | 32% | dP0.2R6 | 0.2 | 5.8 | 3 | 17 | DMSO | 55% |
| 192 | 4.0 | 8% | P0.6R2 | 0.6 | 1.9 | 13 | 26 | 32% | dP0.4R6 | 0.4 | 5.8 | 7 | 42 | DMSO | 55% |
| 193 | 4.0 | 8% | P0.6R2 | 0.6 | 1.9 | 13 | 26 | 32% | dP0.6R5 | 0.6 | 4.6 | 12 | 54 | DMSO | 55% |
| 194 | 4.0 | 8% | P0.6R2 | 0.6 | 1.9 | 13 | 26 | 32% | dP1R4 | 1.0 | 4.0 | 22 | 89 | DMSO | 55% |
| 195 | 4.0 | 8% | P0.6R2 | 0.6 | 1.9 | 13 | 26 | 32% | dP2R3 | 2.0 | 2.8 | 45 | 125 | DMSO | 55% |
| 196 | 4.0 | 8% | P0.6R4 | 0.6 | 4.2 | 13 | 55 | 32% | dP0.2R6 | 0.2 | 5.8 | 3 | 17 | DMSO | 55% |
| 197 | 4.0 | 8% | P0.6R4 | 0.6 | 4.2 | 13 | 55 | 32% | dP0.4R6 | 0.4 | 5.8 | 7 | 42 | DMSO | 55% |
| 198 | 4.0 | 8% | P0.6R4 | 0.6 | 4.2 | 13 | 55 | 32% | dP0.6R5 | 0.6 | 4.6 | 12 | 54 | DMSO | 55% |
| 199 | 4.0 | 8% | P0.6R4 | 0.6 | 4.2 | 13 | 55 | 32% | dP1R4 | 1.0 | 4.0 | 22 | 89 | DMSO | 55% |
| 200 | 4.0 | 8% | P0.6R4 | 0.6 | 4.2 | 13 | 55 | 32% | dP2R3 | 2.0 | 2.8 | 45 | 125 | DMSO | 55% |
| 201 | 4.0 | 8% | P1R2 | 1.0 | 2.1 | 22 | 47 | 32% | dP0.2R6 | 0.2 | 5.8 | 3 | 17 | DMSO | 55% |
| 202 | 4.0 | 8% | P1R2 | 1.0 | 2.1 | 22 | 47 | 32% | dP0.4R6 | 0.4 | 5.8 | 7 | 42 | DMSO | 55% |
| 203 | 4.0 | 8% | P1R2 | 1.0 | 2.1 | 22 | 47 | 32% | dP0.6R5 | 0.6 | 4.6 | 12 | 54 | DMSO | 55% |
| 204 | 4.0 | 8% | P1R2 | 1.0 | 2.1 | 22 | 47 | 32% | dP1R4 | 1.0 | 4.0 | 22 | 89 | DMSO | 55% |
| 205 | 4.0 | 8% | P1R2 | 1.0 | 2.1 | 22 | 47 | 32% | dP2R3 | 2.0 | 2.8 | 45 | 125 | DMSO | 55% |
| 206 | 4.0 | 8% | P1R4 | 1.0 | 4.0 | 22 | 88 | 32% | dP0.2R6 | 0.2 | 5.8 | 3 | 17 | DMSO | 55% |
| 207 | 4.0 | 8% | P1R4 | 1.0 | 4.0 | 22 | 88 | 32% | dP0.4R6 | 0.4 | 5.8 | 7 | 42 | DMSO | 55% |
| 208 | 4.0 | 8% | P1R4 | 1.0 | 4.0 | 22 | 88 | 32% | dP0.6R5 | 0.6 | 4.6 | 12 | 54 | DMSO | 55% |
| 209 | 4.0 | 8% | P1R4 | 1.0 | 4.0 | 22 | 88 | 32% | dP1R4 | 1.0 | 4.0 | 22 | 89 | DMSO | 55% |
| 210 | 4.0 | 8% | P1R4 | 1.0 | 4.0 | 22 | 88 | 32% | dP2R3 | 2.0 | 2.8 | 45 | 125 | DMSO | 55% |
| 211 | 4.0 | 8% | P2R2 | 2.0 | 2.0 | 45 | 88 | 32% | dP0.2R6 | 0.2 | 5.8 | 3 | 17 | DMSO | 55% |
| 212 | 4.0 | 8% | P2R2 | 2.0 | 2.0 | 45 | 88 | 32% | dP0.4R6 | 0.4 | 5.8 | 7 | 42 | DMSO | 55% |
| 213 | 4.0 | 8% | P2R2 | 2.0 | 2.0 | 45 | 88 | 32% | dP0.6R5 | 0.6 | 4.6 | 12 | 54 | DMSO | 55% |
| 214 | 4.0 | 8% | P2R2 | 2.0 | 2.0 | 45 | 88 | 32% | dP1R4 | 1.0 | 4.0 | 22 | 89 | DMSO | 55% |
| 215 | 4.0 | 8% | P2R2 | 2.0 | 2.0 | 45 | 88 | 32% | dP2R3 | 2.0 | 2.8 | 45 | 125 | DMSO | 55% |
| 216 | 4.0 | 8% | P2R5 | 2.0 | 4.8 | 45 | 216 | 32% | dP0.2R6 | 0.2 | 5.8 | 3 | 17 | DMSO | 55% |
| 217 | 4.0 | 8% | P2R5 | 2.0 | 4.8 | 45 | 216 | 32% | dP0.4R6 | 0.4 | 5.8 | 7 | 42 | DMSO | 55% |
| 218 | 4.0 | 8% | P2R5 | 2.0 | 4.8 | 45 | 216 | 32% | dP0.6R5 | 0.6 | 4.6 | 12 | 54 | DMSO | 55% |
| 219 | 4.0 | 8% | P2R5 | 2.0 | 4.8 | 45 | 216 | 32% | dP1R4 | 1.0 | 4.0 | 22 | 89 | DMSO | 55% |
| 220 | 4.0 | 8% | P2R5 | 2.0 | 4.8 | 45 | 216 | 32% | dP2R3 | 2.0 | 2.8 | 45 | 125 | DMSO | 55% |
| 221 | 4.0 | 8% | P3R1 | 3.0 | 1.0 | 68 | 66 | 32% | dP0.2R6 | 0.2 | 5.8 | 3 | 17 | DMSO | 55% |
| 222 | 4.0 | 8% | P3R1 | 3.0 | 1.0 | 68 | 66 | 32% | dP0.4R6 | 0.4 | 5.8 | 7 | 42 | DMSO | 55% |
| 223 | 4.0 | 8% | P3R1 | 3.0 | 1.0 | 68 | 66 | 32% | dP0.6R5 | 0.6 | 4.6 | 12 | 54 | DMSO | 55% |
| 224 | 4.0 | 8% | P3R1 | 3.0 | 1.0 | 68 | 66 | 32% | dP1R4 | 1.0 | 4.0 | 22 | 89 | DMSO | 55% |
| 225 | 4.0 | 8% | P3R1 | 3.0 | 1.0 | 68 | 66 | 32% | dP2R3 | 2.0 | 2.8 | 45 | 125 | DMSO | 55% |
| 226 | 4.0 | 8% | P3R3 | 3.0 | 3.2 | 68 | 218 | 32% | dP0.2R6 | 0.2 | 5.8 | 3 | 17 | DMSO | 55% |
| 227 | 4.0 | 8% | P3R3 | 3.0 | 3.2 | 68 | 218 | 32% | dP0.4R6 | 0.4 | 5.8 | 7 | 42 | DMSO | 55% |
| 228 | 4.0 | 8% | P3R3 | 3.0 | 3.2 | 68 | 218 | 32% | dP0.6R5 | 0.6 | 4.6 | 12 | 54 | DMSO | 55% |
| 229 | 4.0 | 8% | P3R3 | 3.0 | 3.2 | 68 | 218 | 32% | dP1R4 | 1.0 | 4.0 | 22 | 89 | DMSO | 55% |
| 230 | 4.0 | 8% | P3R3 | 3.0 | 3.2 | 68 | 218 | 32% | dP2R3 | 2.0 | 2.8 | 45 | 125 | DMSO | 55% |
| 231 | 4.0 | 8% | P6R0.9 | 6.0 | 0.9 | 136 | 125 | 32% | dP0.2R6 | 0.2 | 5.8 | 3 | 17 | DMSO | 55% |
| 232 | 4.0 | 8% | P6R0.9 | 6.0 | 0.9 | 136 | 125 | 32% | dP0.4R6 | 0.4 | 5.8 | 7 | 42 | DMSO | 55% |
| 233 | 4.0 | 8% | P6R0.9 | 6.0 | 0.9 | 136 | 125 | 32% | dP0.6R5 | 0.6 | 4.6 | 12 | 54 | DMSO | 55% |
| 234 | 4.0 | 8% | P6R0.9 | 6.0 | 0.9 | 136 | 125 | 32% | dP1R4 | 1.0 | 4.0 | 22 | 89 | DMSO | 55% |
| 235 | 4.0 | 8% | P6R0.9 | 6.0 | 0.9 | 136 | 125 | 32% | dP2R3 | 2.0 | 2.8 | 45 | 125 | DMSO | 55% |
| 236 | 4.0 | 8% | P6R2 | 6.0 | 2.0 | 136 | 272 | 32% | dP0.2R6 | 0.2 | 5.8 | 3 | 17 | DMSO | 55% |
| 237 | 4.0 | 8% | P6R2 | 6.0 | 2.0 | 136 | 272 | 32% | dP0.4R6 | 0.4 | 5.8 | 7 | 42 | DMSO | 55% |
| 238 | 4.0 | 8% | P6R2 | 6.0 | 2.0 | 136 | 272 | 32% | dP0.6R5 | 0.6 | 4.6 | 12 | 54 | DMSO | 55% |
| 239 | 4.0 | 8% | P6R2 | 6.0 | 2.0 | 136 | 272 | 32% | dP1R4 | 1.0 | 4.0 | 22 | 89 | DMSO | 55% |
| 240 | 4.0 | 8% | P6R2 | 6.0 | 2.0 | 136 | 272 | 32% | dP2R3 | 2.0 | 2.8 | 45 | 125 | DMSO | 55% |
| 241 | 4.0 | 8% | P0.2R14 | 0.2 | 14.5 | 4 | 58 | 32% | dP0.2R2 | 0.2 | 2.2 | 3 | 7 | DMSO | 55% |
| 242 | 4.0 | 8% | P0.2R14 | 0.2 | 14.5 | 4 | 58 | 32% | dP0.2R13 | 0.2 | 13.0 | 3 | 39 | DMSO | 55% |
| 243 | 4.0 | 8% | P0.2R14 | 0.2 | 14.5 | 4 | 58 | 32% | dP0.4R2 | 0.4 | 2.0 | 7 | 14 | DMSO | 55% |
| 244 | 4.0 | 8% | P0.2R14 | 0.2 | 14.5 | 4 | 58 | 32% | dP0.4R8 | 0.4 | 8.4 | 7 | 61 | DMSO | 55% |
| 245 | 4.0 | 8% | P0.2R14 | 0.2 | 14.5 | 4 | 58 | 32% | dP0.6R3 | 0.6 | 3.0 | 12 | 35 | DMSO | 55% |
| 246 | 4.0 | 8% | P0.2R14 | 0.2 | 14.5 | 4 | 58 | 32% | dP0.6R5 | 0.6 | 5.1 | 12 | 60 | DMSO | 55% |
| 247 | 4.0 | 8% | P0.2R14 | 0.2 | 14.5 | 4 | 58 | 32% | dP1R3 | 1.0 | 3.0 | 22 | 66 | DMSO | 55% |
| 248 | 4.0 | 8% | P0.2R14 | 0.2 | 14.5 | 4 | 58 | 32% | dP1R5 | 1.0 | 5.4 | 22 | 119 | DMSO | 55% |
| 249 | 4.0 | 8% | P0.2R14 | 0.2 | 14.5 | 4 | 58 | 32% | dP2R1 | 2.0 | 1.3 | 45 | 58 | DMSO | 55% |
| 250 | 4.0 | 8% | P0.2R14 | 0.2 | 14.5 | 4 | 58 | 32% | dP2R5 | 2.0 | 5.3 | 45 | 237 | DMSO | 55% |
| 251 | 4.0 | 8% | P0.6R3 | 0.6 | 3.0 | 13 | 40 | 32% | dP0.2R2 | 0.2 | 2.2 | 3 | 7 | DMSO | 55% |
| 252 | 4.0 | 8% | P0.6R3 | 0.6 | 3.0 | 13 | 40 | 32% | dP0.2R13 | 0.2 | 13.0 | 3 | 39 | DMSO | 55% |
| 253 | 4.0 | 8% | P0.6R3 | 0.6 | 3.0 | 13 | 40 | 32% | dP0.4R2 | 0.4 | 2.0 | 7 | 14 | DMSO | 55% |
| 254 | 4.0 | 8% | P0.6R3 | 0.6 | 3.0 | 13 | 40 | 32% | dP0.4R8 | 0.4 | 8.4 | 7 | 61 | DMSO | 55% |
| 255 | 4.0 | 8% | P0.6R3 | 0.6 | 3.0 | 13 | 40 | 32% | dP0.6R3 | 0.6 | 3.0 | 12 | 35 | DMSO | 55% |
| 256 | 4.0 | 8% | P0.6R3 | 0.6 | 3.0 | 13 | 40 | 32% | dP0.6R5 | 0.6 | 5.1 | 12 | 60 | DMSO | 55% |
| 257 | 4.0 | 8% | P0.6R3 | 0.6 | 3.0 | 13 | 40 | 32% | dP1R3 | 1.0 | 3.0 | 22 | 66 | DMSO | 55% |
| 258 | 4.0 | 8% | P0.6R3 | 0.6 | 3.0 | 13 | 40 | 32% | dP1R5 | 1.0 | 5.4 | 22 | 119 | DMSO | 55% |
| 259 | 4.0 | 8% | P0.6R3 | 0.6 | 3.0 | 13 | 40 | 32% | dP2R1 | 2.0 | 1.3 | 45 | 58 | DMSO | 55% |
| 260 | 4.0 | 8% | P0.6R3 | 0.6 | 3.0 | 13 | 40 | 32% | dP2R5 | 2.0 | 5.3 | 45 | 237 | DMSO | 55% |

TABLE 2-continued

| Exp | Ratio | Triblock copolymer (TB) | | | | | | Diblock copolymer (DB) | | | | | | Solvent | |
|---|---|---|---|---|---|---|---|---|---|---|---|---|---|---|---|
| n° | DB/TB | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 261 | 4.0 | 8% | P1R3 | 1.0 | 3.1 | 22 | 68 | 32% | dP0.2R2 | 0.2 | 2.2 | 3 | 7 | DMSO | 55% |
| 262 | 4.0 | 8% | P1R3 | 1.0 | 3.1 | 22 | 68 | 32% | dP0.2R13 | 0.2 | 13.0 | 3 | 39 | DMSO | 55% |
| 263 | 4.0 | 8% | P1R3 | 1.0 | 3.1 | 22 | 68 | 32% | dP0.4R2 | 0.4 | 2.0 | 7 | 14 | DMSO | 55% |
| 264 | 4.0 | 8% | P1R3 | 1.0 | 3.1 | 22 | 68 | 32% | dP0.4R8 | 0.4 | 8.4 | 7 | 61 | DMSO | 55% |
| 265 | 4.0 | 8% | P1R3 | 1.0 | 3.1 | 22 | 68 | 32% | dP0.6R3 | 0.6 | 3.0 | 12 | 35 | DMSO | 55% |
| 266 | 4.0 | 8% | P1R3 | 1.0 | 3.1 | 22 | 68 | 32% | dP0.6R5 | 0.6 | 5.1 | 12 | 60 | DMSO | 55% |
| 267 | 4.0 | 8% | P1R3 | 1.0 | 3.1 | 22 | 68 | 32% | dP1R3 | 1.0 | 3.0 | 22 | 66 | DMSO | 55% |
| 268 | 4.0 | 8% | P1R3 | 1.0 | 3.1 | 22 | 68 | 32% | dP1R5 | 1.0 | 5.4 | 22 | 119 | DMSO | 55% |
| 269 | 4.0 | 8% | P1R3 | 1.0 | 3.1 | 22 | 68 | 32% | dP2R1 | 2.0 | 1.3 | 45 | 58 | DMSO | 55% |
| 270 | 4.0 | 8% | P1R3 | 1.0 | 3.1 | 22 | 68 | 32% | dP2R5 | 2.0 | 5.3 | 45 | 237 | DMSO | 55% |
| 271 | 4.0 | 8% | P2R3 | 2.0 | 3.5 | 45 | 157 | 32% | dP0.2R2 | 0.2 | 2.2 | 3 | 7 | DMSO | 55% |
| 272 | 4.0 | 8% | P2R3 | 2.0 | 3.5 | 45 | 157 | 32% | dP0.2R13 | 0.2 | 13.0 | 3 | 39 | DMSO | 55% |
| 273 | 4.0 | 8% | P2R3 | 2.0 | 3.5 | 45 | 157 | 32% | dP0.4R2 | 0.4 | 2.0 | 7 | 14 | DMSO | 55% |
| 274 | 4.0 | 8% | P2R3 | 2.0 | 3.5 | 45 | 157 | 32% | dP0.4R8 | 0.4 | 8.4 | 7 | 61 | DMSO | 55% |
| 275 | 4.0 | 8% | P2R3 | 2.0 | 3.5 | 45 | 157 | 32% | dP0.6R3 | 0.6 | 3.0 | 12 | 35 | DMSO | 55% |
| 276 | 4.0 | 8% | P2R3 | 2.0 | 3.5 | 45 | 157 | 32% | dP0.6R5 | 0.6 | 5.1 | 12 | 60 | DMSO | 55% |
| 277 | 4.0 | 8% | P2R3 | 2.0 | 3.5 | 45 | 157 | 32% | dP1R3 | 1.0 | 3.0 | 22 | 66 | DMSO | 55% |
| 278 | 4.0 | 8% | P2R3 | 2.0 | 3.5 | 45 | 157 | 32% | dP1R5 | 1.0 | 5.4 | 22 | 119 | DMSO | 55% |
| 279 | 4.0 | 8% | P2R3 | 2.0 | 3.5 | 45 | 157 | 32% | dP2R1 | 2.0 | 1.3 | 45 | 58 | DMSO | 55% |
| 280 | 4.0 | 8% | P2R3 | 2.0 | 3.5 | 45 | 157 | 32% | dP2R5 | 2.0 | 5.3 | 45 | 237 | DMSO | 55% |
| 281 | 4.0 | 8% | P3R2 | 3.0 | 2.3 | 68 | 154 | 32% | dP0.2R2 | 0.2 | 2.2 | 3 | 7 | DMSO | 55% |
| 282 | 4.0 | 8% | P3R2 | 3.0 | 2.3 | 68 | 154 | 32% | dP0.2R13 | 0.2 | 13.0 | 3 | 39 | DMSO | 55% |
| 283 | 4.0 | 8% | P3R2 | 3.0 | 2.3 | 68 | 154 | 32% | dP0.4R2 | 0.4 | 2.0 | 7 | 14 | DMSO | 55% |
| 284 | 4.0 | 8% | P3R2 | 3.0 | 2.3 | 68 | 154 | 32% | dP0.4R8 | 0.4 | 8.4 | 7 | 61 | DMSO | 55% |
| 285 | 4.0 | 8% | P3R2 | 3.0 | 2.3 | 68 | 154 | 32% | dP0.6R3 | 0.6 | 3.0 | 12 | 35 | DMSO | 55% |
| 286 | 4.0 | 8% | P3R2 | 3.0 | 2.3 | 68 | 154 | 32% | dP0.6R5 | 0.6 | 5.1 | 12 | 60 | DMSO | 55% |
| 287 | 4.0 | 8% | P3R2 | 3.0 | 2.3 | 68 | 154 | 32% | dP1R3 | 1.0 | 3.0 | 22 | 66 | DMSO | 55% |
| 288 | 4.0 | 8% | P3R2 | 3.0 | 2.3 | 68 | 154 | 32% | dP1R5 | 1.0 | 5.4 | 22 | 119 | DMSO | 55% |
| 289 | 4.0 | 8% | P3R2 | 3.0 | 2.3 | 68 | 154 | 32% | dP2R1 | 2.0 | 1.3 | 45 | 58 | DMSO | 55% |
| 290 | 4.0 | 8% | P3R2 | 3.0 | 2.3 | 68 | 154 | 32% | dP2R5 | 2.0 | 5.3 | 45 | 237 | DMSO | 55% |
| 291 | 4.0 | 8% | P6R2 | 6.0 | 1.6 | 136 | 218 | 32% | dP0.2R2 | 0.2 | 2.2 | 3 | 7 | DMSO | 55% |
| 292 | 4.0 | 8% | P6R2 | 6.0 | 1.6 | 136 | 218 | 32% | dP0.2R13 | 0.2 | 13.0 | 3 | 39 | DMSO | 55% |
| 293 | 4.0 | 8% | P6R2 | 6.0 | 1.6 | 136 | 218 | 32% | dP0.4R2 | 0.4 | 2.0 | 7 | 14 | DMSO | 55% |
| 294 | 4.0 | 8% | P6R2 | 6.0 | 1.6 | 136 | 218 | 32% | dP0.4R8 | 0.4 | 8.4 | 7 | 61 | DMSO | 55% |
| 295 | 4.0 | 8% | P6R2 | 6.0 | 1.6 | 136 | 218 | 32% | dP0.6R3 | 0.6 | 3.0 | 12 | 35 | DMSO | 55% |
| 296 | 4.0 | 8% | P6R2 | 6.0 | 1.6 | 136 | 218 | 32% | dP0.6R5 | 0.6 | 5.1 | 12 | 60 | DMSO | 55% |
| 297 | 4.0 | 8% | P6R2 | 6.0 | 1.6 | 136 | 218 | 32% | dP1R3 | 1.0 | 3.0 | 22 | 66 | DMSO | 55% |
| 298 | 4.0 | 8% | P6R2 | 6.0 | 1.6 | 136 | 218 | 32% | dP1R5 | 1.0 | 5.4 | 22 | 119 | DMSO | 55% |
| 299 | 4.0 | 8% | P6R2 | 6.0 | 1.6 | 136 | 218 | 32% | dP2R1 | 2.0 | 1.3 | 45 | 58 | DMSO | 55% |
| 300 | 4.0 | 8% | P6R2 | 6.0 | 1.6 | 136 | 218 | 32% | dP2R5 | 2.0 | 5.3 | 45 | 237 | DMSO | 55% |
| 301 | 0.0 | 40% | P2R3 | 2.0 | 3.5 | 45 | 157 | 0% | dP0.4R6 | 0.4 | 5.8 | 7 | 42 | DMSO | 55% |
| 302 | 0.05 | 38% | P2R3 | 2.0 | 3.5 | 45 | 157 | 2% | dP0.4R6 | 0.4 | 5.8 | 7 | 42 | DMSO | 55% |
| 303 | 0.11 | 36% | P2R3 | 2.0 | 3.5 | 45 | 157 | 4% | dP0.4R6 | 0.4 | 5.8 | 7 | 42 | DMSO | 55% |
| 304 | 0.25 | 32% | P2R3 | 2.0 | 3.5 | 45 | 157 | 8% | dP0.4R6 | 0.4 | 5.8 | 7 | 42 | DMSO | 55% |
| 305 | 1.00 | 20% | P2R3 | 2.0 | 3.5 | 45 | 157 | 20% | dP0.4R6 | 0.4 | 5.8 | 7 | 42 | DMSO | 55% |
| 306 | 4.0 | 8% | P2R3 | 2.0 | 3.5 | 45 | 157 | 32% | dP0.4R6 | 0.4 | 5.8 | 7 | 42 | DMSO | 55% |
| 307 | 9.0 | 4% | P2R3 | 2.0 | 3.5 | 45 | 157 | 36% | dP0.4R6 | 0.4 | 5.8 | 7 | 42 | DMSO | 55% |
| 308 | 19.0 | 2% | P2R3 | 2.0 | 3.5 | 45 | 157 | 38% | dP0.4R6 | 0.4 | 5.8 | 7 | 42 | DMSO | 55% |
| 309 | ∞ | 0% | P2R3 | 2.0 | 3.5 | 45 | 157 | 40% | dP0.4R6 | 0.4 | 5.8 | 7 | 42 | DMSO | 55% |
| 310 | 0.0 | 40% | P2R3 | 2.0 | 3.5 | 45 | 157 | 0% | dP0.6R5 | 0.6 | 4.6 | 12 | 54 | DMSO | 55% |
| 311 | 0.05 | 38% | P2R3 | 2.0 | 3.5 | 45 | 157 | 2% | dP0.6R5 | 0.6 | 4.6 | 12 | 54 | DMSO | 55% |
| 312 | 0.11 | 36% | P2R3 | 2.0 | 3.5 | 45 | 157 | 4% | dP0.6R5 | 0.6 | 4.6 | 12 | 54 | DMSO | 55% |
| 313 | 0.25 | 32% | P2R3 | 2.0 | 3.5 | 45 | 157 | 8% | dP0.6R5 | 0.6 | 4.6 | 12 | 54 | DMSO | 55% |
| 314 | 1.00 | 20% | P2R3 | 2.0 | 3.5 | 45 | 157 | 20% | dP0.6R5 | 0.6 | 4.6 | 12 | 54 | DMSO | 55% |
| 315 | 4.0 | 8% | P2R3 | 2.0 | 3.5 | 45 | 157 | 32% | dP0.6R5 | 0.6 | 4.6 | 12 | 54 | DMSO | 55% |
| 316 | 9.0 | 4% | P2R3 | 2.0 | 3.5 | 45 | 157 | 36% | dP0.6R5 | 0.6 | 4.6 | 12 | 54 | DMSO | 55% |
| 317 | 19.0 | 2% | P2R3 | 2.0 | 3.5 | 45 | 157 | 38% | dP0.6R5 | 0.6 | 4.6 | 12 | 54 | DMSO | 55% |
| 318 | ∞ | 0% | P2R3 | 2.0 | 3.5 | 45 | 157 | 40% | dP0.6R5 | 0.6 | 4.6 | 12 | 54 | DMSO | 55% |
| 319 | 0.0 | 40% | P0.4R8 | 0.4 | 7.7 | 9 | 67 | 0% | dP0.4R8 | 0.4 | 8.4 | 7 | 61 | DMSO | 55% |
| 320 | 0.05 | 38% | P0.4R8 | 0.4 | 7.7 | 9 | 67 | 2% | dP0.4R8 | 0.4 | 8.4 | 7 | 61 | DMSO | 55% |
| 321 | 0.11 | 36% | P0.4R8 | 0.4 | 7.7 | 9 | 67 | 4% | dP0.4R8 | 0.4 | 8.4 | 7 | 61 | DMSO | 55% |
| 322 | 0.25 | 32% | P0.4R8 | 0.4 | 7.7 | 9 | 67 | 8% | dP0.4R8 | 0.4 | 8.4 | 7 | 61 | DMSO | 55% |
| 323 | 1.00 | 20% | P0.4R8 | 0.4 | 7.7 | 9 | 67 | 20% | dP0.4R8 | 0.4 | 8.4 | 7 | 61 | DMSO | 55% |
| 324 | 4.0 | 8% | P0.4R8 | 0.4 | 7.7 | 9 | 67 | 32% | dP0.4R8 | 0.4 | 8.4 | 7 | 61 | DMSO | 55% |
| 325 | 9.0 | 4% | P0.4R8 | 0.4 | 7.7 | 9 | 67 | 36% | dP0.4R8 | 0.4 | 8.4 | 7 | 61 | DMSO | 55% |
| 326 | 19.0 | 2% | P0.4R8 | 0.4 | 7.7 | 9 | 67 | 38% | dP0.4R8 | 0.4 | 8.4 | 7 | 61 | DMSO | 55% |
| 327 | ∞ | 0% | P0.4R8 | 0.4 | 7.7 | 9 | 67 | 40% | dP0.4R8 | 0.4 | 8.4 | 7 | 61 | DMSO | 55% |
| 328 | 0.0 | 40% | P1R2 | 1.0 | 2.1 | 22 | 47 | 0% | dP0.6R5 | 0.6 | 5.1 | 12 | 60 | DMSO | 55% |
| 329 | 0.05 | 38% | P1R2 | 1.0 | 2.1 | 22 | 47 | 2% | dP0.6R5 | 0.6 | 5.1 | 12 | 60 | DMSO | 55% |
| 330 | 0.11 | 36% | P1R2 | 1.0 | 2.1 | 22 | 47 | 4% | dP0.6R5 | 0.6 | 5.1 | 12 | 60 | DMSO | 55% |
| 331 | 0.25 | 32% | P1R2 | 1.0 | 2.1 | 22 | 47 | 8% | dP0.6R5 | 0.6 | 5.1 | 12 | 60 | DMSO | 55% |
| 332 | 1.00 | 20% | P1R2 | 1.0 | 2.1 | 22 | 47 | 20% | dP0.6R5 | 0.6 | 5.1 | 12 | 60 | DMSO | 55% |
| 333 | 4.0 | 8% | P1R2 | 1.0 | 2.1 | 22 | 47 | 32% | dP0.6R5 | 0.6 | 5.1 | 12 | 60 | DMSO | 55% |
| 334 | 9.0 | 4% | P1R2 | 1.0 | 2.1 | 22 | 47 | 36% | dP0.6R5 | 0.6 | 5.1 | 12 | 60 | DMSO | 55% |

TABLE 2-continued

| | | Triblock copolymer (TB) | | | | | | Diblock copolymer (DB) | | | | | | Solvent | |
|---|---|---|---|---|---|---|---|---|---|---|---|---|---|---|---|
| Exp n° | Ratio DB/TB | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 335 | 19.0 | 2% | P1R2 | 1.0 | 2.1 | 22 | 47 | 38% | dP0.6R5 | 0.6 | 5.1 | 12 | 60 | DMSO | 55% |
| 336 | ∞ | 0% | P1R2 | 1.0 | 2.1 | 22 | 47 | 40% | dP0.6R5 | 0.6 | 5.1 | 12 | 60 | DMSO | 55% |
| 337 | 0.0 | 40% | P2R5 | 2.0 | 4.8 | 45 | 216 | 0% | dP0.2R13 | 0.2 | 13.0 | 3 | 39 | DMSO | 55% |
| 338 | 0.05 | 38% | P2R5 | 2.0 | 4.8 | 45 | 216 | 2% | dP0.2R13 | 0.2 | 13.0 | 3 | 39 | DMSO | 55% |
| 339 | 0.11 | 36% | P2R5 | 2.0 | 4.8 | 45 | 216 | 4% | dP0.2R13 | 0.2 | 13.0 | 3 | 39 | DMSO | 55% |
| 340 | 0.25 | 32% | P2R5 | 2.0 | 4.8 | 45 | 216 | 8% | dP0.2R13 | 0.2 | 13.0 | 3 | 39 | DMSO | 55% |
| 341 | 1.00 | 20% | P2R5 | 2.0 | 4.8 | 45 | 216 | 20% | dP0.2R13 | 0.2 | 13.0 | 3 | 39 | DMSO | 55% |
| 342 | 4.0 | 8% | P2R5 | 2.0 | 4.8 | 45 | 216 | 32% | dP0.2R13 | 0.2 | 13.0 | 3 | 39 | DMSO | 55% |
| 343 | 9.0 | 4% | P2R5 | 2.0 | 4.8 | 45 | 216 | 36% | dP0.2R13 | 0.2 | 13.0 | 3 | 39 | DMSO | 55% |
| 344 | 19.0 | 2% | P2R5 | 2.0 | 4.8 | 45 | 216 | 38% | dP0.2R13 | 0.2 | 13.0 | 3 | 39 | DMSO | 55% |
| 345 | ∞ | 0% | P2R5 | 2.0 | 4.8 | 45 | 216 | 40% | dP0.2R13 | 0.2 | 13.0 | 3 | 39 | DMSO | 55% |

Example 5

Buprenorphine's Formulations Preparation

The formulations described herein were based on organic solution of polymers prepared as in Example 1, containing as the drug, buprenorphine. Typically, 0.4 grams of polymers, corresponding to a mix of a diblock copolymer and a triblock copolymer in defined mass ratio, were dissolved in 0.5 grams of dimethyl sulfoxide at room temperature overnight under constant magnetic stirring. The next day, 100 mg of buprenorphine was added to the polymer solution and stirred until complete dissolution. The formulations were loaded in a syringe before use.

Three different formulations were selected for in vivo experiments. The composition of these formulations is shown in Table 3 below. The formulations were injected subcutaneously in the interscapular space of male rats (200-250 gr) at a final dose of 100 mg/kg of buprenorphine. Blood samples were withdraw periodically and analyzed for buprenorphine concentrations by LC/MS/MS.

The formulations are shown in Table 3 below.

TABLE 3

| | | Triblock copolymer (TB) | | | | | | Diblock copolymer (DB) | | | | | | Solvent | |
|---|---|---|---|---|---|---|---|---|---|---|---|---|---|---|---|
| Exp n° | Ratio DB/TB | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 1 | 4.0 | 10.0% | P0.4R8 | 0.4 | 7.7 | 9 | 70 | 40.0% | dP0.4R10 | 0.35 | 9.8 | 8 | 78 | DMSO | 40.0% |
| 2 | 4.0 | 10.0% | P2R2 | 2 | 2.2 | 45 | 101 | 40.0% | dP0.4R10 | 0.35 | 9.8 | 8 | 78 | DMSO | 40.0% |
| 3 | 4.0 | 10.0% | P2R3 | 2 | 3.3 | 45 | 150 | 40.0% | dP0.4R10 | 0.35 | 9.8 | 8 | 78 | DMSO | 40.0% |
| 4 | 4.0 | 10.0% | P2R4 | 2 | 4.3 | 45 | 195 | 40.0% | dP0.4R10 | 0.35 | 9.8 | 8 | 78 | DMSO | 40.0% |
| 5 | 4.0 | 10.0% | P0.4R8 | 0.4 | 7.7 | 9 | 70 | 40.0% | dP1R4 | 1 | 4.2 | 23 | 95 | DMSO | 40.0% |
| 6 | 4.0 | 10.0% | P2R2 | 2 | 2.2 | 45 | 101 | 40.0% | dP1R4 | 1 | 4.2 | 23 | 95 | DMSO | 40.0% |
| 7 | 4.0 | 10.0% | P2R3 | 2 | 3.3 | 45 | 150 | 40.0% | dP1R4 | 1 | 4.2 | 23 | 95 | DMSO | 40.0% |
| 8 | 4.0 | 10.0% | P2R4 | 2 | 4.3 | 45 | 195 | 40.0% | dP1R4 | 1 | 4.2 | 23 | 95 | DMSO | 40.0% |
| 9 | 4.0 | 10.0% | P0.4R8 | 0.4 | 7.7 | 9 | 70 | 40.0% | dP1R5 | 1 | 5.4 | 23 | 123 | DMSO | 40.0% |
| 10 | 4.0 | 10.0% | P2R2 | 2 | 2.2 | 45 | 101 | 40.0% | dP1R5 | 1 | 5.4 | 23 | 123 | DMSO | 40.0% |
| 11 | 4.0 | 10.0% | P2R3 | 2 | 3.3 | 45 | 150 | 40.0% | dP1R5 | 1 | 5.4 | 23 | 123 | DMSO | 40.0% |
| 12 | 4.0 | 10.0% | P2R4 | 2 | 4.3 | 45 | 195 | 40.0% | dP1R5 | 1 | 5.4 | 23 | 123 | DMSO | 40.0% |
| 13 | 4.0 | 10.0% | P0.4R8 | 0.4 | 7.7 | 9 | 70 | 40.0% | dP2R3 | 2 | 2.7 | 45 | 120 | DMSO | 40.0% |
| 14 | 4.0 | 10.0% | P2R2 | 2 | 2.2 | 45 | 101 | 40.0% | dP2R3 | 2 | 2.7 | 45 | 120 | DMSO | 40.0% |
| 15 | 4.0 | 10.0% | P2R3 | 2 | 3.3 | 45 | 150 | 40.0% | dP2R3 | 2 | 2.7 | 45 | 120 | DMSO | 40.0% |
| 16 | 4.0 | 10.0% | P2R4 | 2 | 4.3 | 45 | 195 | 40.0% | dP2R3 | 2 | 2.7 | 45 | 120 | DMSO | 40.0% |
| 17 | 4.0 | 10.0% | P0.4R8 | 0.4 | 7.7 | 9 | 70 | 40.0% | dP2R4 | 2 | 4.1 | 45 | 186 | DMSO | 40.0% |
| 18 | 4.0 | 10.0% | P2R2 | 2 | 2.2 | 45 | 101 | 40.0% | dP2R4 | 2 | 4.1 | 45 | 186 | DMSO | 40.0% |
| 19 | 4.0 | 10.0% | P2R3 | 2 | 3.3 | 45 | 150 | 40.0% | dP2R4 | 2 | 4.1 | 45 | 186 | DMSO | 40.0% |
| 20 | 4.0 | 10.0% | P2R4 | 2 | 4.3 | 45 | 195 | 40.0% | dP2R4 | 2 | 4.1 | 45 | 186 | DMSO | 40.0% |
| 21 | 4.0 | 10.0% | P0.4R8 | 0.4 | 7.7 | 9 | 70 | 40.0% | dP2R5 | 2 | 5.3 | 45 | 241 | DMSO | 40.0% |
| 22 | 4.0 | 10.0% | P2R2 | 2 | 2.2 | 45 | 101 | 40.0% | dP2R5 | 2 | 5.3 | 45 | 241 | DMSO | 40.0% |
| 23 | 4.0 | 10.0% | P2R3 | 2 | 3.3 | 45 | 150 | 40.0% | dP2R5 | 2 | 5.3 | 45 | 241 | DMSO | 40.0% |
| 24 | 4.0 | 10.0% | P2R4 | 2 | 4.3 | 45 | 195 | 40.0% | dP2R5 | 2 | 5.3 | 45 | 241 | DMSO | 40.0% |
| 26 | 4.0 | 9.0% | P0.4R8 | 0.4 | 7.7 | 9 | 70 | 36.0% | dP0.4R10 | 0.35 | 9.8 | 8 | 78 | DMSO | 45.0% |
| 27 | 4.0 | 9.0% | P2R2 | 2 | 2.2 | 45 | 101 | 36.0% | dP0.4R10 | 0.35 | 9.8 | 8 | 78 | DMSO | 45.0% |
| 28 | 4.0 | 9.0% | P2R3 | 2 | 3.3 | 45 | 150 | 36.0% | dP0.4R10 | 0.35 | 9.8 | 8 | 78 | DMSO | 45.0% |
| 29 | 4.0 | 9.0% | P0.4R8 | 0.4 | 7.7 | 9 | 70 | 36.0% | dP1R4 | 1 | 4.2 | 23 | 95 | DMSO | 45.0% |
| 30 | 4.0 | 9.0% | P2R2 | 2 | 2.2 | 45 | 101 | 36.0% | dP1R4 | 1 | 4.2 | 23 | 95 | DMSO | 45.0% |
| 31 | 4.0 | 9.0% | P2R2 | 2 | 2.2 | 45 | 101 | 36.0% | dP2R3 | 2 | 2.7 | 45 | 120 | DMSO | 45.0% |
| 32 | 4.0 | 8.0% | P0.4R8 | 0.4 | 7.7 | 9 | 70 | 32.0% | dP0.4R10 | 0.35 | 9.8 | 8 | 78 | DMSO | 50.0% |
| 33 | 4.0 | 8.0% | P2R2 | 2 | 2.2 | 45 | 101 | 32.0% | dP0.4R10 | 0.35 | 9.8 | 8 | 78 | DMSO | 50.0% |
| 34 | 4.0 | 8.0% | P2R3 | 2 | 3.3 | 45 | 150 | 32.0% | dP0.4R10 | 0.35 | 9.8 | 8 | 78 | DMSO | 50.0% |
| 35 | 4.0 | 8.0% | P0.4R8 | 0.4 | 7.7 | 9 | 70 | 32.0% | dP1R4 | 1 | 4.2 | 23 | 95 | DMSO | 50.0% |
| 36 | 4.0 | 8.0% | P2R2 | 2 | 2.2 | 45 | 101 | 32.0% | dP1R4 | 1 | 4.2 | 23 | 95 | DMSO | 50.0% |

TABLE 3-continued

| | | Triblock copolymer (TB) | | | | | | Diblock copolymer (DB) | | | | | | Solvent | |
|---|---|---|---|---|---|---|---|---|---|---|---|---|---|---|---|
| Exp n° | Ratio DB/TB | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 37 | 4.0 | 8.0% | P2R2 | 2 | 2.2 | 45 | 101 | 32.0% | dP2R3 | 2 | 2.7 | 45 | 120 | DMSO | 50.0% |
| 38 | 4.0 | 10.0% | P0.4R8 | 0.4 | 7.7 | 9 | 70 | 40.0% | dP1R3 | 1 | 2.7 | 23 | 61 | DMSO | 40.0% |
| 39 | 4.0 | 10.0% | P2R2 | 2 | 2.2 | 45 | 101 | 40.0% | dP1R3 | 1 | 2.7 | 23 | 61 | DMSO | 40.0% |
| 40 | 4.0 | 10.0% | P2R3 | 2 | 3.3 | 45 | 150 | 40.0% | dP1R3 | 1 | 2.7 | 23 | 61 | DMSO | 40.0% |
| 41 | 4.0 | 10.0% | P2R4 | 2 | 4.3 | 45 | 195 | 40.0% | dP1R3 | 1 | 2.7 | 23 | 61 | DMSO | 40.0% |
| 42 | 4.0 | 9.0% | P0.4R8 | 0.4 | 7.7 | 9 | 70 | 36.0% | dP1R3 | 1 | 2.7 | 23 | 61 | DMSO | 45.0% |
| 43 | 4.0 | 9.0% | P2R2 | 2 | 2.2 | 45 | 101 | 36.0% | dP1R3 | 1 | 2.7 | 23 | 61 | DMSO | 45.0% |
| 44 | 4.0 | 9.0% | P2R3 | 2 | 3.3 | 45 | 150 | 36.0% | dP1R3 | 1 | 2.7 | 23 | 61 | DMSO | 45.0% |
| 45 | 4.0 | 9.0% | P2R4 | 2 | 4.3 | 45 | 195 | 36.0% | dP1R3 | 1 | 2.7 | 23 | 61 | DMSO | 45.0% |
| 46 | 4.0 | 8.0% | P0.4R8 | 0.4 | 7.7 | 9 | 70 | 32.0% | dP1R3 | 1 | 2.7 | 23 | 61 | DMSO | 50.0% |
| 47 | 4.0 | 8.0% | P2R2 | 2 | 2.2 | 45 | 101 | 32.0% | dP1R3 | 1 | 2.7 | 23 | 61 | DMSO | 50.0% |
| 48 | 4.0 | 8.0% | P2R3 | 2 | 3.3 | 45 | 150 | 32.0% | dP1R3 | 1 | 2.7 | 23 | 61 | DMSO | 50.0% |
| 49 | 4.0 | 8.0% | P2R4 | 2 | 4.3 | 45 | 195 | 32.0% | dP1R3 | 1 | 2.7 | 23 | 61 | DMSO | 50.0% |
| 51 | 4.0 | 10.0% | P2R2 | 2 | 2.2 | 45 | 101 | 40.0% | dP0.4R8 | 0.35 | 7.9 | 8 | 63 | DMSO | 40.0% |
| 52 | 4.0 | 10.0% | P2R2 | 2 | 2.2 | 45 | 101 | 40.0% | dP0.4R5 | 0.35 | 4.9 | 8 | 39 | DMSO | 40.0% |
| 53 | 4.0 | 10.0% | P2R2 | 2 | 2.2 | 45 | 101 | 40.0% | dP1R2 | 1 | 2.1 | 23 | 48 | DMSO | 40.0% |
| 54 | 4.0 | 10.0% | P2R2 | 2 | 2.2 | 45 | 101 | 40.0% | dP2R0.8 | 2 | 0.8 | 45 | 34 | DMSO | 40.0% |
| 55 | 4.0 | 10.0% | P2R2 | 2 | 2.2 | 45 | 101 | 40.0% | dP2R2 | 2 | 1.5 | 45 | 68 | DMSO | 40.0% |
| 56 | 4.0 | 10.0% | P0.4R8 | 0.4 | 7.7 | 9 | 70 | 40.0% | dP0.4R8 | 0.35 | 7.9 | 8 | 63 | DMSO | 40.0% |
| 57 | 4.0 | 10.0% | P0.4R8 | 0.4 | 7.7 | 9 | 70 | 40.0% | dP0.4R5 | 0.35 | 4.9 | 8 | 39 | DMSO | 40.0% |
| 58 | 4.0 | 10.0% | P0.4R8 | 0.4 | 7.7 | 9 | 70 | 40.0% | dP1R2 | 1 | 2.1 | 23 | 48 | DMSO | 40.0% |
| 59 | 4.0 | 10.0% | P0.4R8 | 0.4 | 7.7 | 9 | 70 | 40.0% | dP2R0.8 | 2 | 0.8 | 45 | 34 | DMSO | 40.0% |
| 60 | 4.0 | 10.0% | P0.4R8 | 0.4 | 7.7 | 9 | 70 | 40.0% | dP2R2 | 2 | 1.5 | 45 | 68 | DMSO | 40.0% |
| 61 | 4.0 | 10.0% | P0.4R8 | 0.4 | 7.7 | 9 | 70 | 40.0% | dP0.4R10 | 0.35 | 9.8 | 8 | 78 | DEGMEE | 40.0% |
| 62 | 4.0 | 10.0% | P2R4 | 2 | 4.3 | 45 | 195 | 40.0% | dP0.4R10 | 0.35 | 9.8 | 8 | 78 | DEGMEE | 40.0% |
| 63 | 4.0 | 10.0% | P0.4R8 | 0.4 | 7.7 | 9 | 70 | 40.0% | dP1R3 | 1 | 2.7 | 23 | 61 | DEGMEE | 40.0% |
| 64 | 4.0 | 10.0% | P2R4 | 2 | 4.3 | 45 | 195 | 40.0% | dP1R3 | 1 | 2.7 | 23 | 61 | DEGMEE | 40.0% |
| 65 | 4.0 | 10.0% | P0.4R8 | 0.4 | 7.7 | 9 | 70 | 40.0% | dP2R4 | 2 | 4.1 | 45 | 186 | DEGMEE | 40.0% |
| 66 | 4.0 | 10.0% | P2R4 | 2 | 4.3 | 45 | 195 | 40.0% | dP2R4 | 2 | 4.1 | 45 | 186 | DEGMEE | 40.0% |
| 67 | 4.0 | 10.0% | P0.4R8 | 0.4 | 7.7 | 9 | 70 | 40.0% | dP0.4R10 | 0.35 | 9.8 | 8 | 78 | Diglyme | 40.0% |
| 68 | 4.0 | 10.0% | P2R4 | 2 | 4.3 | 45 | 195 | 40.0% | dP0.4R10 | 0.35 | 9.8 | 8 | 78 | Diglyme | 40.0% |
| 69 | 4.0 | 10.0% | P0.4R8 | 0.4 | 7.7 | 9 | 70 | 40.0% | dP1R3 | 1 | 2.7 | 23 | 61 | Diglyme | 40.0% |
| 70 | 4.0 | 10.0% | P2R4 | 2 | 4.3 | 45 | 195 | 40.0% | dP1R3 | 1 | 2.7 | 23 | 61 | Diglyme | 40.0% |
| 71 | 4.0 | 10.0% | P0.4R8 | 0.4 | 7.7 | 9 | 70 | 40.0% | dP2R4 | 2 | 4.1 | 45 | 186 | Diglyme | 40.0% |
| 72 | 4.0 | 10.0% | P2R4 | 2 | 4.3 | 45 | 195 | 40.0% | dP2R4 | 2 | 4.1 | 45 | 186 | Diglyme | 40.0% |
| 73 | 4.0 | 9.0% | P0.4R8 | 0.4 | 7.7 | 9 | 70 | 36.0% | dP1R2 | 1 | 2.1 | 23 | 48 | DMSO | 45.0% |
| 74 | 4.0 | 8.0% | P0.4R8 | 0.4 | 7.7 | 9 | 70 | 32.0% | dP1R2 | 1 | 2.1 | 23 | 48 | DMSO | 50.0% |
| 75 | 3.0 | 10.0% | P0.4R8 | 0.4 | 7.7 | 9 | 70 | 30.0% | dP1R2 | 1 | 2.1 | 23 | 48 | DMSO | 50.0% |
| 76 | 6.0 | 5.7% | P0.4R8 | 0.4 | 7.7 | 9 | 70 | 34.3% | dP1R2 | 1 | 2.1 | 23 | 48 | DMSO | 50.0% |
| 77 | 4.0 | 8.0% | P0.4R5 | 0.4 | 4.7 | 9 | 43 | 32.0% | dP1R2 | 1 | 2.1 | 23 | 48 | DMSO | 50.0% |
| 78 | 4.0 | 8.0% | P1R2 | 1 | 2.1 | 23 | 48 | 32.0% | dP1R2 | 1 | 2.1 | 23 | 48 | DMSO | 50.0% |
| 79 | 4.0 | 8.0% | P1R3 | 1 | 2.8 | 23 | 64 | 32.0% | dP1R2 | 1 | 2.1 | 23 | 48 | DMSO | 50.0% |
| 80 | 4.0 | 8.0% | P0.4R5 | 0.4 | 4.7 | 9 | 43 | 32.0% | dP1R3 | 1 | 2.7 | 23 | 61 | DMSO | 50.0% |
| 81 | 4.0 | 8.0% | P1R2 | 1 | 2.1 | 23 | 48 | 32.0% | dP1R3 | 1 | 2.7 | 23 | 61 | DMSO | 50.0% |
| 82 | 4.0 | 8.0% | P1R3 | 1 | 2.8 | 23 | 64 | 32.0% | dP1R3 | 1 | 2.7 | 23 | 61 | DMSO | 50.0% |
| 83 | 4.0 | 8.0% | P0.4R5 | 0.4 | 4.7 | 9 | 43 | 32.0% | dP0.4R5 | 0.35 | 4.9 | 8 | 39 | DMSO | 50.0% |
| 84 | 4.0 | 8.0% | P1R2 | 1 | 2.1 | 23 | 48 | 32.0% | dP0.4R5 | 0.35 | 4.9 | 8 | 39 | DMSO | 50.0% |
| 85 | 4.0 | 8.0% | P1R3 | 1 | 2.8 | 23 | 64 | 32.0% | dP0.4R5 | 0.35 | 4.9 | 8 | 39 | DMSO | 50.0% |
| 86 | 4.0 | 10.0% | P2R4 | 2 | 4.3 | 45 | 195 | 40.0% | dP2R4 | 2 | 4.1 | 45 | 186 | DEGMEE | 40.0% |
| 87 | 4.0 | 8.0% | P0.4R5 | 0.4 | 4.7 | 9 | 43 | 32.0% | dP1R2 | 1 | 2.1 | 23 | 48 | DEGMEE | 50.0% |
| 88 | 4.0 | 8.0% | P1R2 | 1 | 2.1 | 23 | 48 | 32.0% | dP1R2 | 1 | 2.1 | 23 | 48 | DEGMEE | 50.0% |
| 89 | 4.0 | 8.0% | P1R3 | 1 | 2.8 | 23 | 64 | 32.0% | dP1R2 | 1 | 2.1 | 23 | 48 | DEGMEE | 50.0% |
| 90 | 4.0 | 10.0% | P2R4 | 2 | 4.3 | 45 | 195 | 40.0% | dP2R4 | 2 | 4.1 | 45 | 186 | Diglyme | 40.0% |
| 91 | 4.0 | 8.0% | P0.4R5 | 0.4 | 4.7 | 9 | 43 | 32.0% | dP1R2 | 1 | 2.1 | 23 | 48 | Diglyme | 50.0% |
| 92 | 4.0 | 8.0% | P1R2 | 1 | 2.1 | 23 | 48 | 32.0% | dP1R2 | 1 | 2.1 | 23 | 48 | Diglyme | 50.0% |
| 93 | 4.0 | 8.0% | P1R3 | 1 | 2.8 | 23 | 64 | 32.0% | dP1R2 | 1 | 2.1 | 23 | 48 | Diglyme | 50.0% |
| 95 | 4.0 | 10.0% | P2R4 | 2 | 4.3 | 45 | 195 | 40.0% | dP2R4 | 2 | 4.1 | 45 | 186 | DMSO | 40.0% |

TABLE 3-continued

| | | Triblock copolymer (TB) | | | | | | Diblock copolymer (DB) | | | | | | Solvent | |
|---|---|---|---|---|---|---|---|---|---|---|---|---|---|---|---|
| Exp n° | Ratio DB/TB | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 96 | 4.0 | 8.0% | P0.4R5 | 0.4 | 4.7 | 9 | 43 | 32.0% | dP1R2 | 1 | 2.1 | 23 | 48 | DMSO | 50.0% |
| 97 | 4.0 | 8.0% | P1R2 | 1 | 2.1 | 23 | 48 | 32.0% | dP1R2 | 1 | 2.1 | 23 | 48 | DMSO | 50.0% |
| 98 | 4.0 | 8.0% | P1R3 | 1 | 2.8 | 23 | 64 | 32.0% | dP1R2 | 1 | 2.1 | 23 | 48 | DMSO | 50.0% |

Figure 30:
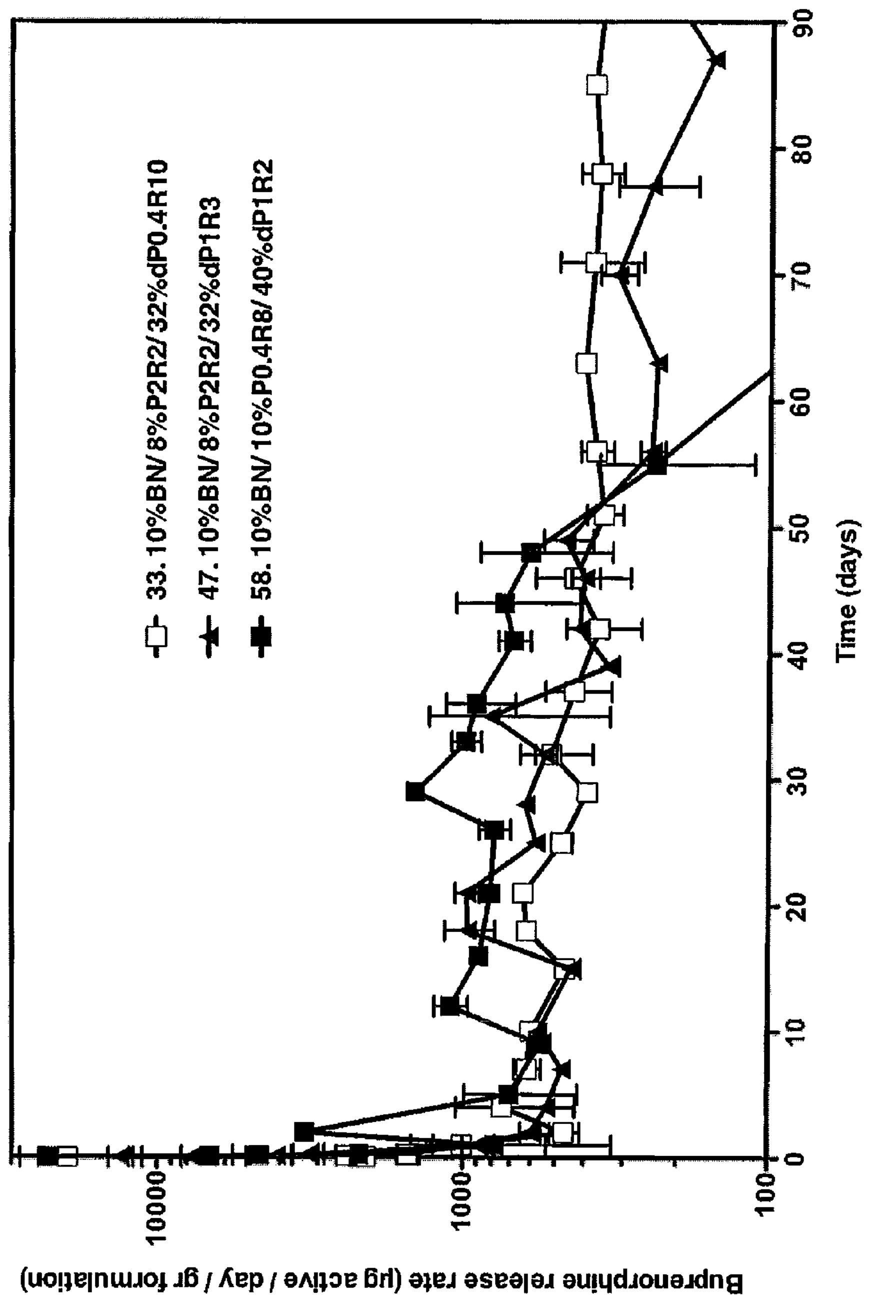
FIG. 30 is a graph showing the in vitro release rate of buprenorphine over time (days) from formulations n°33 (10% BN/8% P2R2/32% dP0.4R10), n°47 (10% BN/8% P2R2/32% dP1R3) and n°58 (10% BN/10% P0.4R8/40% dP1R2).
Figure 31:
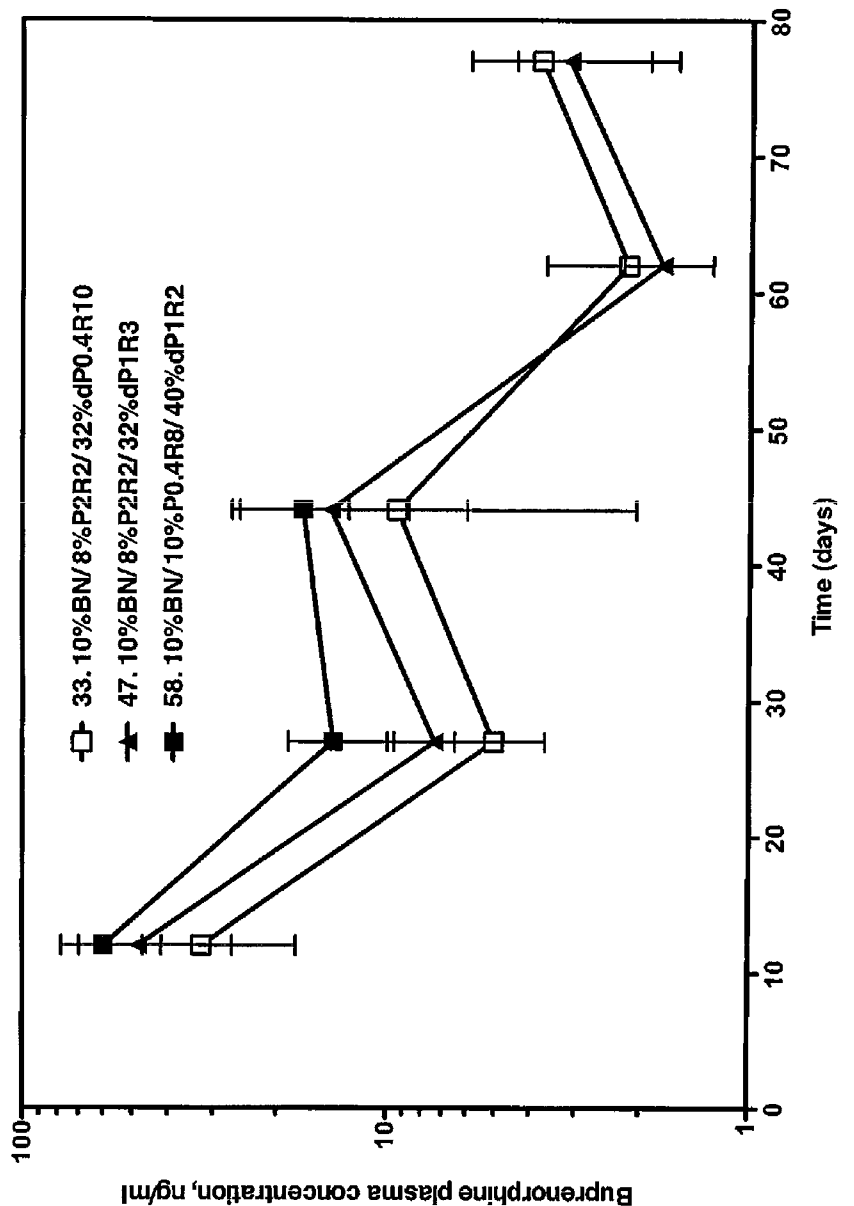
FIG. 31 is a graph showing the plasma concentration of buprenorphine over time (days) in rats injected with formulations n°33 (10% BN/8% P2R2/32% dP0.4R10), n°47 (10% BN/8% P2R2/32% dP1R3) and n°58 (10% BN/10% P0.4R8/40% dP1R2).

The results of these formulations are illustrated in FIGS. 30 and 31.

Example 6

Risperidone's Formulations Preparation

The formulations described herein were based on organic solution of polymers prepared as in Example 1, containing as the drug, risperidone. Typically, 0.4 grams of polymers, corresponding to a mix of a diblock copolymer and a triblock copolymer in defined mass ratio, were dissolved in 0.5 grams of dimethyl sulfoxide at room temperature overnight under constant magnetic stirring. The next day, 100 mg of risperidone was added to the polymer solution and stirred. The formulations were loaded in a syringe before use.

Three different formulations were selected for in vivo experiments. The composition of these formulations is shown in Table 4 below. The formulations were injected subcutaneously in the interscapular space of male rats (300 gr) at a final dose of 21 mg/kg of risperidone. Blood samples were withdraw periodically and analyzed for risperidone and 9-OH risperidone concentrations by LC/MS/MS.

The formulations are shown in Table 4 below.

Figure 32:
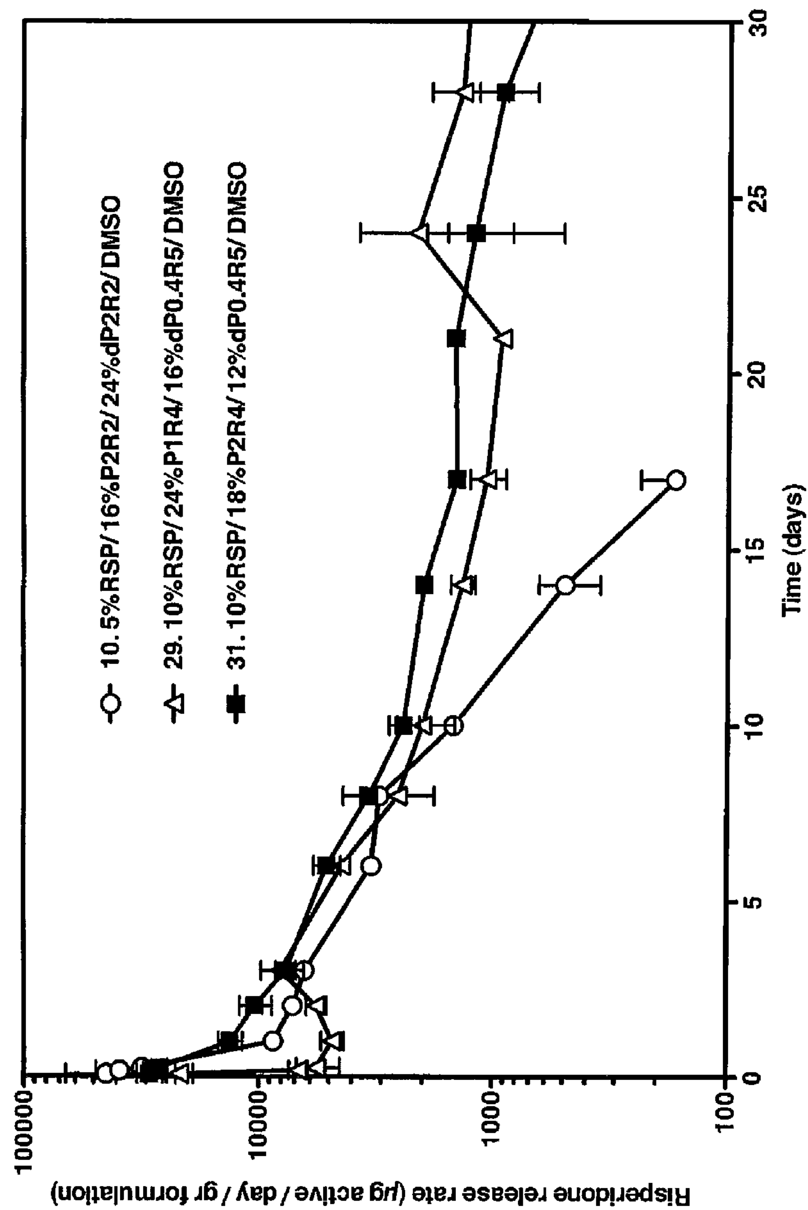
FIG. 32 is a graph showing the in vitro release rate of risperidone over time (days) from formulations based on triblock polymer P2R5 (45 units of ethylene oxide and 216 units of lactic acid) mixed with diblock polymer dP0.2R13 (3 units of ethylene oxide and 39 units of lactic acid) at different ratios (see Table 2 for details).
Figure 33:
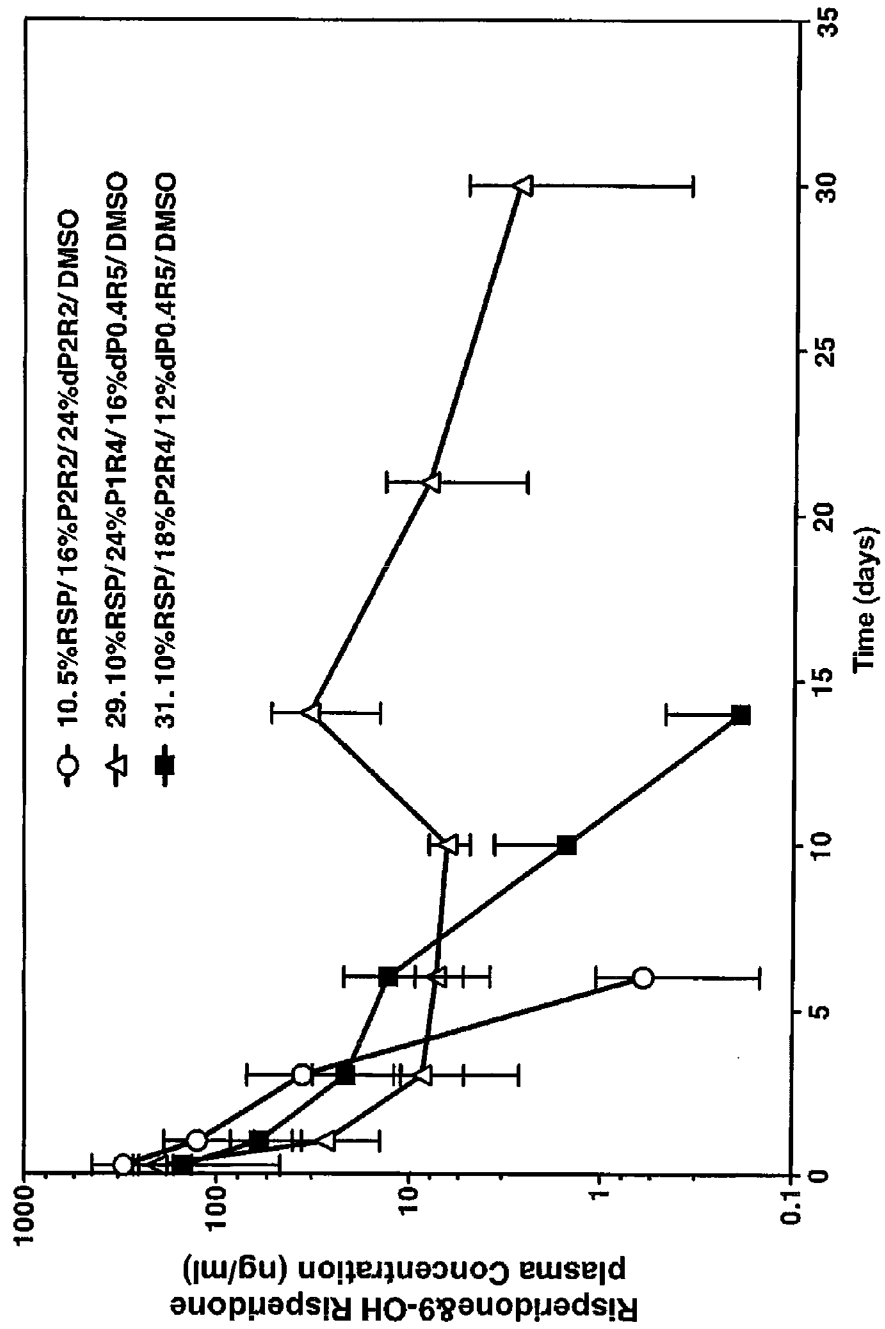
FIG. 33 is a graph showing the plasma concentration of risperidone and 9-OH risperidone over time (days) in rats injected with formulations n°10 (5% RSP/16% P2R2/24% dP2R2/DMSO), n°29 (10% RSP/24% P1R4/16% dP0.4R5/DMSO) and n°31 (10% RSP/18% P2R4/12% dP0.4R5/DMSO).

The results of these formulations are illustrated in FIGS. 32 and 33.

Example 7

Ivermectin's Formulations Preparation

The formulations described herein were based on organic solution of polymers prepared as in Example 1, containing as the drug, ivermectin. Typically, 0.4 grams of polymers, corresponding to a mix of a diblock copolymer and a triblock copolymer in defined mass ratio, were dissolved in 0.55 grams of dimethyl sulfoxide at room temperature overnight under constant magnetic stirring. The next day, 50 mg of ivermectin was added to the polymer solution and stirred until complete dissolution. Three different formulations were selected for in vivo experiments. The composition of these formulations is shown in Table 5 below. The formulations were injected subcutaneously in the interscapular space of male dogs (10 to 17 kg) at a final dose of 0.6 mg/kg of ivermectin. Blood samples were withdraw periodically and analyzed for ivermectin concentrations by LC/MS/MS.

The formulations are shown in Table 5.

TABLE 4

| | | Risp | Triblock copolymer (TB) | | | | | | Diblock copolymer (DB) | | | | | | Solvent | |
|---|---|---|---|---|---|---|---|---|---|---|---|---|---|---|---|---|
| Exp n° | Ratio DB/TB | % (w/w) | % (w/w) | Code | PEG (kDa) | Ratio (LA/EO) | DP-PEG | DP-PLA | % (w/w) | Code | PEG (kDa) | Ratio (LA/EO) | DP-PEG | DP-PLA | Name | % (w/w) |
| 5 | 1.5 | 2.5% | 16.0% | P2R3 | 2 | 3.5 | 45 | 158.6 | 24.0% | dP2R3 | 2 | 2.7 | 45 | 122.7 | DMSO | 57.5% |
| 6 | 1.5 | 2.5% | 16.0% | P2R2 | 2 | 2.3 | 45 | 104.5 | 24.0% | dP1R3 | 1 | 2.7 | 23 | 61.4 | DMSO | 57.5% |
| 10 | 1.5 | 5.0% | 16.0% | P2R2 | 2 | 2.3 | 45 | 104.5 | 24.0% | dP2R3 | 2 | 2.7 | 45 | 122.7 | DMSO | 55.0% |
| 11 | 1.5 | 5.0% | 16.0% | P2R3 | 2 | 3.5 | 45 | 158.6 | 24.0% | dP2R3 | 2 | 2.7 | 45 | 122.7 | DMSO | 55.0% |
| 12 | 1.5 | 5.0% | 16.0% | P2R2 | 2 | 2.3 | 45 | 104.5 | 24.0% | dP1R3 | 1 | 2.7 | 23 | 61.4 | DMSO | 55.0% |
| 16 | 0.7 | 5.0% | 24.0% | P2R3 | 2 | 3.5 | 45 | 158.6 | 16.0% | dP0.4R5 | 0.35 | 4.9 | 8 | 39.0 | DMSO | 55.0% |
| 17 | 1.5 | 5.0% | 16.0% | P3R2 | 3 | 2.3 | 68 | 156.8 | 24.0% | dP2R3 | 2 | 2.9 | 45 | 131.8 | DMSO | 55.0% |
| 19 | 1.5 | 5.0% | 16.0% | P3R3 | 3 | 3.2 | 68 | 218.2 | 24.0% | dP2R3 | 2 | 2.7 | 45 | 122.7 | DMSO | 55.0% |
| 20 | 1.5 | 5.0% | 16.0% | P1R4 | 1 | 3.8 | 23 | 86.4 | 24.0% | dP2R3 | 2 | 2.9 | 45 | 131.8 | DMSO | 55.0% |
| 21 | 0.7 | 5.0% | 24.0% | P1R4 | 1 | 3.8 | 23 | 86.4 | 16.0% | dP0.4R5 | 0.35 | 4.9 | 8 | 39.0 | DMSO | 55.0% |
| 22 | 1.5 | 10.0% | 16.0% | P2R2 | 2 | 2.3 | 45 | 104.5 | 24.0% | dP2R3 | 2 | 2.7 | 45 | 122.7 | DMSO | 50.0% |
| 23 | 1.5 | 10.0% | 16.0% | P2R3 | 2 | 3.5 | 45 | 158.6 | 24.0% | dP2R3 | 2 | 2.7 | 45 | 122.7 | DMSO | 50.0% |
| 25 | 0.7 | 10.0% | 24.0% | P2R3 | 2 | 3.5 | 45 | 158.6 | 16.0% | dP0.4R5 | 0.35 | 4.9 | 8 | 39.0 | DMSO | 50.0% |
| 26 | 1.5 | 10.0% | 16.0% | P3R3 | 3 | 3.2 | 68 | 218.2 | 24.0% | dP2R3 | 2 | 2.7 | 45 | 122.7 | DMSO | 50.0% |
| 27 | 1.5 | 10.0% | 16.0% | P1R4 | 1 | 3.8 | 23 | 86.4 | 24.0% | dP2R3 | 2 | 2.9 | 45 | 131.8 | DMSO | 50.0% |
| 28 | 0.7 | 5.0% | 18.0% | P1R4 | 1 | 3.8 | 23 | 86.4 | 12.0% | dP0.4R5 | 0.35 | 4.9 | 8 | 39.0 | DMSO | 65.0% |
| 29 | 0.7 | 10.0% | 24.0% | P1R4 | 1 | 3.8 | 23 | 86.4 | 16.0% | dP0.4R5 | 0.35 | 4.9 | 8 | 39.0 | DMSO | 60.0% |
| 30 | 0.7 | 10.0% | 18.0% | P1R4 | 1 | 3.8 | 23 | 86.4 | 12.0% | dP0.4R5 | 0.35 | 4.9 | 8 | 39.0 | DMSO | 60.0% |
| 31 | 0.7 | 10.0% | 18.0% | P2R3 | 2 | 3.5 | 45 | 158.6 | 12.0% | dP0.4R5 | 0.35 | 4.9 | 8 | 39.0 | DMSO | 60.0% |
| 32 | 1.5 | 10.0% | 12.0% | P1R4 | 1 | 3.8 | 23 | 86.4 | 18.0% | dP2R3 | 2 | 2.9 | 45 | 131.8 | DMSO | 60.0% |
| 33 | 1.5 | 10.0% | 12.0% | P3R3 | 3 | 3.2 | 68 | 218.2 | 18.0% | dP2R3 | 2 | 2.7 | 45 | 122.7 | DMSO | 60.0% |
| 34 | 0.7 | 15.0% | 18.0% | P1R4 | 1 | 3.8 | 23 | 86.4 | 12.0% | dP0.4R5 | 0.35 | 4.9 | 8 | 39.0 | DMSO | 55.0% |
| 35 | 1.5 | 15.0% | 12.0% | P2R2 | 2 | 2.3 | 45 | 104.5 | 18.0% | dP2R3 | 2 | 2.7 | 45 | 122.7 | DMSO | 55.0% |
| 36 | 0.7 | 15.0% | 18.0% | P2R3 | 2 | 3.5 | 45 | 158.6 | 12.0% | dP0.4R5 | 0.35 | 4.9 | 8 | 39.0 | DMSO | 55.0% |
| 40 | 0.7 | 10.0% | 24.0% | P1R4 | 1 | 3.8 | 23 | 86.4 | 16.0% | dP0.4R5 | 0.35 | 5.02 | 8 | 39.9 | DMSO | 60.0% |
| 41 | 0.7 | 10.0% | 18.0% | P2R3 | 2 | 3.5 | 45 | 158.6 | 12.0% | dP0.4R5 | 0.35 | 5.02 | 8 | 39.9 | DMSO | 60.0% |
| 42 | 0.7 | 10.0% | 24.0% | P1R4 | 1 | 4.0 | 23 | 89.8 | 16.0% | dP0.4R5 | 0.35 | 5.02 | 8 | 39.9 | DMSO | 60.0% |
| 43 | 0.7 | 10.0% | 24.0% | P1R4 | 1 | 3.8 | 23 | 86.4 | 16.0% | dP0.4R5 | 0.35 | 5.02 | 8 | 39.9 | DMSO | 60.0% |
| 44 | 0.7 | 10.0% | 24.0% | P1R4 | 1 | 4.0 | 23 | 89.8 | 16.0% | dP0.4R5 | 0.35 | 5.02 | 8 | 39.9 | DMSO | 60.0% |

TABLE 5

| Exp n° | Ratio DB/TB | IVM % (w/w) | Triblock copolymer (TB) % (w/w) | Code | PEG (kDa) | Ratio (LA/EO) | DP-PEG | DP-PLA | Diblock copolymer (DB) % (w/w) | Code | PEG (kDa) | Ratio (LA/EO) | DP-PEG | DP-PLA | Solvent Name | % (w/w) |
|---|---|---|---|---|---|---|---|---|---|---|---|---|---|---|---|---|
| 9 | 1.7 | 5.0% | 15.0% | P3R3 | 3 | 3.2 | 68 | 218 | 25.0% | dP0.4R5 | 0.35 | 4.9 | 8 | 39 | DMSO | 55.0% |
| 10 | 1.7 | 5.0% | 15.0% | P2R3 | 2 | 3.5 | 45 | 159 | 25.0% | dP2R3 | 2 | 2.9 | 45 | 132 | DMSO | 55.0% |
| 11 | 1.7 | 5.0% | 15.0% | P2R5 | 2 | 5.3 | 45 | 241 | 25.0% | dP2R2 | 2 | 2.3 | 45 | 105 | DMSO | 55.0% |

Figure 34:
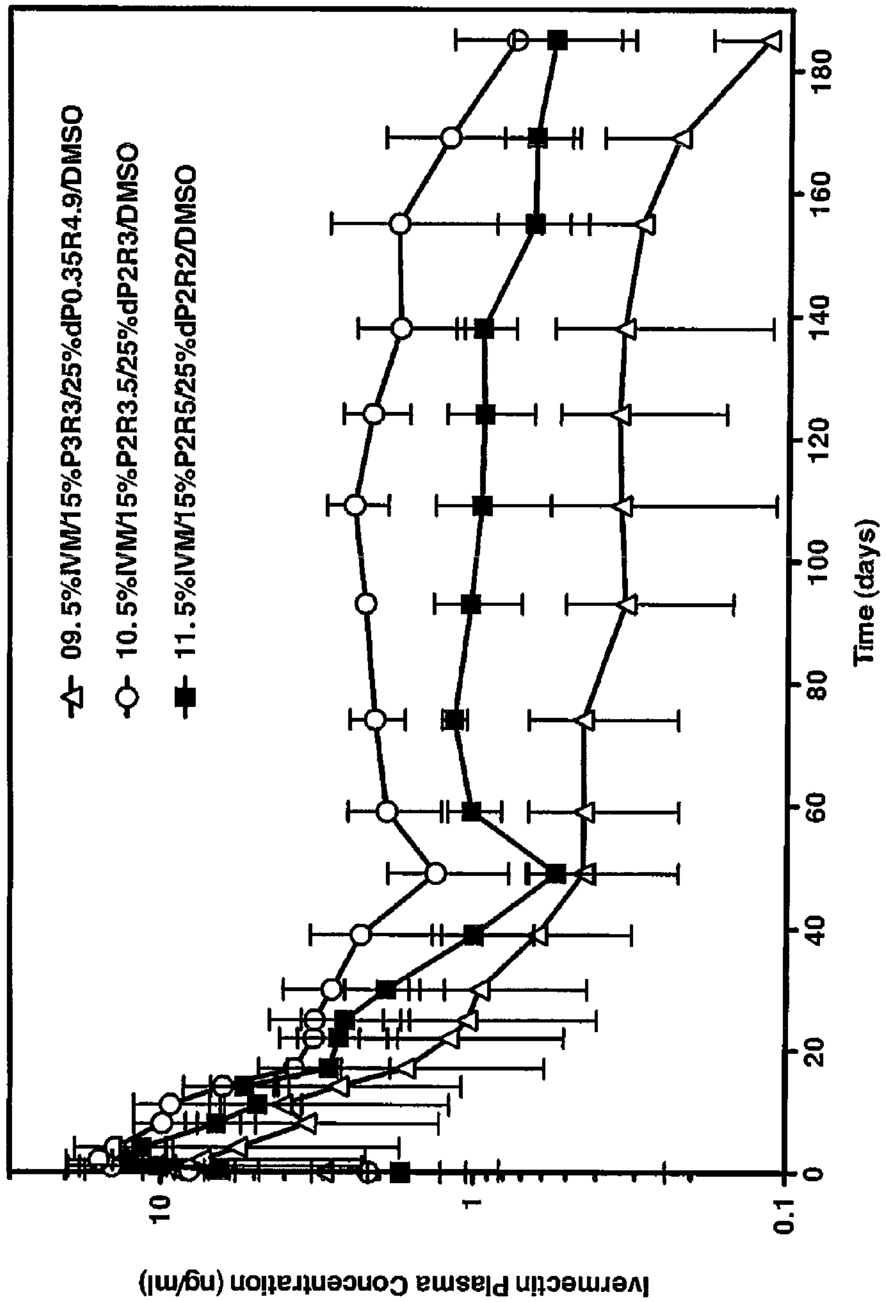
FIG. 34 is a graph showing the plasma concentration of ivermectin over time (days) in dogs injected with formulations n°7 (5% IVM/15% P3R3/25% dP0.4R5/DMSO), n°9 (5% IVM/15% P2R4/25% dP2R3/DMSO) and n°10 (5% IVM/15% P2R5/25% dP2R2/DMSO).

The results are illustrated in FIG. 34.

Example 8

Injectability of Differing Compositions

Various formulations were tested for injectability using formulations with different ratios of triblock (TB) and diblock (DB). Different solutions in DMSO based on a mixture of the triblock copolymer P6R1(TB) and the diblock copolymer dP2R4(DB) were prepared.

A 50% weight %/weight % polymer/formulation mass was used in these viscosity experiments. The weight %/weight % of triblock to diblock that was used in this experiment were the following: 50 wt. %:0 wt. %, 45 wt. %:5 wt. %, 20 wt. %:5 wt. %, 35 wt. %:15 wt. %, 15 wt. %:10 wt. %, 25 wt. %:25 wt. %, 10 wt. %:15 wt. %, 15 wt. %:35 wt. %, 5 wt. %:20 wt. %, 5 wt. %:45 wt. % and 0 wt. %:50 wt. %.

Figure 3:
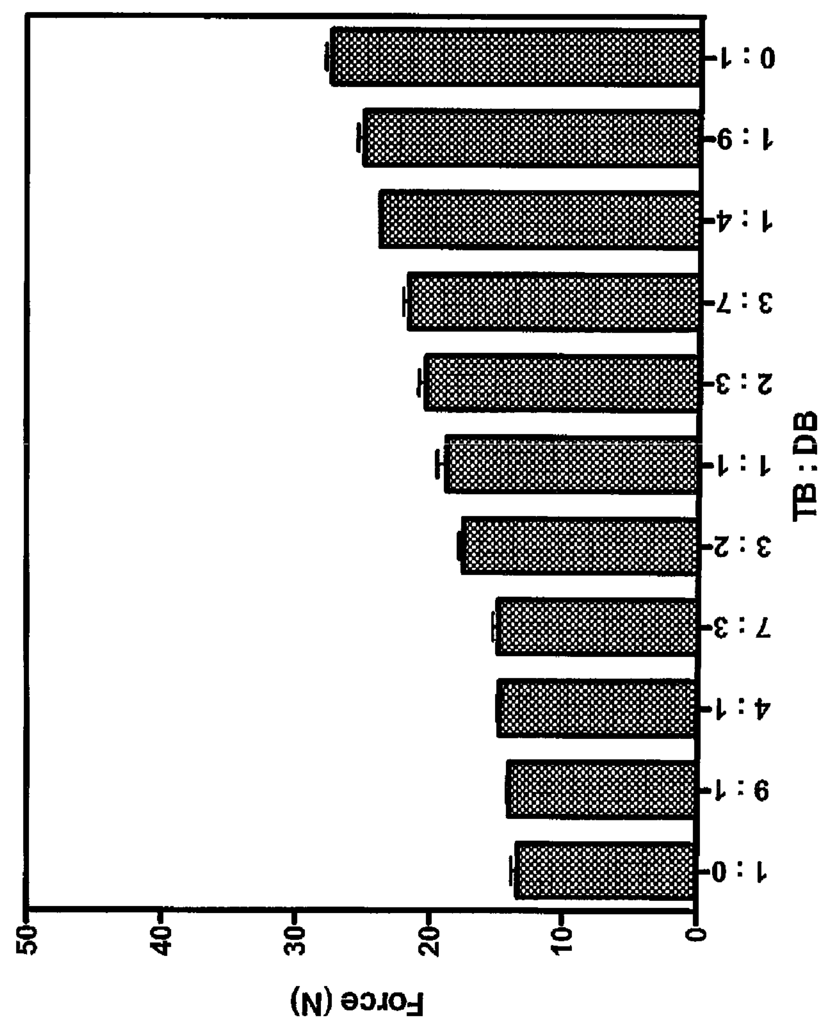
FIG. 3 is a graph showing the injectability of formulations based on 40% P6R1 (TB); dP2R4(DB) in various ratios ranging from 1:0 triblock copolymer to diblock copolymer to 0:1 triblock copolymer to diblock copolymer. This graph illustrates that all formulations are injectable using a classical injection device.

The injectability results are shown in FIG. 3.

Example 9

In Vitro Release Assay 100 to 500 mg of formulation was added to 20 to 50 ml of physiological buffer. The physiological buffer that was used was KRT containing 50 ml Krebs/Ringer/Tris (KRT) buffer pH 7.4, which is 143 mM Sodium Chloride, 5.1 mM Potassium Chloride, 2.7 mM Calcium Chloride, 1.34 mM Magnesium Sulfate, 25 mM Tris-CL pH 7.4 and 0.1% sodium azide. Upon injection, the solvent diffused away from the formulation and the remaining polymer formed a solid biodegradable implant within the aqueous environment.

In order to maintain sink conditions, for drug release, the release medium was maintained under constant shaking at 180 rpm (Unimax 1010 apparatus, Heidolph) at 37° C. At pre-determined time intervals, media are collected and analyzed by HPLC. The amount of the GLP-1 analogue peptide M53, released from the formulation was calculated from a calibration curve. The concentration of M53 ranged between 0 and 5 mg/ml or it ranged between 0 and 200 μg/ml.

Figure 4:
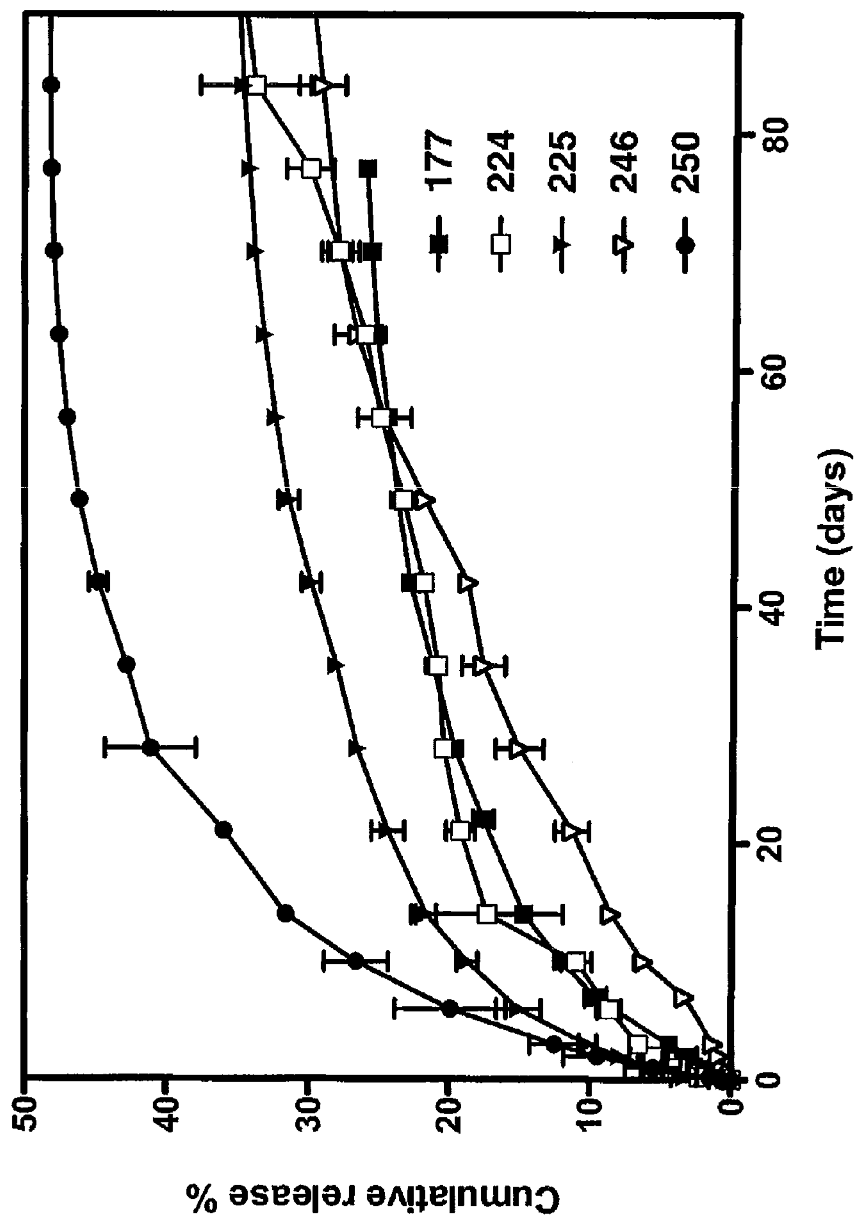
FIG. 4 is a graph showing the in vitro cumulative percentage release curve from candidate formulations over time (days) of various compositions of the invention. The compositions described as numbers 177, 246, 224, 225 and 250 are described in Table1.
Figure 5:
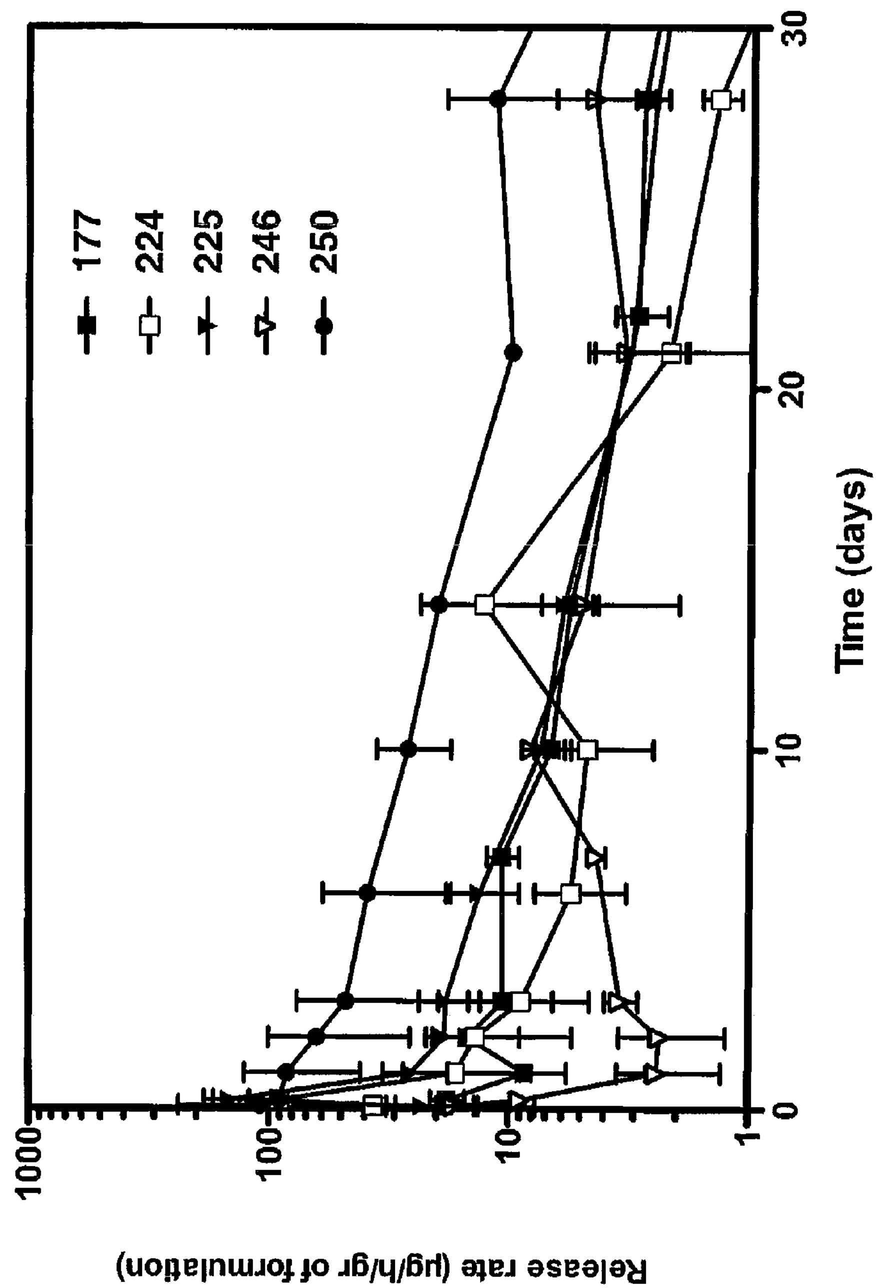
FIG. 5 is a graph showing the in vitro release rate from candidate formulations in micrograms per hour per gram of formulation (μg/h/gr of formulation) The compositions described as numbers 177, 246, 224, 225 and 250 are described in Table1.

The results are shown in FIG. 4 and FIG. 5. FIG. 5 illustrates the release rate of formulations 177, 224, 225, 246 and 250 as shown in Table 1, while FIG. 4 shows the cumulative release of drug from the indicated formulations.

When the GPL-1 analogue was incorporated into the polymer solution, it was encapsulated within the polymer matrix as it solidified. The drug was then released either by diffusion inside the matrix or by biodegradation of the matrix.

Example 10

Pharmacokinetic Study

Several formulations were tested in a pharmacokinetic study in rats. Compositions containing 1 mg of drug per animal of the formulations of 177, 224, 225, 246 and 250, as set forth in Table 1 were subcutaneously administered to rats. Blood samples were collected into EDTA tubes at different time points, centrifuged and the plasma from each time point was retained. The plasma samples were analyzed by LC/MS/MS and quantified for drug content. Results are presented as ng/ml of plasma measured over time.

Figure 6:
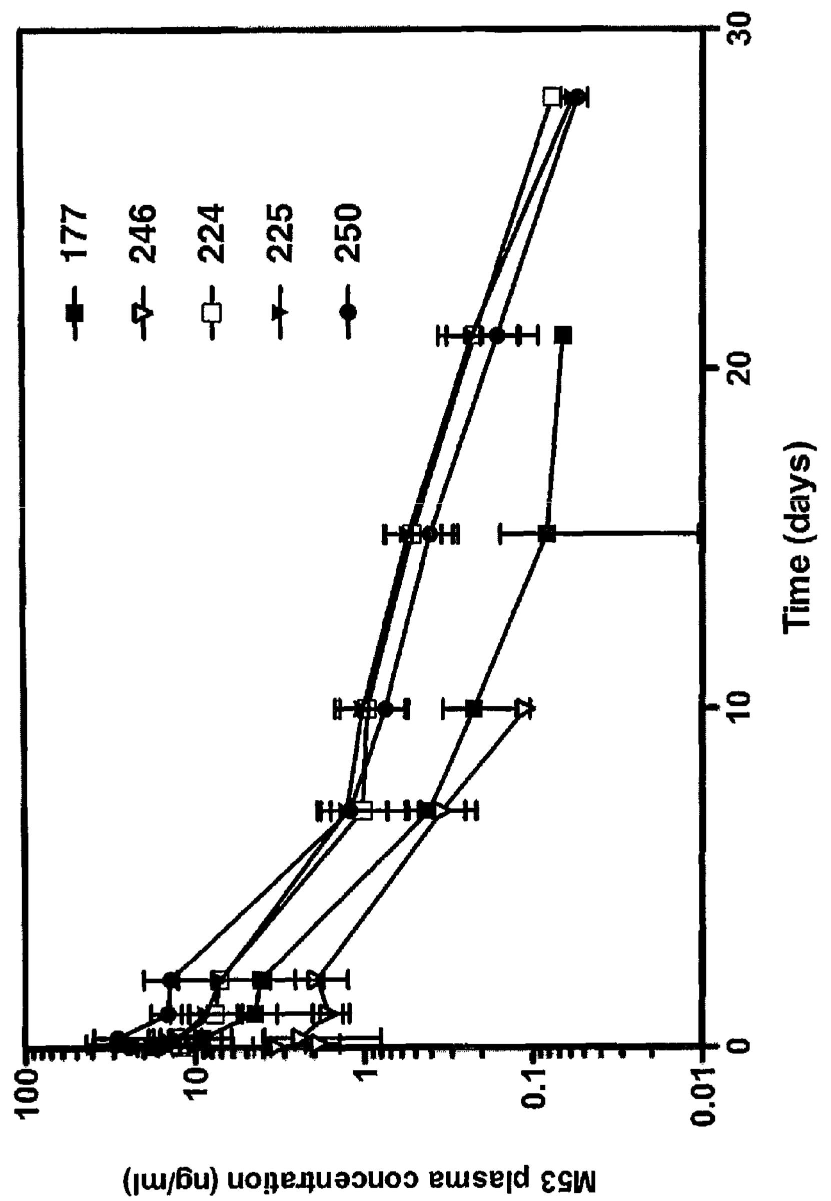
FIG. 6 is a graph showing the M53 plasma concentration in nanograms per milliliter (ng/ml) over time in days. Day zero is the day that the composition was administered subcutaneously. The compositions indicated as numbers 177, 246, 224, 225 and 250 are described in Table1.
Figure 7:
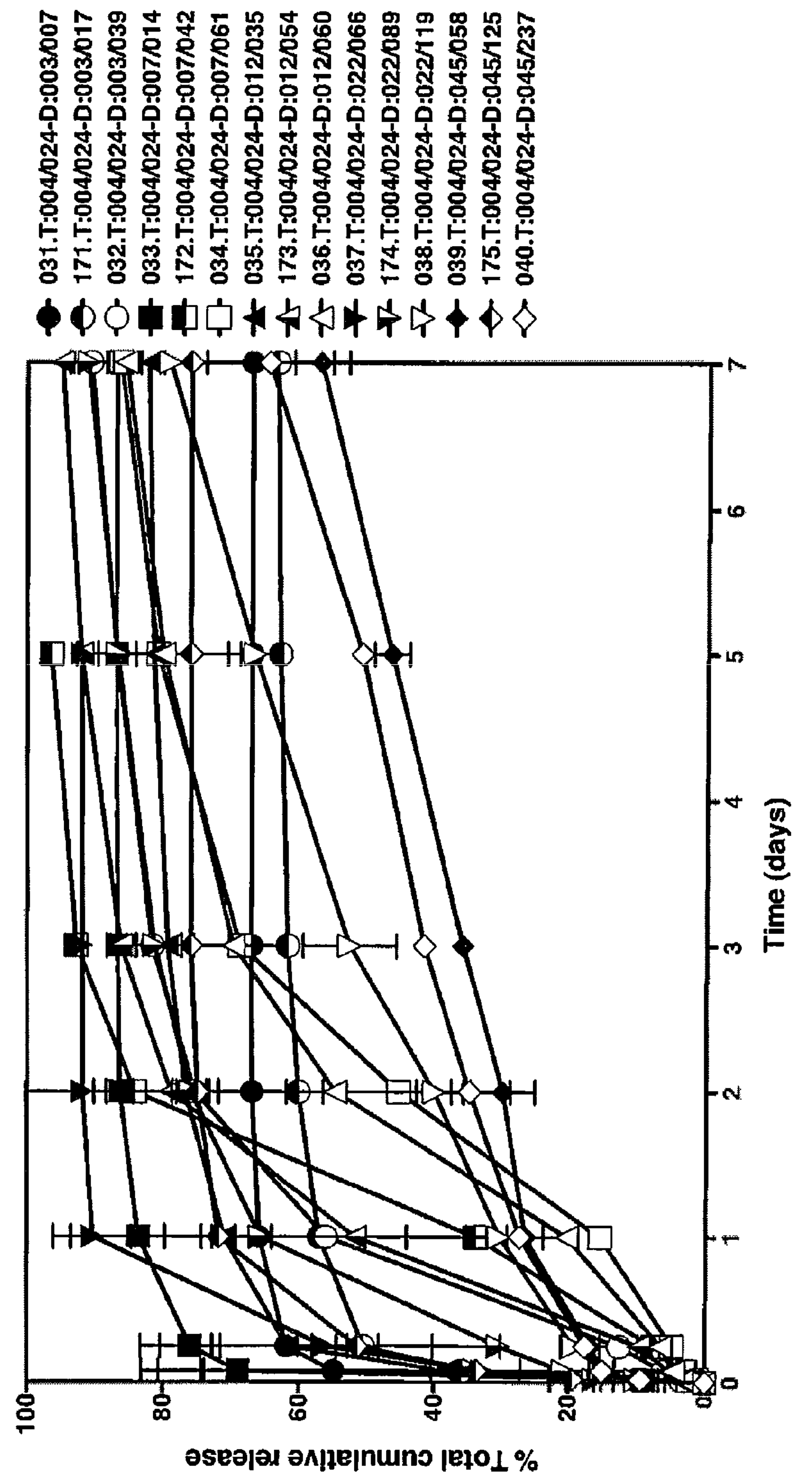
FIG. 7 is a graph showing the in vitro cumulative percent release of acetaminophen over time (days) from formulations based on triblock copolymer P0.2R5 (4 units of ethylene oxide and 24 units of lactic acid) mixed with various diblock copolymers (see Table 2 for details).
Figure 8:
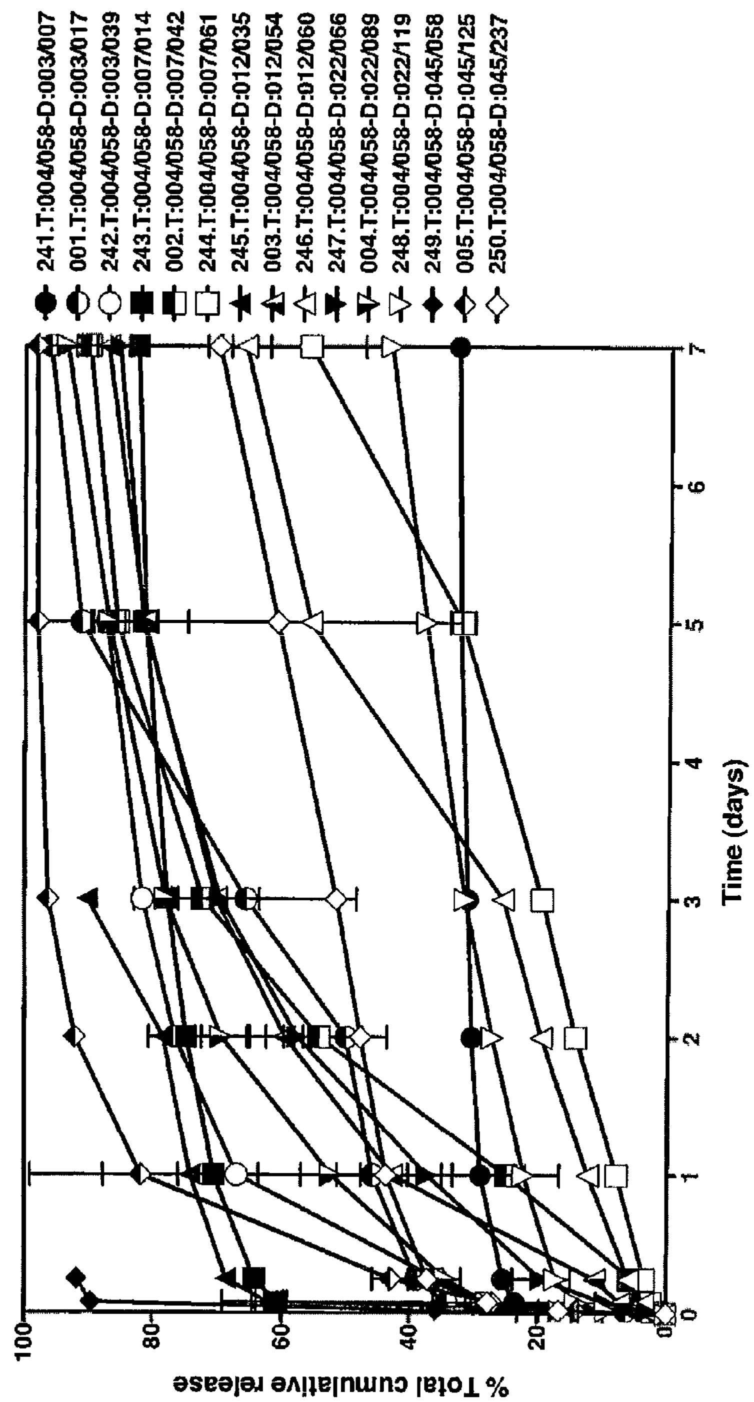
FIG. 8 is a graph showing the in vitro cumulative percent release of acetaminophen over time (days) from formulations based on triblock copolymer P0.2R14 (4 units of ethylene oxide and 58 units of lactic acid) mixed with various diblock copolymers (see Table 2 for details).
Figure 9:
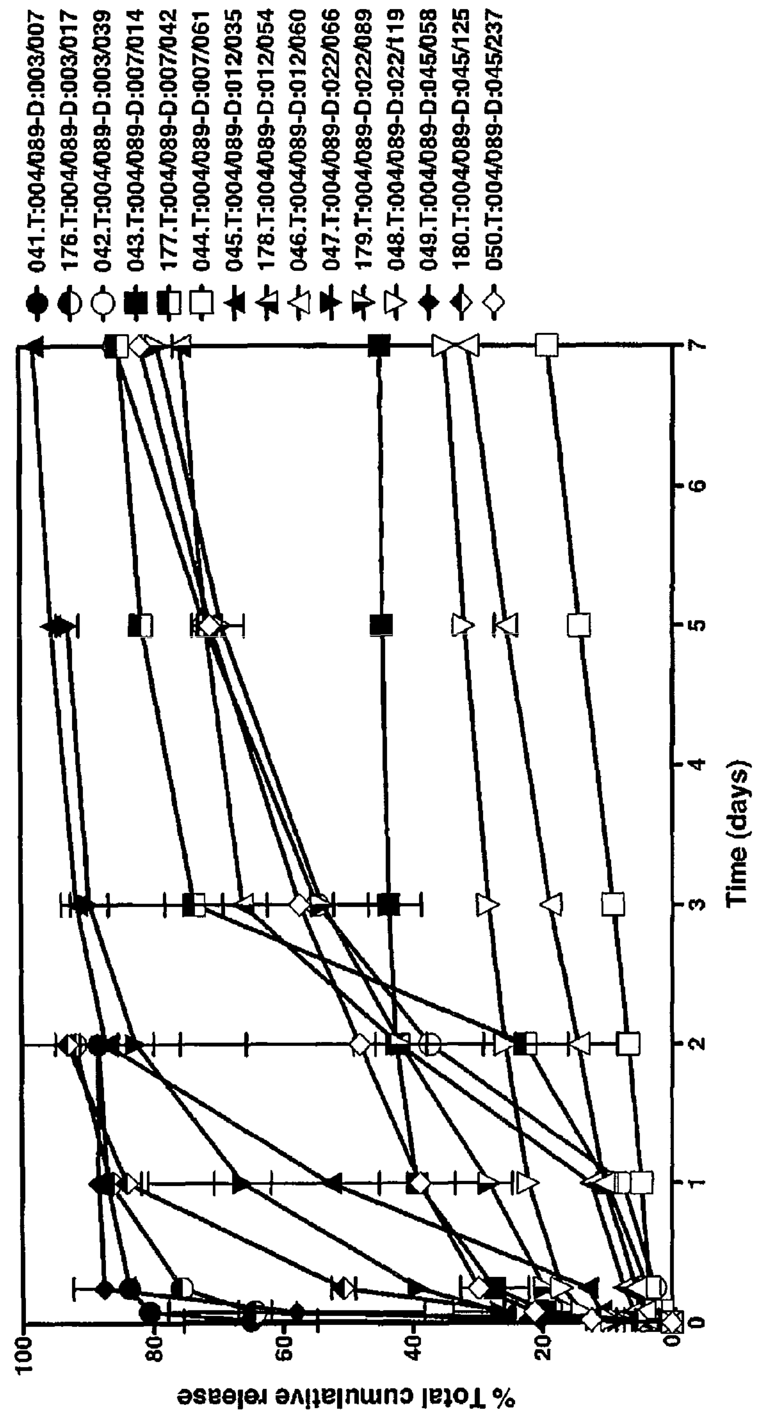
FIG. 9 is a graph showing the in vitro cumulative percent release of acetaminophen over time (days) from formulations based on triblock copolymer P0.2R22 (4 units of ethylene oxide and 89 units of lactic acid) mixed with various diblock copolymers (see Table 2 for details).
Figure 10:
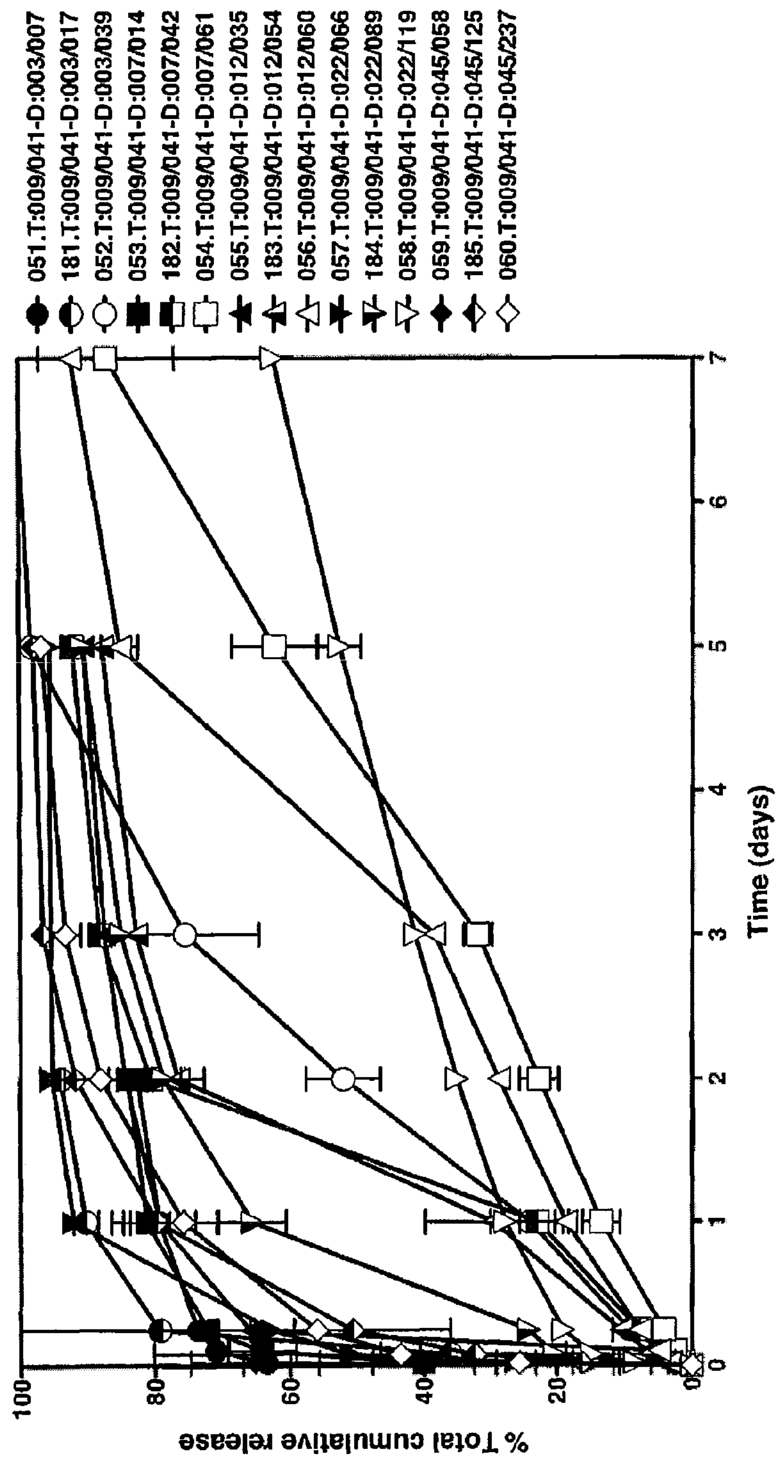
FIG. 10 is a graph showing the in vitro cumulative percent release of acetaminophen over time (days) from formulations based on triblock copolymer P0.4R4 (9 units of ethylene oxide and 41 units of lactic acid) mixed with various diblock copolymers (see Table 2 for details).
Figure 11:
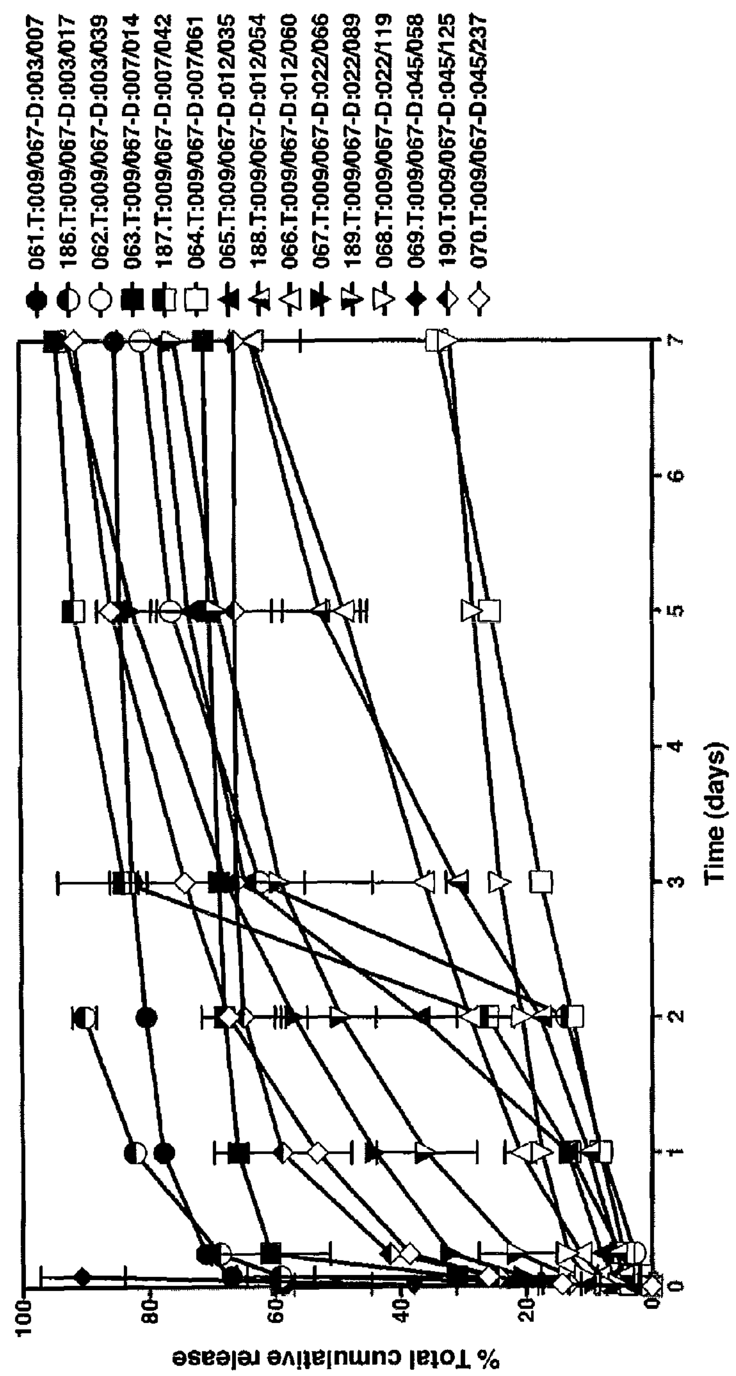
FIG. 11 is a graph showing the in vitro cumulative percent release of acetaminophen over time (days) from formulations based on triblock copolymer P0.4R7 (9 units of ethylene oxide and 67 units of lactic acid) mixed with various diblock copolymers (see Table 2 for details).
Figure 12:
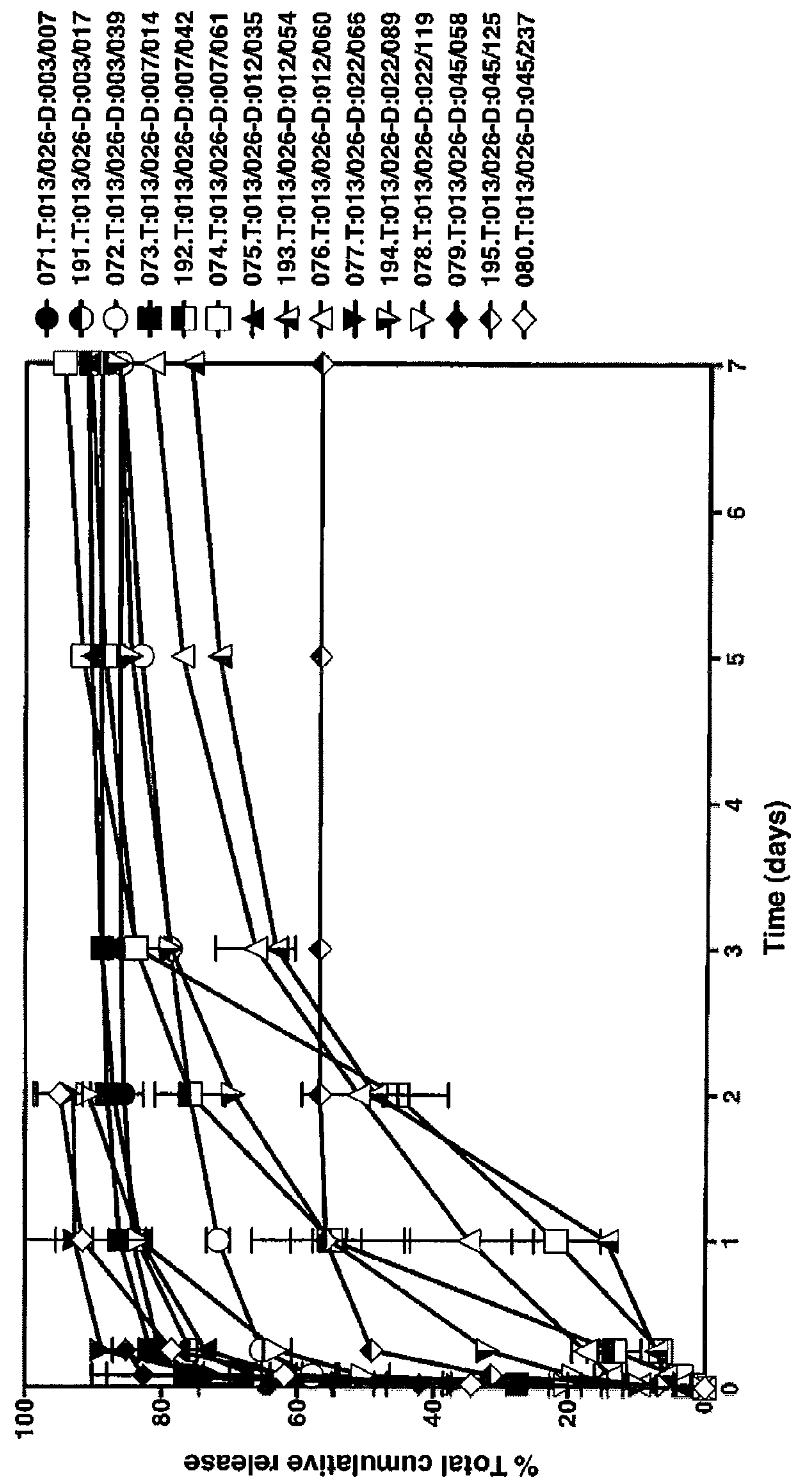
FIG. 12 is a graph showing the in vitro cumulative percent release of acetaminophen over time (days) from formulations based on triblock copolymer P0.6R1 (13 units of ethylene oxide and 26 units of lactic acid) mixed with various diblock copolymers (see Table 2 for details).
Figure 13:
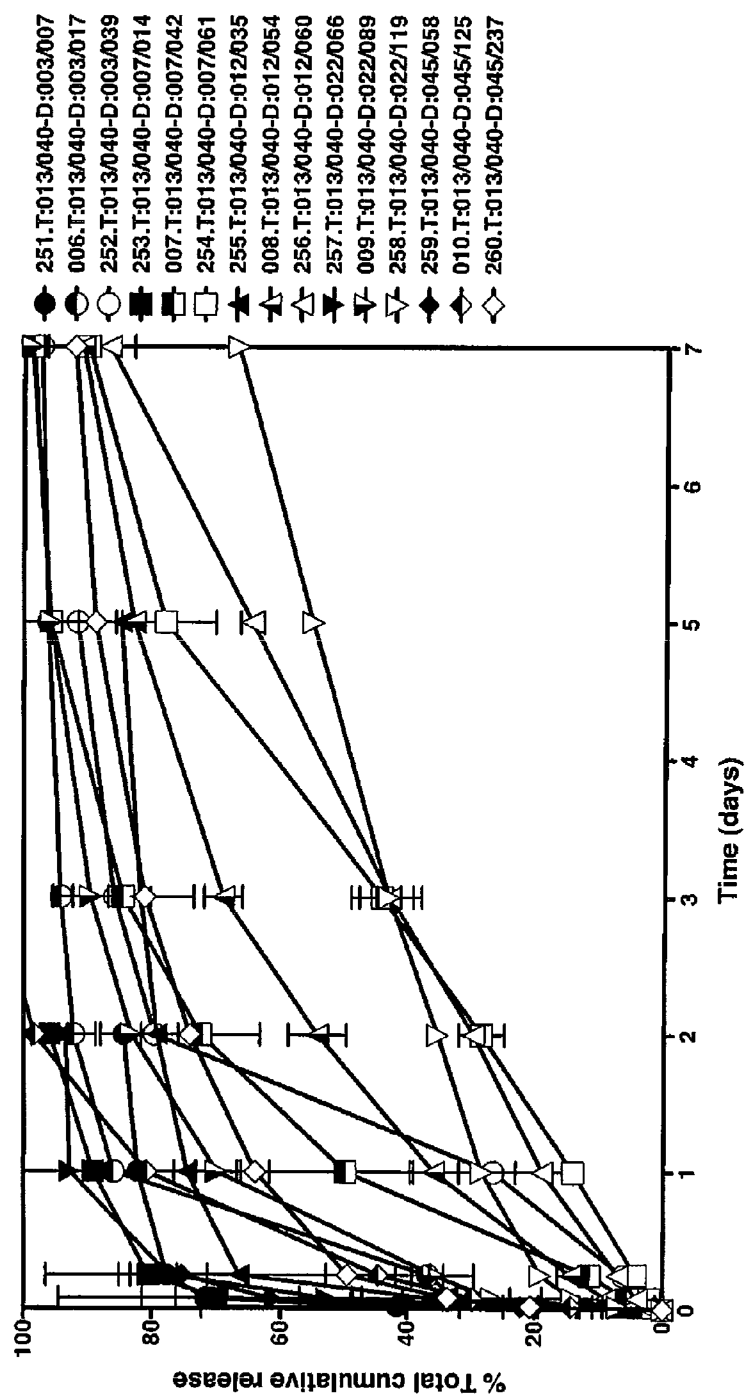
FIG. 13 is a graph showing the in vitro cumulative percent release of acetaminophen over time (days) from formulations based on triblock copolymer P0.6R3 (13 units of ethylene oxide and 40 units of lactic acid) mixed with various diblock copolymers (see Table 2 for details).
Figure 14:
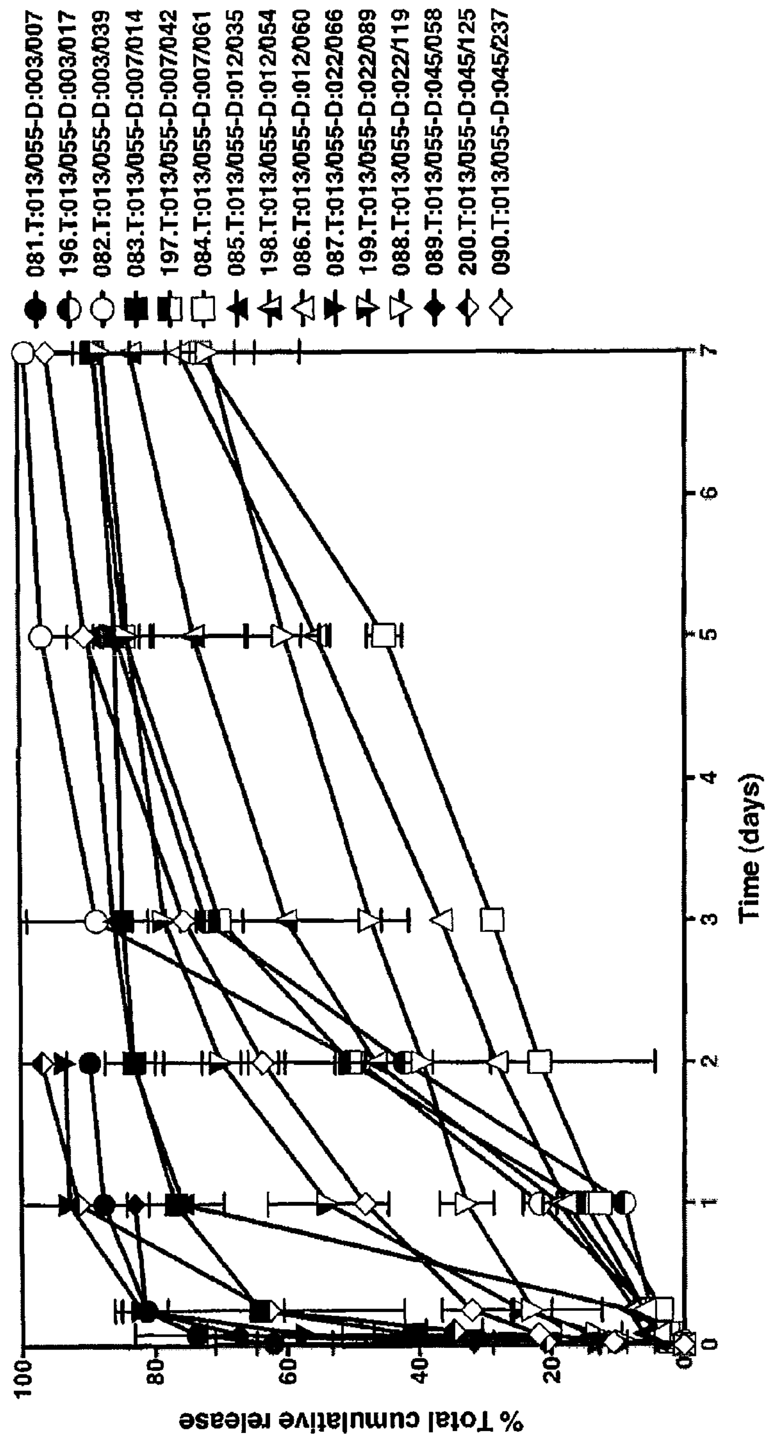
FIG. 14 is a graph showing the in vitro cumulative percent release of acetaminophen over time (days) from formulations based on triblock copolymer P0.6R4 (13 units of ethylene oxide and 55 units of lactic acid) mixed with various diblock copolymers (see Table 2 for details).
Figure 15:
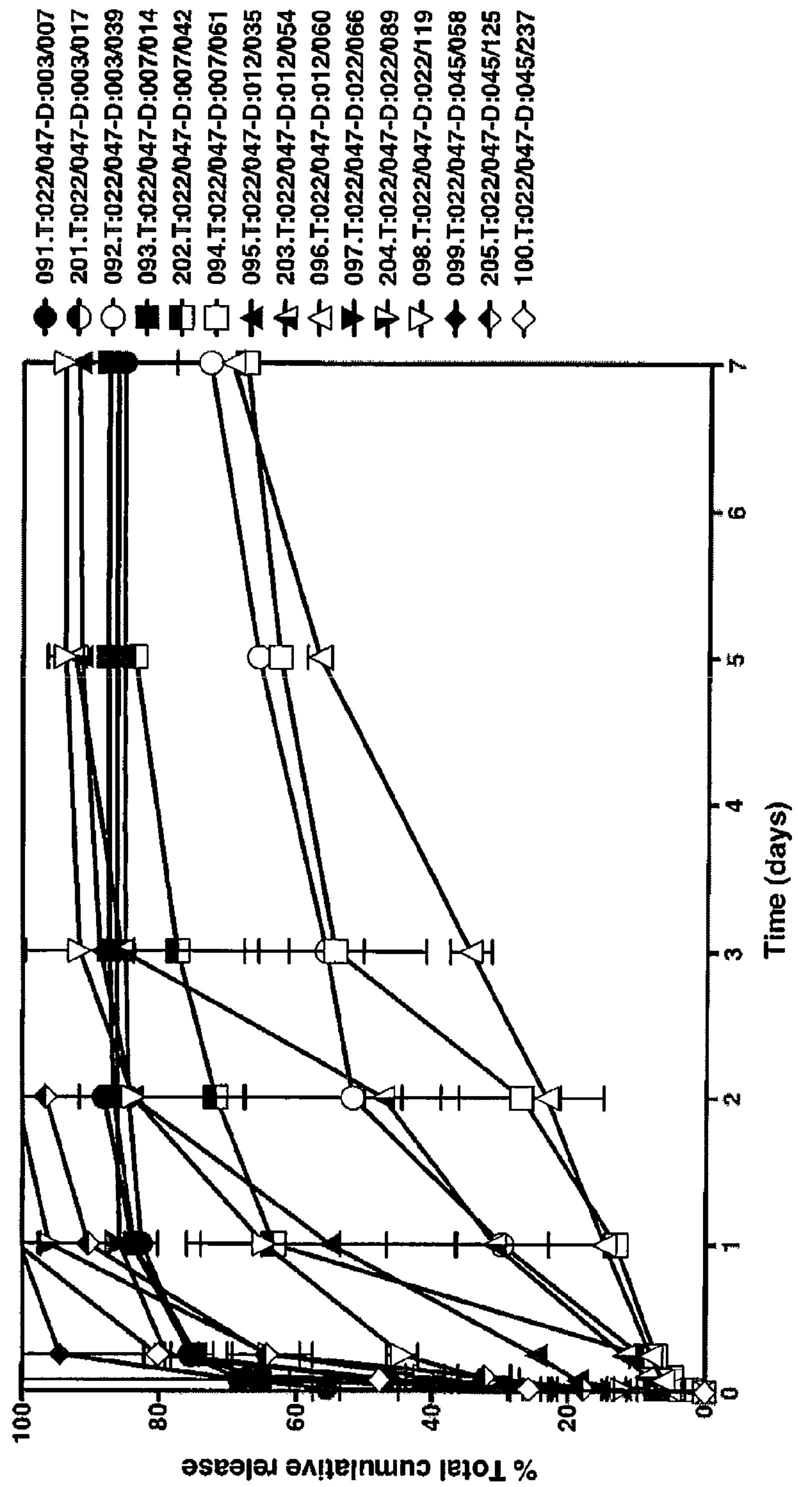
FIG. 15 is a graph showing the in vitro cumulative percent release of acetaminophen over time (days) from formulations based on triblock copolymer P1R2 (22 units of ethylene oxide and 47 units of lactic acid) mixed with various diblock copolymers (see Table 2 for details).
Figure 16:
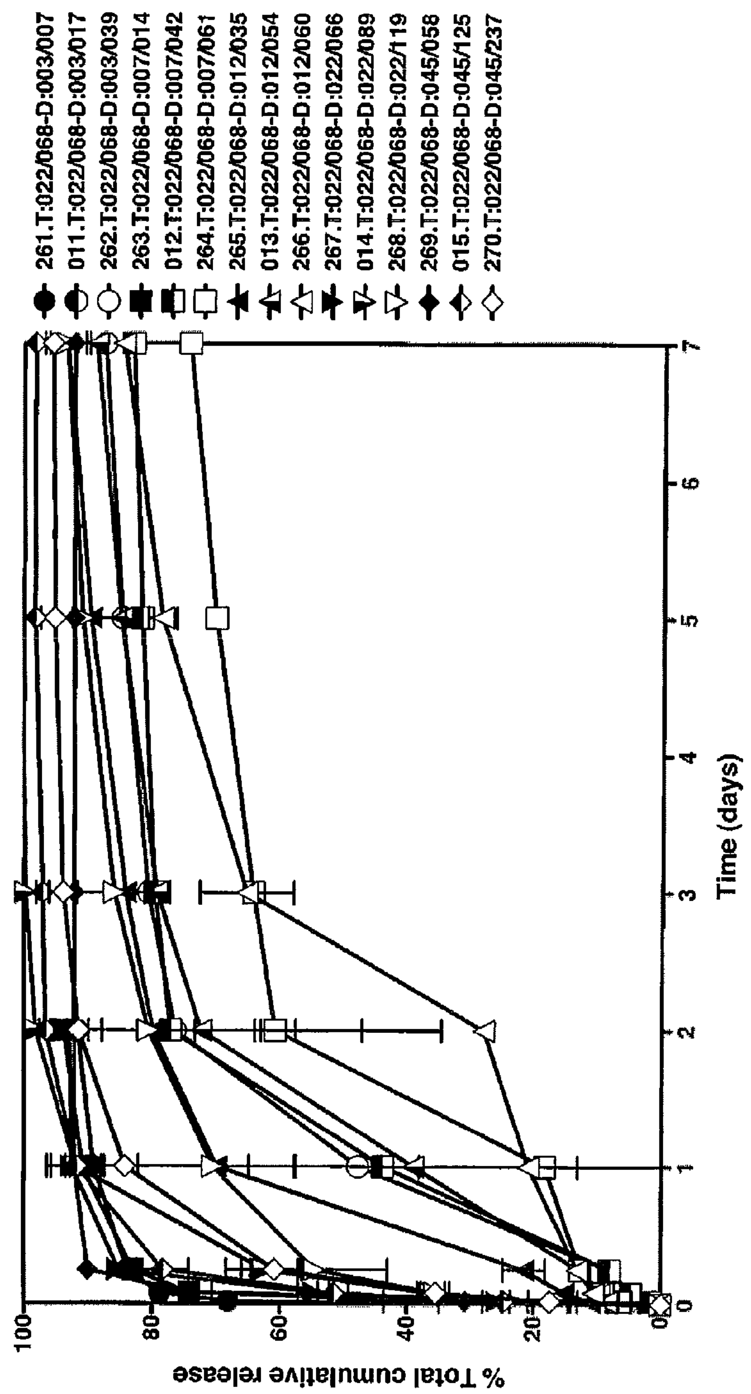
FIG. 16 is a graph showing the in vitro cumulative percent release of acetaminophen over time (days) from formulations based on triblock copolymer P1R3 (22 units of ethylene oxide and 68 units of lactic acid) mixed with various diblock copolymers (see Table 2 for details).
Figure 17:
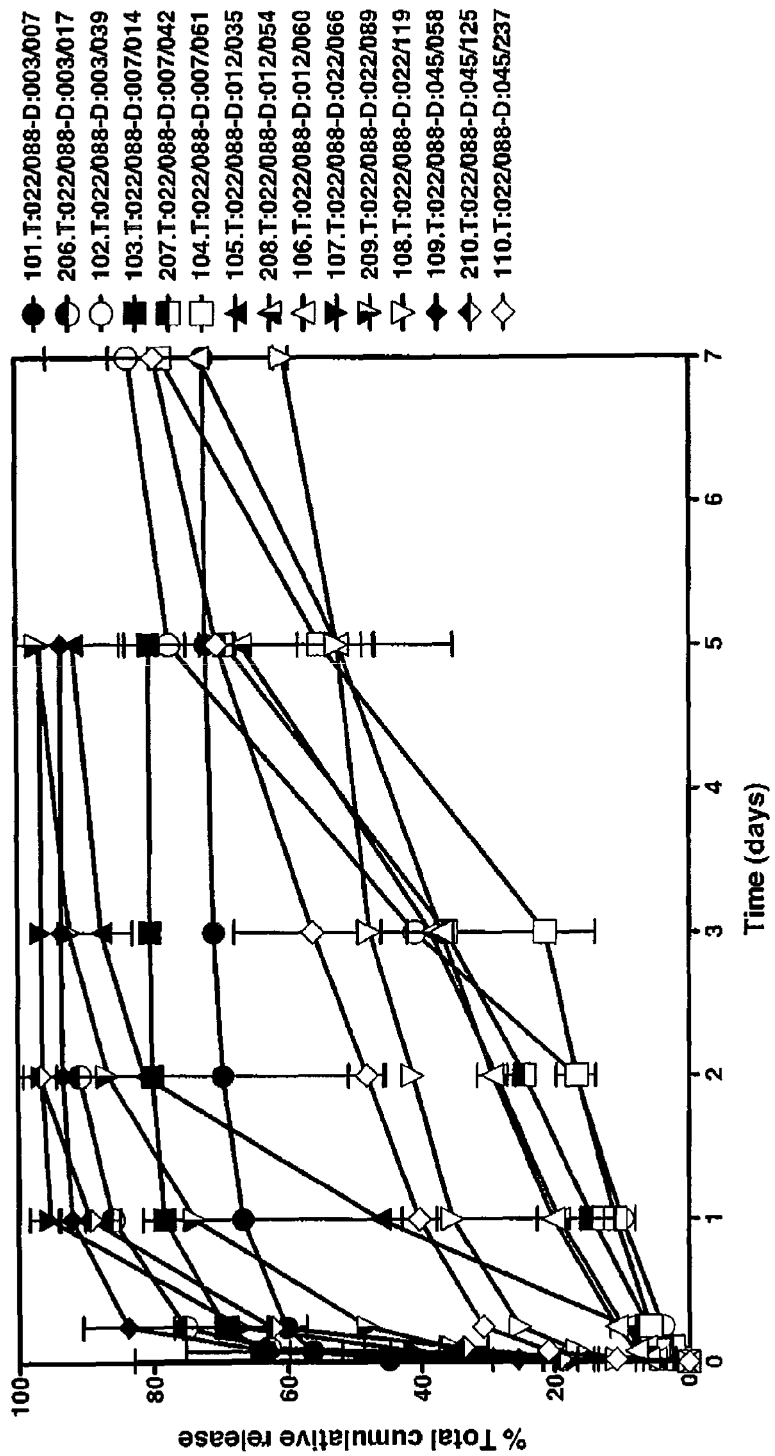
FIG. 17 is a graph showing the in vitro cumulative percent release of acetaminophen over time (days) from formulations based on triblock copolymer P1R4 (22 units of ethylene oxide and 88 units of lactic acid) mixed with various diblock copolymers (see Table 2 for details).
Figure 18:
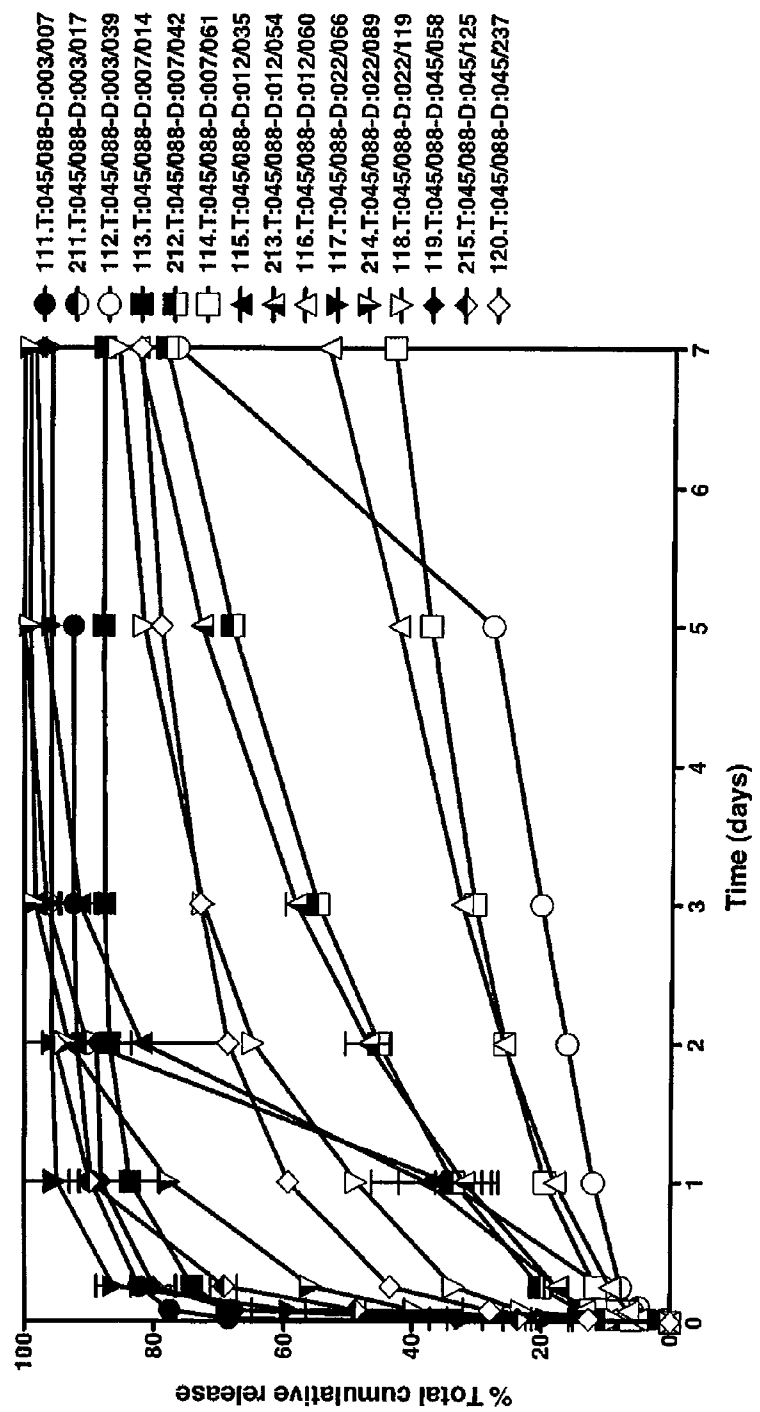
FIG. 18 is a graph showing the in vitro cumulative percent release of acetaminophen over time (days) from formulations based on triblock copolymer P2R2 (45 units of ethylene oxide and 88 units of lactic acid) mixed with various diblock copolymers (see Table 2 for details).
Figure 19:
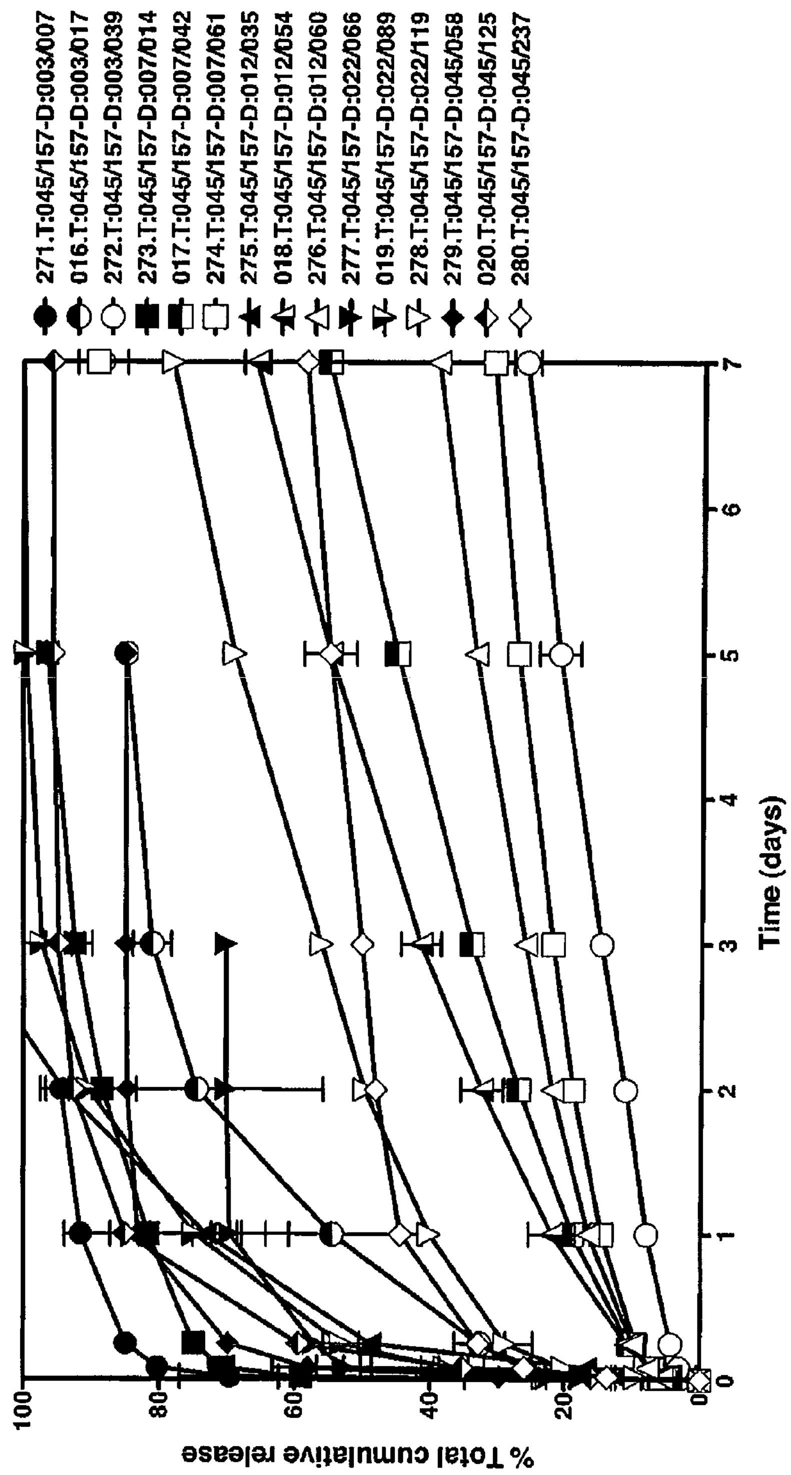
FIG. 19 is a graph showing the in vitro cumulative percent release of acetaminophen over time (days) from formulations based on triblockco polymer P2R3 (45 units of ethylene oxide and 157 units of lactic acid) mixed with various diblock copolymers (see Table 2 for details).
Figure 20:
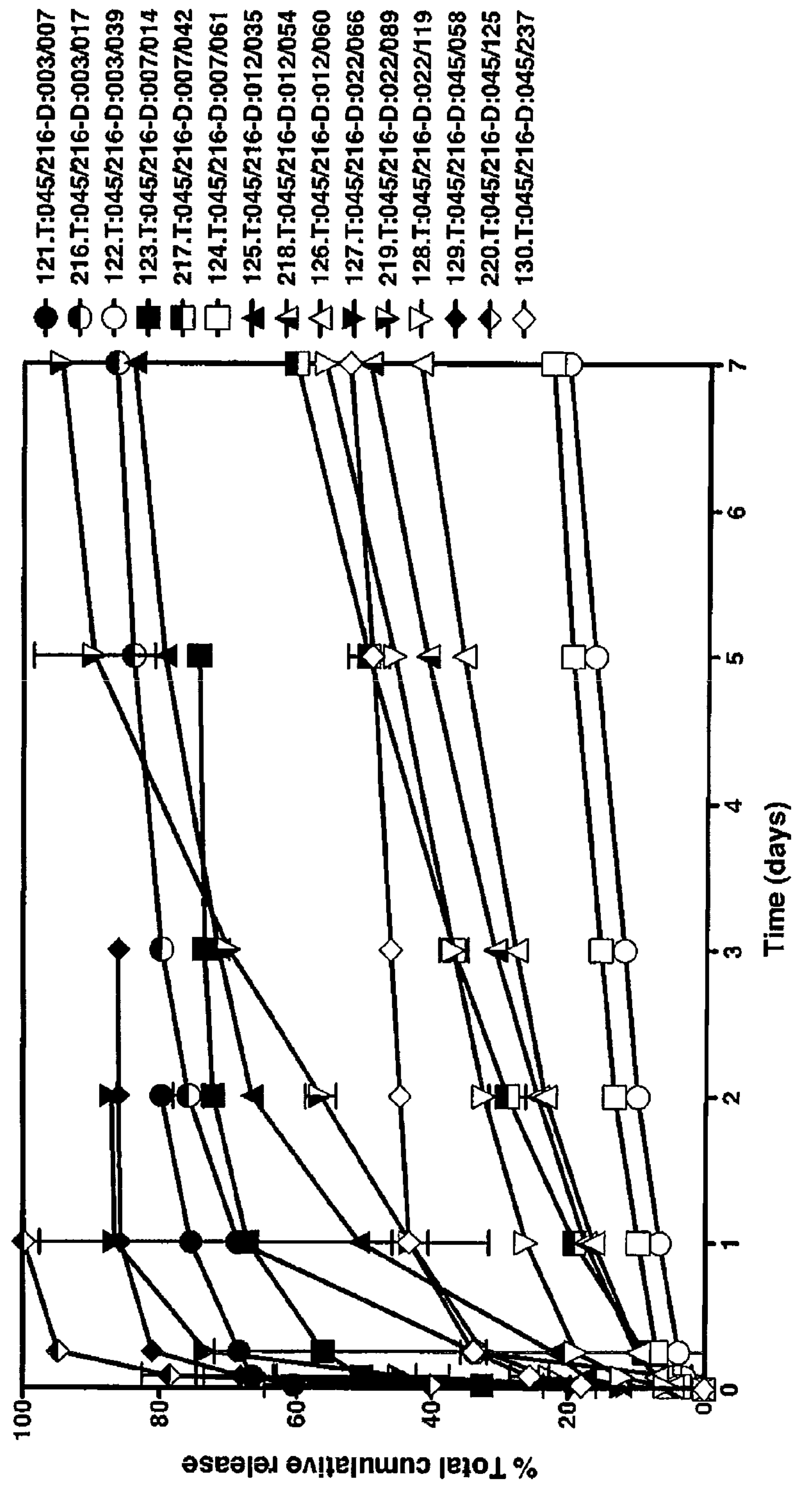
FIG. 20 is a graph showing the in vitro cumulative percent release of acetaminophen over time (days) from formulations based on triblock copolymer P2R5 (45 units of ethylene oxide and 216 units of lactic acid) mixed with various diblock copolymers (see Table 2 for details).
Figure 21:
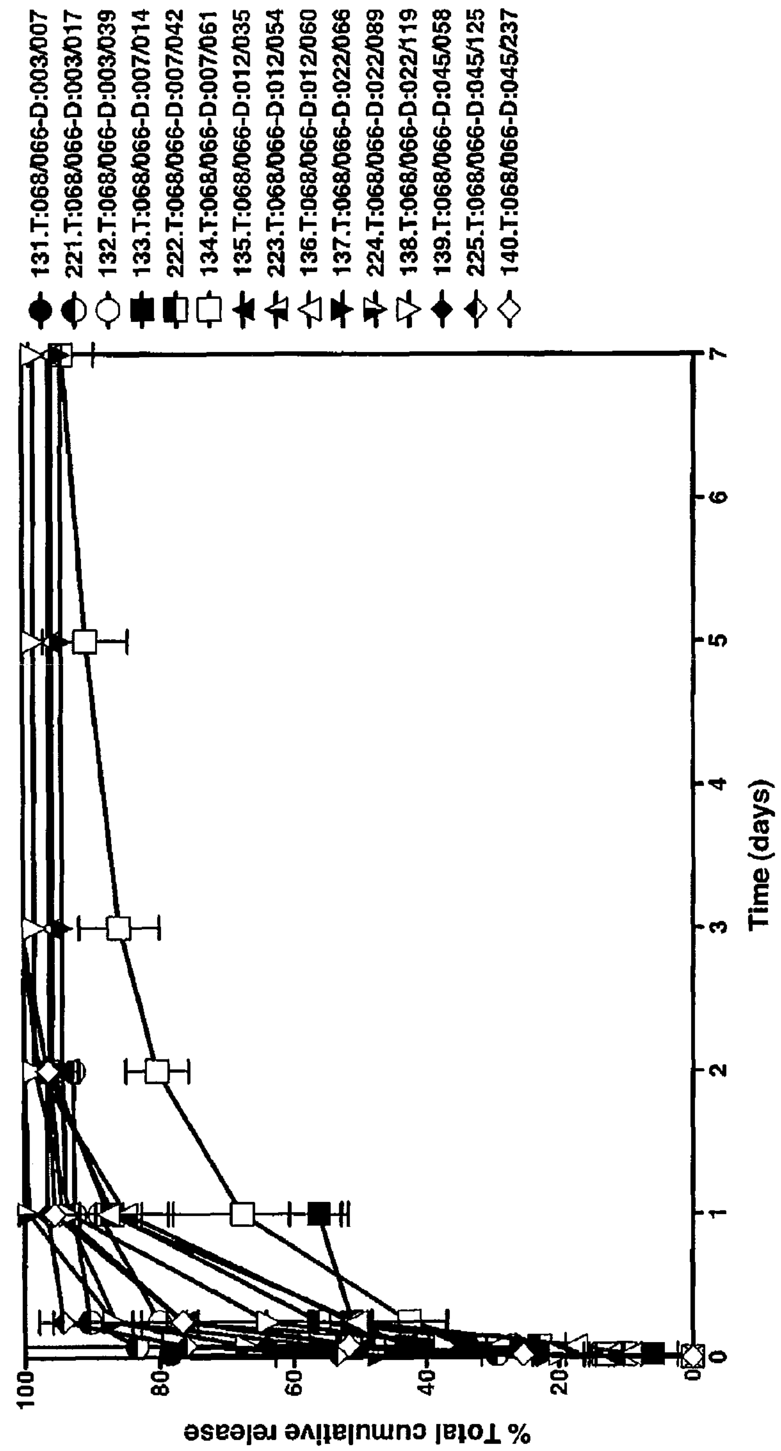
FIG. 21 is a graph showing the in vitro cumulative percent release of acetaminophen over time (days) from formulations based on triblock copolymer P3R1 (68 units of ethylene oxide and 66 units of lactic acid) mixed with various diblock copolymers (see Table 2 for details).
Figure 22:
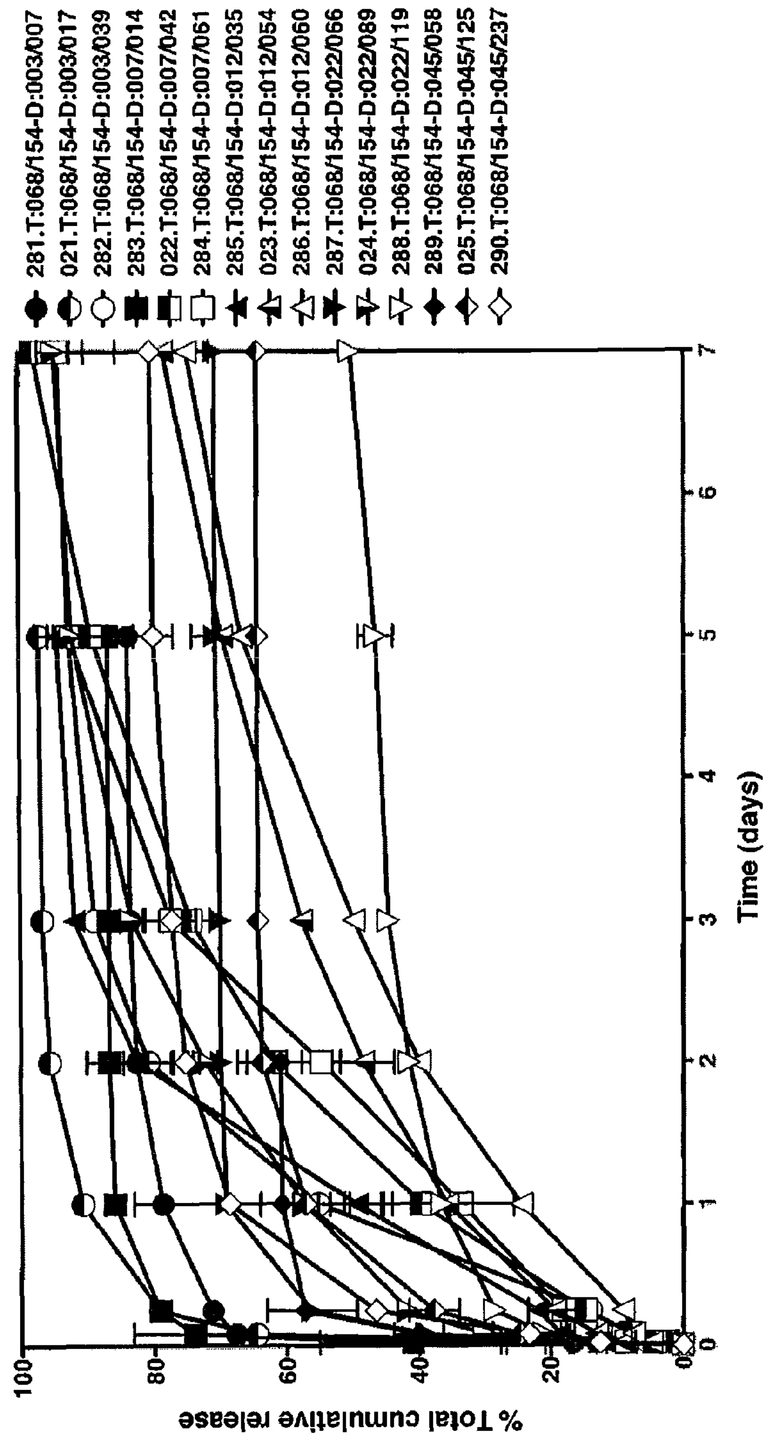
FIG. 22 is a graph showing the in vitro cumulative percent release of acetaminophen over time (days) from formulations based on triblock copolymer P3R2 (68 units of ethylene oxide and 154 units of lactic acid) mixed with various diblock copolymers (see Table 2 for details).
Figure 23:
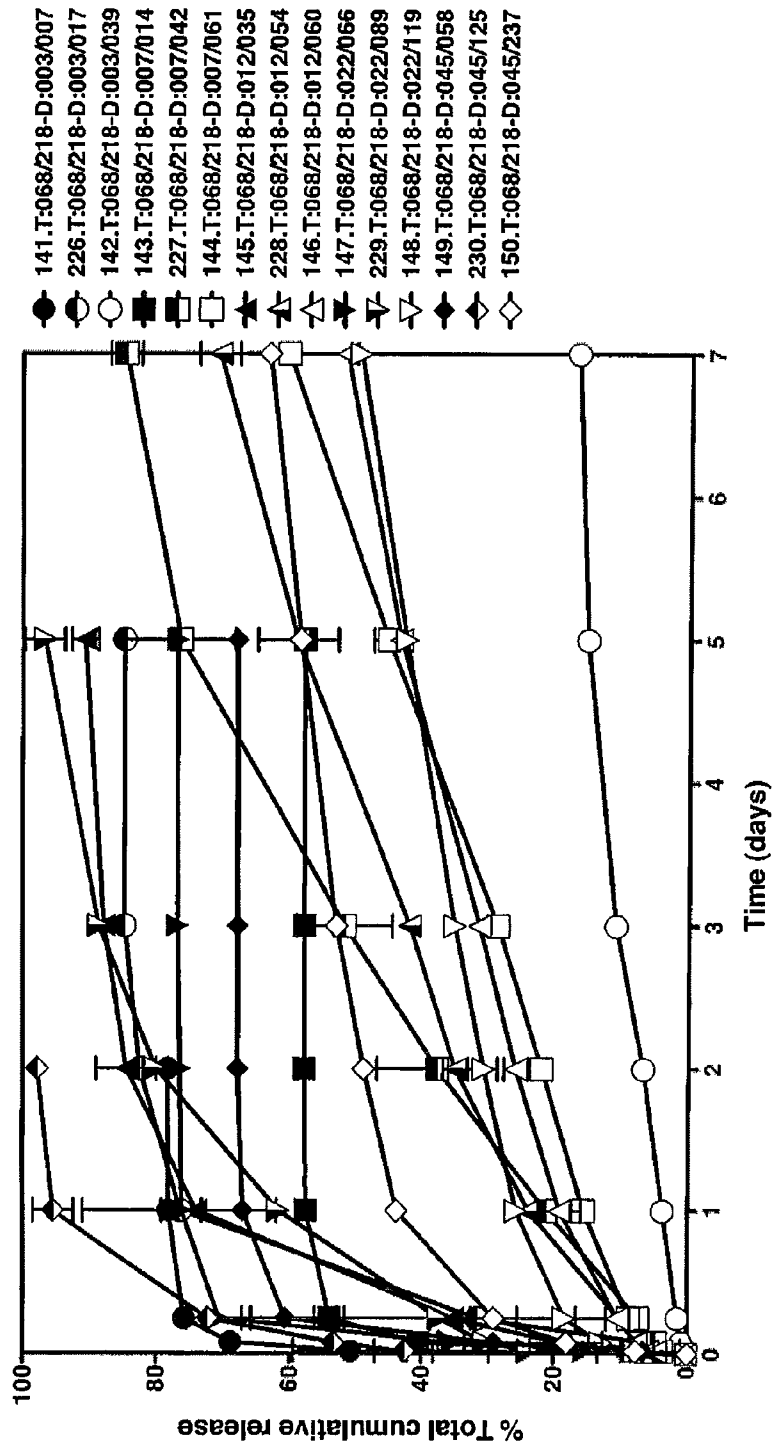
FIG. 23 is a graph showing the in vitro cumulative percent release of acetaminophen over time (days) from formulations based on triblock copolymer P3R3 (68 units of ethylene oxide and 218 units of lactic acid) mixed with various diblock copolymers (see Table 2 for details).
Figure 24:
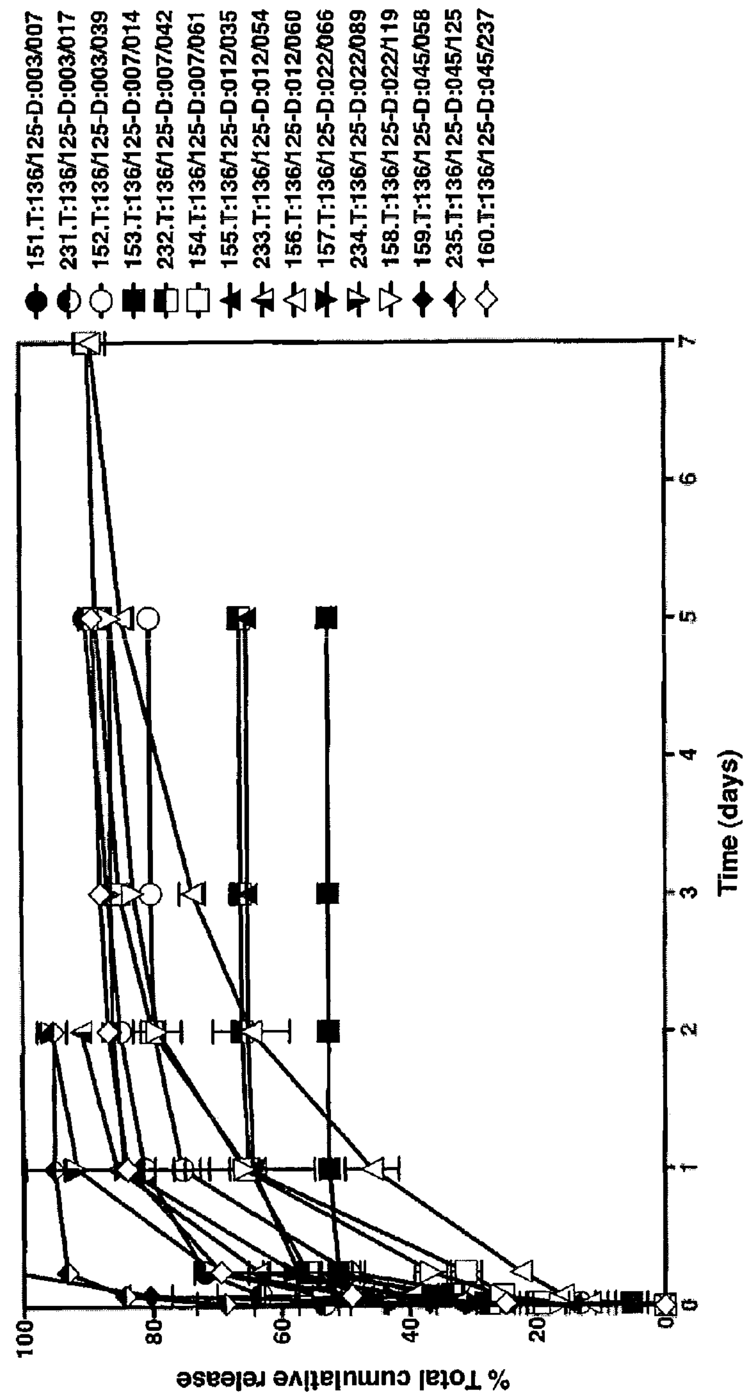
FIG. 24 is a graph showing the in vitro cumulative percent release of acetaminophen over time (days) from formulations based on triblock copolymer P6R0.9 (136 units of ethylene oxide and 125 units of lactic acid) mixed with various diblock copolymers (see Table 2 for details).
Figure 25:
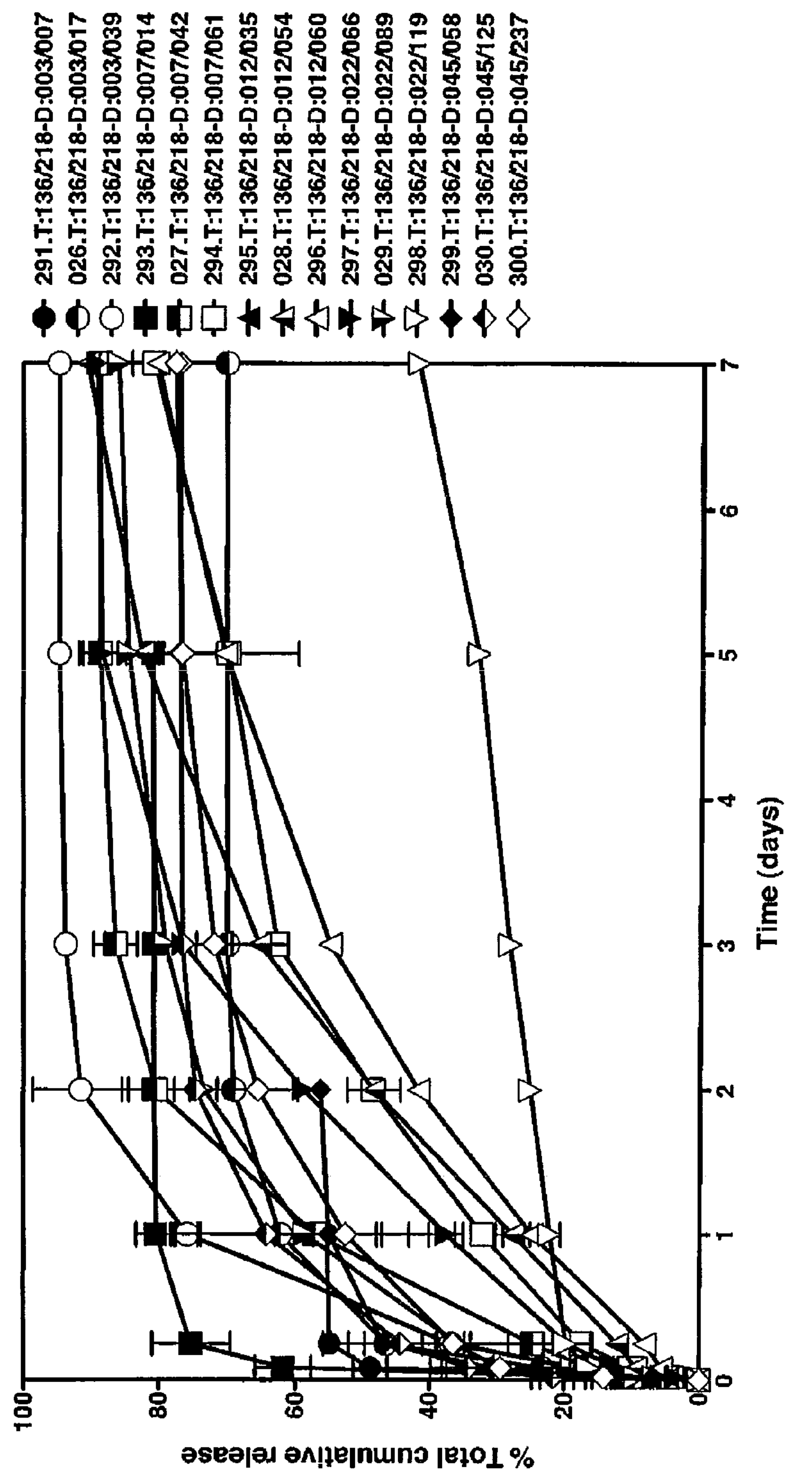
FIG. 25 is a graph showing the in vitro cumulative percent release of acetaminophen over time (days) from formulations based on triblock copolymer P6R1.6 (136 units of ethylene oxide and 218 units of lactic acid) mixed with various diblock copolymers (see Table 2 for details).
Figure 26:
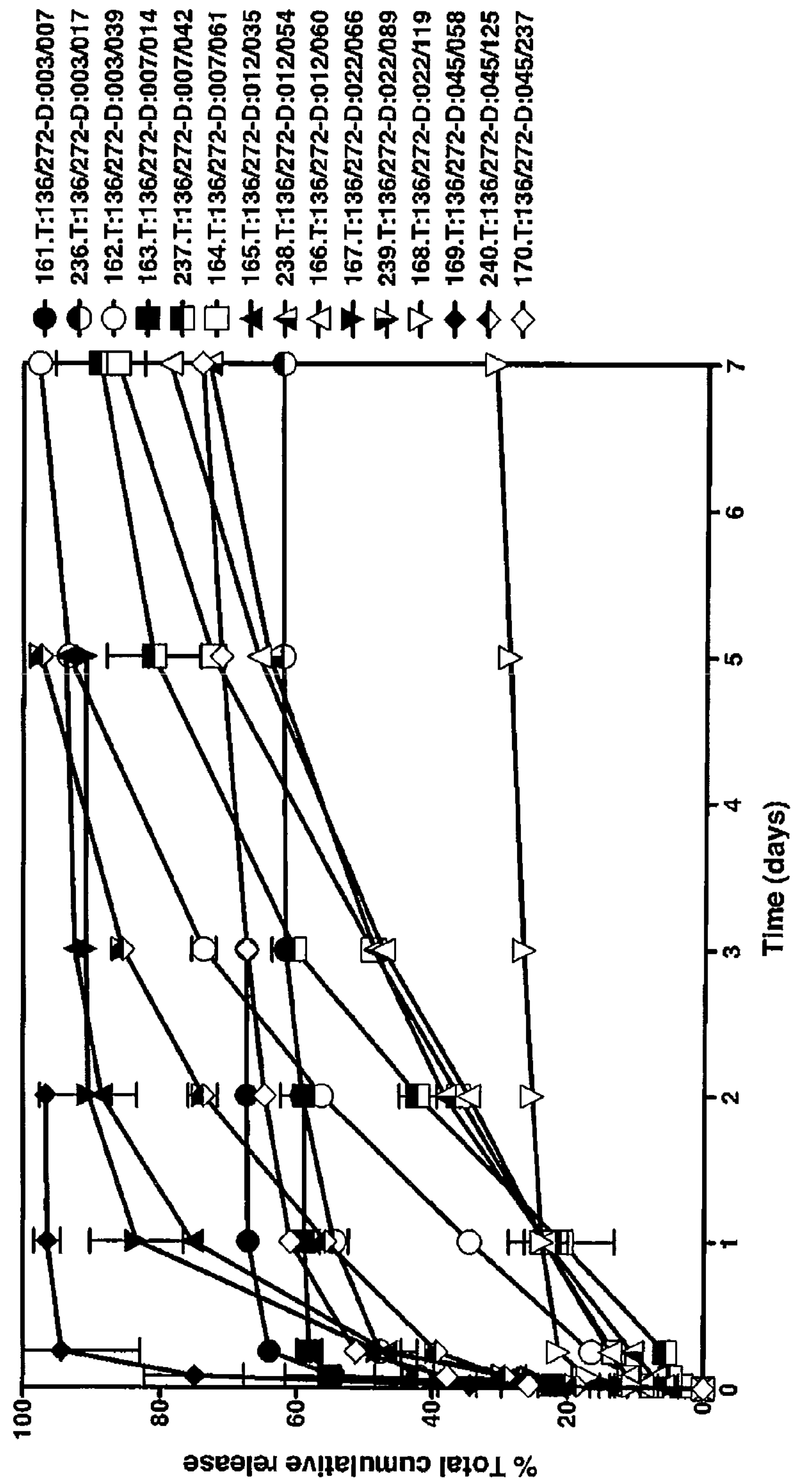
FIG. 26 is a graph showing the in vitro cumulative percent release of acetaminophen over time (days) from formulations based on triblock copolymer P6R2 (136 units of ethylene oxide and 272 units of lactic acid) mixed with various diblock copolymers (see Table 2 for details).
Figure 27:
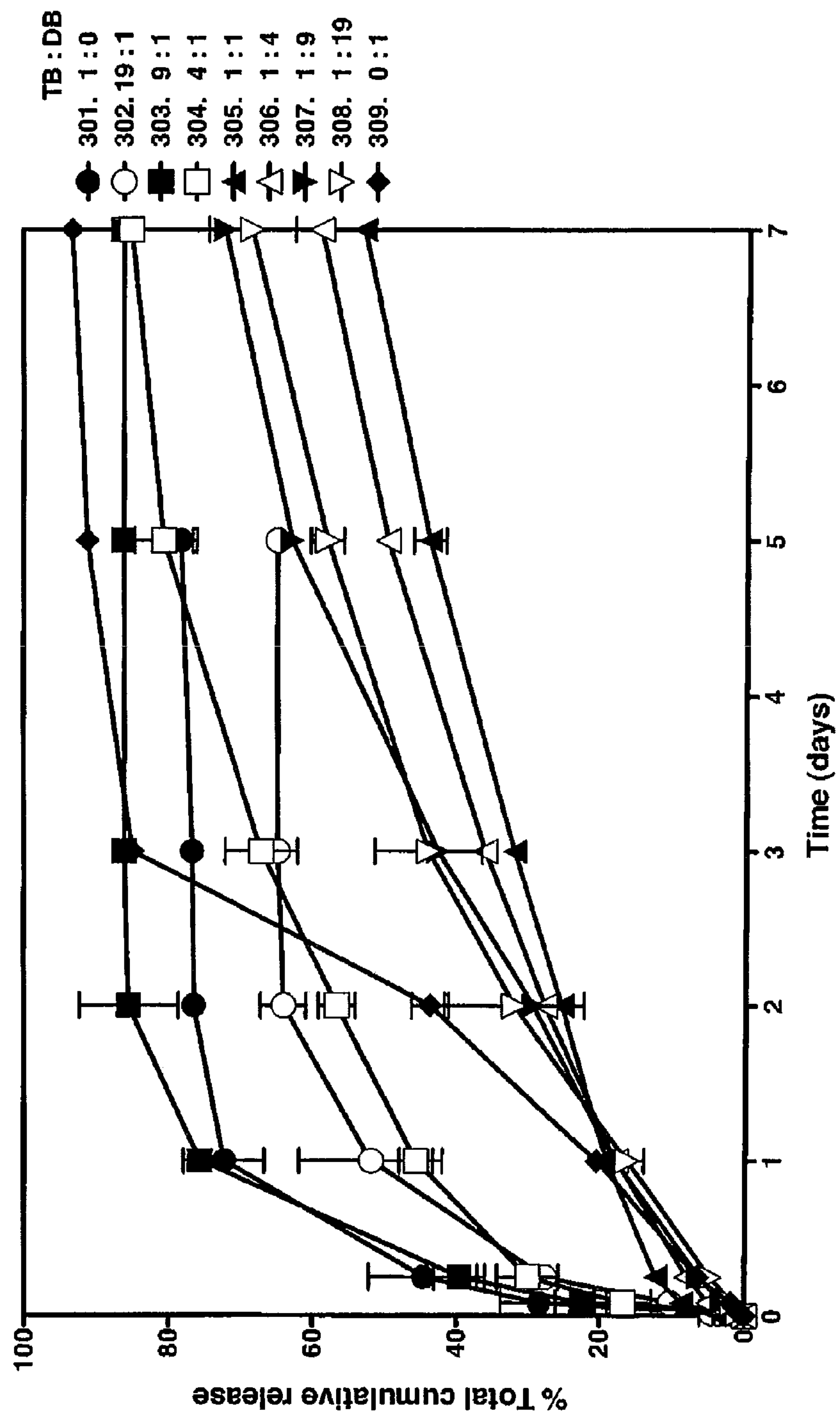
FIG. 27 is a graph showing the in vitro cumulative percent release of acetaminophen over time (days) from formulations based on triblock copolymer P2R4 (45 units of ethylene oxide and 157 units of lactic acid) mixed with diblock copolymer dP0.4R6 (7 units of ethylene oxide and 42 units of lactic acid) at different ratios (see Table 2 for details).
Figure 28:
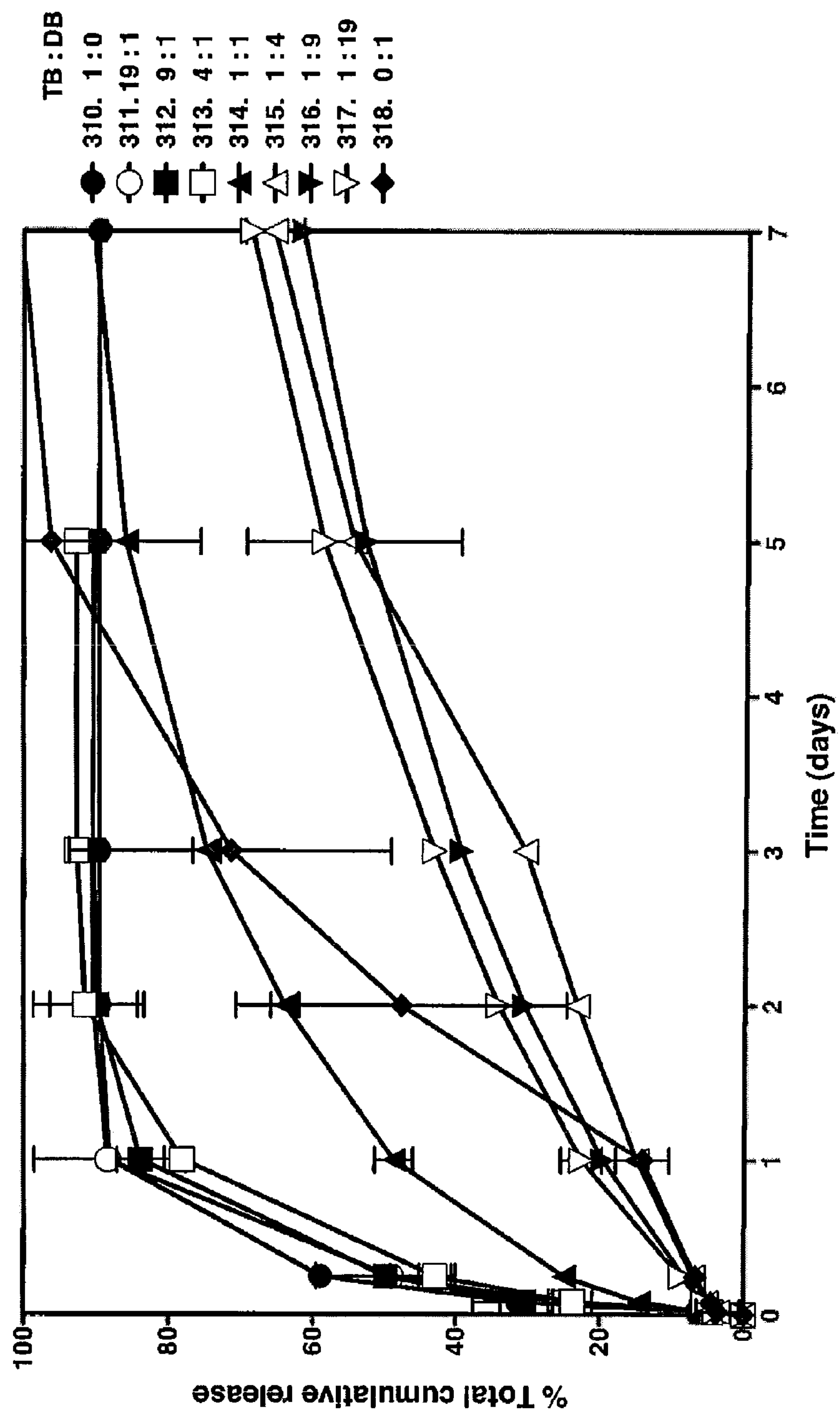
FIG. 28 is a graph showing the in vitro cumulative percent release of acetaminophen over time (days) from formulations based on triblock copolymer P2R4 (45 units of ethylene oxide and 157 units of lactic acid) mixed with diblock copolymer dP0.6R5 (12 units of ethylene oxide and 54 units of lactic acid) at different ratios (see Table 2 for details).
Figure 29:
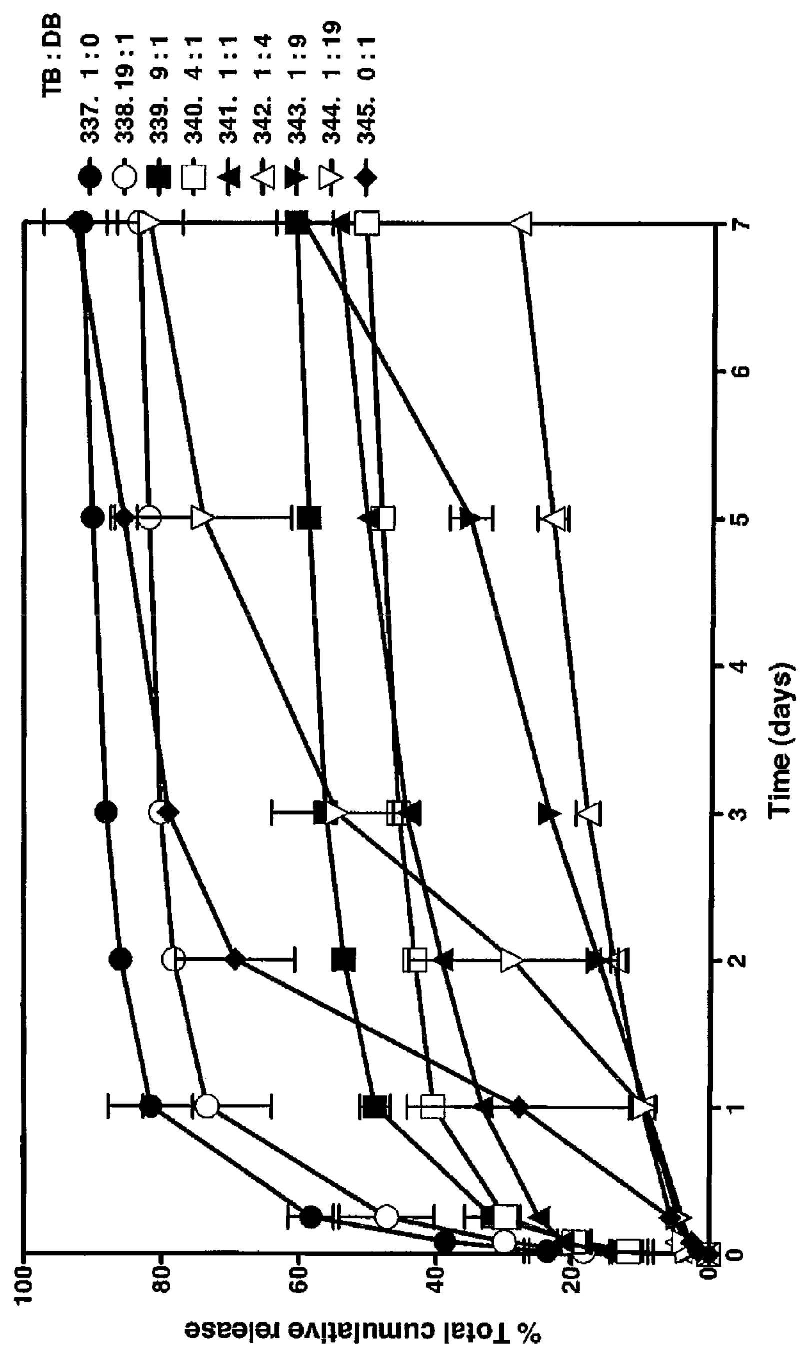
FIG. 29 is a graph showing the in vitro cumulative percent release of acetaminophen over time (days) from formulations based on triblock copolymer P2R5 (45 units of ethylene oxide and 216 units of lactic acid) mixed with diblock copolymer dP0.2R13 (3 units of ethylene oxide and 39 units of lactic acid) at different ratios (see Table 2 for details).

The results of one pharmacokinetic study are shown in FIG. 6. As shown in this Figure three of the five formulations sustain plasma concentration higher than 0.1 ng/ml for more than 28 days while giving a moderate initial drug burst release below 30 ng/ml.

Example 11

Blood Glucose Levels

Blood glucose levels with patients suffering from diabetes type 2 are taken prior to treatment. A control group having no treatment is used for this study. Patients of either gender are used in this study provided that they have diabetes type 2 and are between the ages of 35 and 60.

A GPL-1 analogue is formulated according to Examples 1 and 2 and has the chemical characteristics of number 230 in Table 1. The injectable liquid that is obtained is then injected into several patients at a dosage of 8 mg/ml. The control group is given PBS.

The amount of blood sugar levels and fructosamine is then measured for a period of 30 days, twice weekly, before meals and 2 hours after meals. The amounts of blood glucose after treatment are measured and the results are averaged. The values are shown in Table 6:

TABLE 6

| Week number | Patient number | Blood Glucose Level Before Meals in mmol/l | Blood Glucose Level After Meals In mmol/l | Fructosamine μmol |
|---|---|---|---|---|
| Prior to Treatment | 1 | 150 | 190 | 300 |
| | 2 | 130 | 175 | 320 |
| | 3 | 200 | 230 | 330 |
| | 4 | 220 | 240 | 360 |
| 1 | 1 | 90 | 150 | 280 |
| | 2 | 98 | 110 | 290 |
| | 3 | 120 | 160 | 330 |
| | 4 | 215 | 240 | 365 |
| 2 | 1 | 92 | 120 | 275 |
| | 2 | 95 | 100 | 287 |
| | 3 | 118 | 158 | 300 |
| | 4 | 210 | 230 | 370 |
| 3 | 1 | 92 | 110 | 270 |
| | 2 | 98 | 101 | 275 |
| | 3 | 115 | 155 | 280 |
| | 4 | 211 | 222 | 385 |

TABLE 6-continued

| Week number | Patient number | Blood Glucose Level Before Meals in mmol/l | Blood Glucose Level After Meals In mmol/l | Fructosamine μmol |
|---|---|---|---|---|
| 4 | 1 | 93 | 110 | 260 |
| | 2 | 85 | 100 | 260 |
| | 3 | 110 | 150 | 265 |
| | 4 | 223 | 244 | 365 |

Normal results for the glucose levels before meals range from 80 to 120 mmol/l. Normal results for the glucose levels after meals should be 160 mmol/l or less. Normal fructosamine levels are under 265. Between 265 and 280 indicates excellent blood glucose control; 280 and 500 indicates good blood glucose control; between 320 and 340 indicates fair blood glucose control; and over 350 indicates poor blood glucose control.

Patient 4 was administered the placebo.

These results show that when administered the biodegradable drug delivery compositions of the present invention are effective to treat diabetes type 2.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the claims, including equivalents thereof.

What is claimed is:

1. A biodegradable drug delivery composition comprising:

(a) a biodegradable triblock copolymer having the formula:

poly(lactic acid)$_v$-poly(ethylene glycol)$_w$,-poly(lactic acid)$_x$ wherein v and x are the number of repeat units ranging from 24 to 682 and w is the number of repeat units ranging from 4 to 273 and v=x or v≠x;

(b) a biodegradable diblock copolymer having the formula: methoxy poly(ethylene glycol)$_y$-poly(lactic acid)$_z$, wherein y and z are the number of repeat units, with y ranging from 3 to 45 and z ranging from 7 to 327 wherein the ratio of the biodegradable triblock copolymer of (a) and the biodegradable diblock copolymer of (b) is 1:3 to 1:8 or 1:1 to 1:19 or 3:2 to 1:19 in said biodegradable drug composition, which is insoluble in an aqueous environment; and (c) at least one pharmaceutically active principle.

2. A biodegradable drug delivery composition comprising:

(a) a biodegradable triblock copolymer present in an amount of 3.0% to 45% (w%/w%) of the total composition having the formula:

poly(lactic acid)$_v$-poly(ethylene glycol)$_w$-poly(lactic acid)$_x$ wherein v and x are the number of repeat units ranging from 24 to 682 and w is the number of repeat units ranging, from 4 to 273 v and x being lactyl or lactoyl repeat units and w being ethylene glycol repeat units and v=x or v≠x; (b) a biodegradable diblock copolymer present in an amount of 8.0% to 50% (w%/w%) of the total composition having the formula:

methoxy poly(ethylene glycol)$_y$-poly(lactic acid)$_z$ wherein y and z are the number of repeat units y ranging from 3 to 45 and z ranging from 7 to 327, y being the number of ethylene glycol repeat units and z the number of lactyl or lactoyl repeat units wherein the ratio of the biodegradable triblock copolymer of (a) and the biodegradable diblock copolymer of (b) is 1: 3 to 1:8 or 1:1 to 1:19 or 3:2 to 1:19 in said biodegradable drug composition, which is insoluble in an aqueous environment; and (c) at least one pharmaceutically active principle present in an amount of 1% to 20% (w%/w%) of the total composition.

3. The biodegradable drug delivery composition according to claim 1, wherein said composition is an injectable liquid and forms an implant when injected into the body or are small solid particles or rod implants or spatial formulations.

4. The biodegradable drug composition according to claim 1, wherein the ratio of the biodegradable triblock copolymer of (a) and the biodegradable diblock copolymer of (b) is selected from the group of 1:1, 1:2, 1:3, 1:4 and 1:5.

5. The biodegradable drug delivery composition according to claim 1, wherein the size of the polyethylene glycol chain ranges from 200 Da to 12 kDa or 194 Da to 12 kDa and the size of the methoxy polyethylene glycol chain ranges from 100 Da to 2 kDa or 164 Da to 2 kDA.

6. The biodegradable drug delivery composition according claim 1, further comprising a pharmaceutically acceptable vehicle.

7. The biodegradable drug delivery composition according to claim 1, wherein the pharmaceutically active principle is present in an amount of 1% to 20% (w%/w%) of the total composition.

8. The biodegradable drug delivery composition according to claim 1, wherein the copolymers are present in an amount of 20% to 50% (w%/w%) of the total composition.

9. The biodegradable drug delivery composition according to claim 1, wherein the triblock copolymer is present in an amount of 3.0% to 45% (w%/w%) of the total composition.

10. The biodegradable drug delivery composition according to claim 1, wherein the diblock copolymer is present in an amount of 8.0% to 50% (w%/w%) of the total composition.

11. The biodegradable drug delivery composition according to claim 1, wherein the polylactic repeat unit to ethylene oxide molar ratio in the composition is between 0.5 to 3.5 or 0.5 to 22.3 in the triblock copolymer and 2 to 6 or 0.8 to 13 in the diblock copolymer.

12. A method for preparing the biodegradable drug delivery composition of Claim 1, said method comprising:

(i) dissolving in an organic solvent (a) a biodegradable copolymer having the formula:

poly(lactic acid)$_v$-poly(ethylene glycol)$_w$-poly(lactic acid)$_x$, wherein v and x are the number of repeat units ranging from 24 to 682 and w is the number of repeat units ranging from 4 to 273 and v=x or v≠x; and (b) a biodegradable diblock copolymer having the formula: methoxy poly(ethylene glycol)$_y$-poly(lactic acid)$_z$ wherein y and z are the number of repeat units with y ranging from 3 to 45 and z ranging from 7 to 327 in a ratio of 1: 3 to 1:8 or 1:1 to 1:19 or 3:2 to 1:19 (a):(b) to form a polymer mixture, which is insoluble in an aqueous environment; and (ii) adding at least one pharmaceutically active principle to said polymer mixture.

13. A method for preparing the biodegradable drug delivery composition of Claim 1, said method comprising:

(i) dissolving in an organic solvent (a) a biodegradable triblock copolymer having the formula:

poly(lactic acid)$_v$-poly(ethylene glycol)$_w$-poly(lactic acid)$_x$ wherein v and x are the number of repeat units ranging from 24 to 682 and w is the number of repeat units ranging from 4 to 273 and v=x or v≠x; and (b) a biodegradable dibiock copolymer having the formula: methoxy poly(ethylene glycol)$_y$-poly(lactic acid)$_z$ wherein y and z are the number of repeat units, with y ranging from 3 to 45 and z ranging from 7 to 327 in a ratio of 1:3 to 1:8 or 1:1 to 1:19 or 3:2 to 1:19 (a):(b) to form a polymer mixture, which is insoluble in an aqueous environment; and (ii) adding at least one pharmaceutically active principle to said polymer mixture; and (iii) evaporating said solvent.

14. The method according to claim 12, wherein the organic solvent is selected from the group of benzyl alcohol, benzyl benzoate, dimethyl isosorbide (DMI), dimethyl sulfoxide (DMS0), ethyl acetate, ethyl benzoate, ethyl lactate, glycerol formal, methyl ethyl ketone, methyl isobutyl ketone, N-ethyl-2-pyrrolidone, N-methyl-2-pyrrolidinone(NMP), pyrrolidone-2, tetraglycol, triacetin, tributyrin, tripropionin, and mixtures thereof.

15. The method according to claims 12, wherein the organic solvent is present in an amount of 40% to 74% (w%/w%) of the total composition.

16. The biodegradable drug composition according to claim 1, further comprising an organic solvent selected from the group of benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone(NMP), pyrrolidone-2, tetraglycol, triacetin, tributyrin, tripropionin and mixtures thereof.

17. The biodegradable drug composition according to claim 2, further comprising an organic solvent selected from the group of benzyl alcohol, benzyl benzoate, dimethyl isosorbide (DMI), dimethyl sulfoxide (DMSO), ethyl acetate, ethyl benzoate, ethyl lactate, glycerol formal, methyl ethyl ketone, methyl isobutyl ketone, N-ethyl-2-pyrrolidone, N-methyl-2-pyrrolidinone(NMP), pyrrolidone-2, triacetin, tributyrin, tripropionin and mixtures thereof

18. The biodegradable drug delivery composition according to claim 17, wherein said composition is an injectable liquid and forms an implant when injected into the body or are small solid particles or rod implants or spatial formulations.

* * * * *